US005861500A

United States Patent [19]
Chang et al.

[11] Patent Number: 5,861,500
[45] Date of Patent: Jan. 19, 1999

[54] KAPOSI'S SARCOMA-ASSOCIATED HERPESVIRUS (KSHV) INTERLEUKIN 6 (IL-6) AND USES THEREOF

[75] Inventors: Yuan Chang, New York, N.Y.; Roy A. Bohenzky, Mountain View, Calif.; James J. Russo, New York, N.Y.; Isidore S. Edelman, New York, N.Y.; Patrick S. Moore, New York, N.Y.

[73] Assignee: The Trustees of Columbia University in the City of New York, New York, N.Y.

[21] Appl. No.: 686,349

[22] Filed: Jul. 25, 1996

[51] Int. Cl.⁶ .................. A61K 39/245; C07H 21/04; C07K 14/03; C12N 15/38
[52] U.S. Cl. .................. 536/23.72; 536/23.4; 536/24.3; 536/24.33; 536/24.5; 530/350; 530/388.3; 424/159.1; 424/147.1; 424/192.1; 424/229.1; 435/6; 435/69.1; 435/69.3; 435/235.1; 435/325; 435/252.1; 435/320.1
[58] Field of Search ................... 435/6, 69.1, 69.3, 435/235.1, 320.1, 325, 252.1; 536/23.72, 23.4, 24.5, 24.3, 24.33; 424/85.2, 229.1; 530/350, 388.3

[56] References Cited

U.S. PATENT DOCUMENTS

| | | |
|---|---|---|
| 5,188,828 | 2/1993 | Goldberg et al. |
| 5,217,881 | 6/1993 | Park |
| 5,264,209 | 11/1993 | Mikayama et al. |
| 5,300,292 | 4/1994 | Ulich |
| 5,338,833 | 8/1994 | Fowlkes |
| 5,338,834 | 8/1994 | Williams |
| 5,359,034 | 10/1994 | Skelly et al. |
| 5,376,368 | 12/1994 | Ulich |
| 5,470,824 | 11/1995 | Miles et al. |

OTHER PUBLICATIONS

Armstrong et al. (1994) Melanoma–derived interleukin 6 inhibits in vivo melanoma growth, J. Invest. Dermatol 102, 278–284 (Exhibit 2).
Burger et al. (1994) Interleukin–6 production in B–cell neoplasias and Castleman's disease: evidence for an additional paracrine loop, Annals Hematol, 69, 25–31 (Exhibit 3).
Emilie et al. (1992) Production of interleukin–6 in high grade B lymphomas, Curr. Top. Microbiol Immunol 182, 349–355 (Exhibit 4).
Evans et al. (1992) Tumor cell IL–6 gene expression is regulated by IL–1alpha/beta and TNFalpha: proposed feedback mechanisms induced by the interaction of tumor cells and macrophages, J. Leukocyte Biol. 52, 463–468 (Exhibit 5).
Karp and Broder (1991) Acquired immunodeficiency syndrome and non–Hodgkin's lymphomas, Cancer Research 51, 4743–4756 (Exhibit 6).
Klein (1995) Cytokine, cytokine receptors, transduction signals, and oncogenes in human multiple myeloma, Semin. Hematol. 32, 4–19 (Exhibit 7).

Lotz (1993) Interleukin–6, Cancer Invest. 11, 732–742 (Exhibit 8).
Rifas et al. (1995) Production of interleukin–6 in human osteoblasts and human bone marrow stromal cells: evidence that induction by interleukin–1 and tumor necrosis factor–alpha is not regulated by ovarian steroids, Endocrinology 136, 4056–4067 (Exhibit 9).
Tan et al. (1990) Expression of the interleukin 6 gene in rheumatoid synovial fibroblasts, J. Rheumatol 17, 1608–1612 (Exhibit 10).
Yuan et al. (1994) The signalling pathways of interleukin–6 and gamma interferon converge by the activation of different transcription factors which bind to common responsive DNA elements, Mol. Cell Biol. 14, 1657–1668 (Exhibit 11).
Albrecht et al. (1992) Primary structure of the herpesvirus saimiri genome, J Virol 66, 5407–5058 (Exhibit 2).
Almeida et al. (1994) Human cytomegalovirus alters interleukin–6 production by endothelial cells, Blood 83, 370–376 (Exhibit 3).
Birkenbach et al. (1993) Epstein–Barr virus–induced genes: first lymphocyte–specific G protein–coupled peptide receptors, J Virol 67, 2209 (Exhibit 4).
Tur and Brenner (Mar. 1996) Treatment of Kaposi's sarcoma, Arch Dermatol 132, 327–331 (Exhibit 5).
Chee et al. (1995) Analysis of the protein–coding content of the sequence of human cytomegalovirus strain AD169, Curr Top Microbiol Immunol 154, 125–169 (Exhibit 6).
Cleary et al. (1986) Cloning and structural analysis of cDNAs for bcl–2 and a hybrid bcl–2/immunoglobulin transcript resulting from the t(14;18) translocation, Cell 47, 19–28 (Exhibit 7).
Cohen et al. (1996) Interleukin 6 induces the expression of vascular endothelial growth factor, J Biol Chem 271, 736–741 (Exhibit 8).
Ensoli et al. (1992) Cytokines and growth factors in the pathogenesis of AIDS–associated Kaposi's sarcoma, Immunol Reviews, 127, 147–154 (Exhibit 9).
Finke et al. (1992) Expression bcl–2 in burkitt's lymphoma cell lines: induction by latent Epstein–Barr virus genes, Blood 80, 459–469 (Exhibit 10).
Finke et al. (1994) BCL–2 induction is part of the strategy of Epstein–Barr virus, Leuk Lymphoma 12, 413–419 (Exhibit 11).
Gao and Murphy (1994) Human cytomegalovirus open reading frame US28 encodes a functional beta chemokine receptor, J Biol Chem 269, 28539–28542 (Exhibit 12).
Holzinger et al. (1993) Effects of interleukin–1, –2, –4, –6, interferon–gamma and granulocyte/macrophage colony stimulating factor on human vascular endothelial cells, Immunol Lett 35, 109–117 (Exhibit 13).

(List continued on next page.)

*Primary Examiner*—Jeffrey Stucker
*Assistant Examiner*—Phuong T. Bui
*Attorney, Agent, or Firm*—John P. White; Cooper & Dunham LLP

[57] ABSTRACT

This invention provides an isolated DNA molecule which encodes interleukin 6 (IL-6) of Kaposi's sarcoma-associated herpesvirus. Antisense oligonucleotide molecules are also provided.

13 Claims, 39 Drawing Sheets

OTHER PUBLICATIONS

Jones et al. (1995) Infection of human endothelial cells with Epstein–Barr virus, J Exp Med 182, 1213–1221 (Exhibit 14).

Lafeuillade et al. (1996) IL–6 and b–FGF overproductions precede development of AIDS–associated Kaposi's sarcoma, J AIDS Hum Retrovirol 12, 95 (Exhibit 15).

Larcher et al. (1995) Expression of Epstein–Barr virus nuclear antigen–2 (EBNA2) induces CD21/CR2 ib B and T cell lines and shedding of soluble CD21, Eur J Immunol 25, 1713–1719 (Exhibit 16).

Lichtenstein et al. (1995) Interleukin–6 inhibits apoptosis of malignant plasma cells, Cellular Immunology 162, 248–255 (Exhibit 17).

Massung et al. (1994) Analysis of the complete genome of smallpox variola major virus strain bangladesh–1975, Virol 201, 215–240 (Exhibit 18).

Palmero et al. (1993) Cyclins D1 and D2 are differentially expressed in human B–lypoid cell lines, Oncogene 8, 1049 (Exhibit 19).

Scala et al. (1990) Expression of an exogenous interleukin 6 gene in human Epstein Barr virus B cells confers growth advantage and in vivo tumorigencity, J Exp Med 172, 61–68 (Exhibit 20).

Renne et al. (Mar. 1996) Lytic growth of Kaposi's sarcoma–associated herpesvirus (human herpesvirus 8) in culture, Nat Med 2, 342–346 (Exhibit 21).

Shen and Shenk (1995) Viruses and apoptosis, Curr Opin Genet Dev 5, 105–111 (Exhibit 22).

Weiss (Mar. 1996) Human herpesvirus 8 in lymphoma and Kaposi's sarcoma: now the virus can be propagated, Nat Med 2, 277–278 (Exhibit 23).

Tosato et al. (1990) Identification of interleukin–6 as an autocrine growth factor for Epstein–Barr virus–immortalized B cells, J Virol 64, 3033–3041 (Exhibit 24); and.

Zhong et al (1996) Restricted expression of Kaposi sarcoma–associated herpesvirus (human herpesviurs 8) genes in Kaposi sarcoma, Proc Natl Acad Sci USA 93, 6641–6646 (Exhibit 25).

Chang et al. Science vol. 266, 16 Dec. 1994, pp. 1865–1869.

FIG. 3A-1

SEQ. I.D. NO. 1

| | | | | | |
|---|---|---|---|---|---|
| TCGAGTCGGA | GAGTTGGCAC | AGGCCTTGAG | CTCGCTGTGA | CGTTCTCACG | GTGTTGGTTG | 60 |
| GGATCAGCTG | GTGACTCAGA | CAAGTCTTGA | GCTCTACAAC | GTAACATACG | GGCTGATGCC | 120 |
| CACCCGATAC | CAGAATTACG | CAGTCGGCAA | TTCTGTGCCC | TAGAGTCACC | TCAAAGAATA | 180 |
| ATCTGTGGTG | TCCAAGGGGA | GGGTTCTGGG | GCCGGCTACT | TAGAAACCGC | CATAGATCGG | 240 |
| GCAGGGTGGA | GTACTTGAGG | AGCCGGCGGT | AGGTGGCCAG | GTGGGCCCGG | TTACCTGCTC | 300 |
| TTTTGCGTGC | TGCTGGAAGC | CTGCTCAGGG | ATTTCTTAAC | CTCGGCCTCG | GTTGGACGTA | 360 |
| CCATGGCAGA | AGGCGGTTTT | GGAGCGGACT | CGGTGGGGCG | CGGCGGAGAA | AAGGCCTCTG | 420 |
| TGACTAGGGG | AGGCAGGTGG | GACTTGGGGA | GCTCGGACGA | CGAATCAAGC | ACCTCCACAA | 480 |
| CCAGCACGGA | TATGGACGAC | CTCCCTGAGG | AGAGGAAACC | ACTAACGGGA | AGTCTGTAA | 540 |
| AAACCTCGTA | CATATACGAC | GTGCCCACCG | TCCCGACCAG | CAAGCCGTGG | CATTTAATGC | 600 |
| ACGACAACTC | CCTCTACGCA | ACGCCTAGGT | TTCCGCCCAG | ACCTCTCATA | CGGCACCCTT | 660 |
| CCGAAAAAGG | CAGCATTTTT | GCCAGTCGGT | TGTCAGCGAC | TGACGACGAC | TCGGGAGACT | 720 |
| ACGCGCCAAT | GGATCGCTTC | GCCTTCCAGA | GCCCCAGGGT | GTGTGGTCGC | CCTCCCCTTC | 780 |
| CGCCTCCAAA | TCACCCACCT | CCGGCAACTA | GGCCGGCAGA | CGCGTCAATG | GGGGACGTGG | 840 |
| GCTGGGCGGA | TCTGCAGGGA | CTCAAGAGGA | CCCCAAAGGG | ATTTTTAAAA | ACATCTACCA | 900 |
| AGGGGGGCAG | TCTCAAAGCC | CGTGGACGCG | ATGTAGGTGA | CCGTCTCAGG | GACGGCGGCT | 960 |
| TTGCCTTTAG | TCCTAGGGGC | GTGAAATCTG | CCATAGGGCA | AAACATTAAA | TCATGGTTGG | 1020 |
| GGATCGGAGA | ATCATCGGCG | ACTGCTGTCC | CCGTCACCAC | GCAGCTTATG | GTACCGGTGC | 1080 |
| ACCTCATTAG | AACGCCTGTG | ACCGTGGACT | ACAGGAATGT | TTATTTGCTT | TACTTAGAGG | 1140 |
| GGGTAATGGG | TGTGGGCAAA | TCAACGCTGG | TCAACGCCGT | GTGCGGGATC | TTGCCCCAGG | 1200 |
| AGAGAGTGAC | AAGTTTTCCC | GAGCCCATGG | TGTACTGGAC | GAGGGCATTT | ACAGATTGTT | 1260 |
| ACAAGGAAAT | TTCCCACCTG | ATGAAGTCTG | GTAAGGCGGG | AGACCCGCTG | ACGTCTGCCA | 1320 |
| AAATATACTC | ATGCCAAAAC | AAGTTTTCGC | TCCCCTTCCG | GACGAACGCC | ACCGCTATCC | 1380 |
| TGCGAATGAT | GCAGCCCTGG | AACGTTGGGG | GTGGGTCTGG | GAGGGCACT | CACTGGTGCG | 1440 |
| TCTTTGATAG | GCATCTCCTC | TCCCCAGCAG | TGGTGTTCCC | TCTCATGCAC | CTGAAGCACG | 1500 |
| GCCGCCTATC | TTTTGATCAC | TTCTTTCAAT | TACTTCCAT | CTTTAGAGCC | ACAGAAGGCG | 1560 |
| ACGTGGTCGC | CATTCTCACC | CTCTCCAGCG | CCGAGTCGTT | GCGGCGGGTC | AGGGCGAGGG | 1620 |
| GAAGAAAGAA | CGACGGGACG | GTGGAGCAAA | ACTACATCAG | AGAATTGGCG | TGGGCTTATC | 1680 |
| ACGCCGTGTA | CTGTTCATGG | ATCATGTTGC | AGTACATCAC | TGTGGAGCAG | ATGGTACAAC | 1740 |
| TATGCGTACA | AACCACAAAT | ATTCCGGAAA | TCTGCTTCCG | CAGCGTGCGC | CTGGCACACA | 1800 |
| AGGAGGAAAC | TTTGAAAAAC | CTTCACGAGC | AGAGCATGCT | ACCTATGATC | ACCGGTGTAC | 1860 |

FIG. 3A-2

```
TGGATCCCGT GAGACATCAT CCCGTCGTGA TCGAGCTTTG CTTTTGTTTC TTCACAGAGC    1920
TGAGAAAATT ACAATTTATC GTAGCCGACG CGGATAAGTT CCACGACGAC GTATGCGGCC    1980
TGTGGACCGA AATCTACAGG CAGATCCTGT CCAATCCGGC TATTAAACCC AGGGCCATCA    2040
ACTGGCCAGC ATTAGAGAGC CAGTCTAAAG CAGTTAATCA CCTAGAGGAG ACATGCAGGG    2100
TCTAGCCTTC TTGGCGGCCC TTGCATGCTG GCGATGCATA TCGTTGACAT GTGGAGCCAC    2160
TGGCGCGTTG CCGACAACGG CGACGACAAT AACCCGCTCC GCCACGCAGC TCATCAATGG    2220
GAGAACCAAC CTCTCCATAG AACTGGAATT CAACGGCACT AGTTTTTTTC TAAATTGGCA    2280
AAATCTGTTG AATGTGATCA CGGAGCCGGC CCTGACAGAG TTGTGGACCT CCGCCGAAGT    2340
CGCCGAGGAC CTCAGGGTAA CTCTGAAAAA GAGGCAAAGT CTTTTTTTCC CCAACAAGAC    2400
AGTTGTGATC TCTGGAGACG GCCATCGCTA TACGTGCGAG GTGCCGACGT CGTCGCAAAC    2460
TTATAACATC ACCAAGGGCT TTAACTATAG CGCTCTGCCC GGGCACCTTG GCGGATTTGG    2520
GATCAACGCG CGTCTGGTAC TGGGTGATAT CTTCGCATCA AAATGGTCGC TATTCGCGAG    2580
GGACACCCCA GAGTATCGGG TGTTTACCC AATGAATGTC ATGGCCGTCA AGTTTTCCAT    2640
ATCCATTGGC AACAACGAGT CCGGCGTAGC GCTCTATGGA GTGGTGTCGG AAGATTTCGT    2700
GGTCGTCACG CTCCACAACA GGTCCAAAGA GGCTAACGAG ACGGCGTCCC ATCTTCTGTT    2760
CGGTCTCCCG GATTCACTGC CATCTCTGAA GGGCCATGCC ACCTATGATG AACTCACGTT    2820
CGCCCGAAAC GCAAAATATG CGCTAGTGGC GATCCTGCCT AAAGATTCTT ACCAGACACT    2880
CCTTACAGAG AATTACACTC GCATATTTCT GAACATGACG GAGTCGACGC CCCTCGAGTT    2940
CACGCGGACG ATCCAGACCA GGATCGTATC AATCGAGGCC AGGCGCGCCT GCGCAGCTCA    3000
AGAGGCGGCG CCGGACATAT TCTTGGTGTT GTTTCAGATG TTGGTGGCAC ACTTTCTTGT    3060
TGCGCGGGGC ATTGCCGAGC ACCGATTTGT GGAGGTGGAC TGCGTGTGTC GGCAGTATGC    3120
GGAACTGTAT TTTCTCCGCC GCATCTCGCG TCTGTGCATG CCCACGTTCA CCACTGTCGG    3180
GTATAACCAC ACCACCCTTG GCGCTGTGGC CGCCACACAA ATAGCTCGCG TGTCCGCCAC    3240
GAAGTTGGCC AGTTTGCCCC GCTCTTCCCA GGAAACAGTG CTGGCCATGG TCCAGCTTGG    3300
CGCCCGTGAT GGCGCCGTCC CTTCCTCCAT TCTGGAGGGC ATTGCTATGG TCGTCGAACA    3360
TATGTATACC GCCTACACTT ATGTGTACAC ACTCGGCGAT ACTGAAAGAA AATTAATGTT    3420
GGACATACAC ACGGTCCTCA CCGACAGCTG CCCGCCCAAA GACTCCGGAG TATCAGAAAA    3480
GCTACTGAGA ACATATTTGA TGTTCACATC AATGTGTACC AACATAGAGC TGGGCGAAAT    3540
GATCGCCCGC TTTTCCAAAC CGGACAGCCT TAACATCTAT AGGGCATTCT CCCCCTGCTT    3600
TCTAGGACTA AGGTACGATT TGCATCCAGC CAAGTTGCGC GCCGAGGCGC CGCAGTCGTC    3660
CGCTCTGACG CGGACTGCCG TTGCCAGAGG AACATCGGGA TTCGCAGAAT TGCTCCACGC    3720
```

FIG. 3A-3

```
GCTGCACCTC GATAGCTTAA ATTTAATTCC GGCGATTAAC TGTTCAAAGA TTACAGCCGA    3780
CAAGATAATA GCTACGGTAC CCTTGCCTCA CGTCACGTAT ATCATCAGTT CCGAAGCACT    3840
CTCGAACGCT GTTGTCTACG AGGTGTCGGA GATCTTCCTC AAGAGTGCCA TGTTTATATC    3900
TGCTATCAAA CCCGATTGCT CCGGCTTTAA CTTTTCTCAG ATTGATAGGC ACATTCCCAT    3960
AGTCTACAAC ATCAGCACAC CAAGAAGAGG TTGCCCCCTT TGTGACTCTG TAATCATGAG    4020
CTACGATGAG AGCGATGGCC TGCAGTCTCT CATGTATGTC ACTAATGAAA GGGTGCAGAC    4080
CAACCTCTTT TTAGATAAGT CACCTTTCTT TGATAATAAC AACCTACACA TTCATTATTT    4140
GTGGCTGAGG GACAACGGGA CCGTAGTGGA GATAAGGGGC ATGTATAGAA GACGCGCAGC    4200
CAGTGCTTTG TTTCTAATTC TCTCTTTTAT TGGGTTCTCG GGGGTTATCT ACTTTCTTTA    4260
CAGACTGTTT TCCATCCTTT ATTAGACGGT CAATAAAGCG TAGATTTTTA AAAGGTTTCC    4320
TGTGCATTCT TTTTGTATGG GCATATACTT GGCAAGAAAT CCGAGCACCT CAGAAAGTGG    4380
ATTGCCGTCA CATATCAGTT CGACCACCCC TGCACCTAGC CATGCGGCGC TTTGACGGTC    4440
TTTGGGGCTA CACATCATAA AGTACTTTTC CATGGCTTCT ATAAGCACCT TGGAACAATC    4500
TGGGGGTTGG CGAATGGGTT CCCTAAACGG GAAATCCTCT ATGGTATTCA GGCAGAAGAC    4560
CGCGTCCTCC ACCCGACGTT TGAGTCTTTC TAGCAGAGCG CCGAAGAACT CCCGCTCGTG    4620
TGTTTTCGCA GGGGCAAGTT CTGCGCCGTA CAGCGATGAG AAACACGACA CGATGTTTTC    4680
CAGCCCCATG CTGCGCAGCA ACACGTGCTT CAGGAACAGG TGTTGTAGCC GGTTCAGTTT    4740
TAGCTTGGGT AGAAAAGTTA TCGAGTTGTT AGCACGCTCC ATGATGGTAA CGGTGTTGAA    4800
GTCACAGACC GGGCTTTCTC CGAGTCTCGG CCGCCTGAGT CCAATCATGT AGAACATAGA    4860
CGCGGCCTCG TTGTCTGTGT TAAGTGACAC GATATCCCGT TCGCAAACCT GTGCGATGTT    4920
GTGTTTCAGT ATAGATCTGG TCTGACCGGC ACGGGTGTT ATGGGTGAC GCGGTAAAGG      4980
CGACTCTGGG TCAAACACCT TTATGCGGTT GGCGGCCTCG TCGATGACGA CACGCTTGTT    5040
CGCGGCGTGT ATGGGGACGC GACGGCATCC CGCTGGCAGA TCTATAATCT TAAAGTTGGT    5100
ATAAGACTGG TCGCTCGTTA TGGCCAGCCG GCACTCCGGT AGTATCTGCG TGTCCTCGAA    5160
TTCGTGGCCG CGTACGACTG GCTTGGAGTG CAGGTAAACG CCAAGAGATG CGGTCTCTTC    5220
GCCTACGCAC AAGTGGCTTC TTAACGCGTA GGGGTGCGGT GAGAGCATGA TCCGTAGCAA    5280
CGATAGTTCC GGGTGCCTAG CCGCGTAGAG TGGCAGGGTA CGAGTCCG GAGTCCCAAA      5340
CTTTTCGAAC AACAGTGGCA TCGGGACTTC AGGATTAGAG ACTCCCACCA TGGCCGCCAC    5400
CGCCGGAGAG GTCAAGACGT GAAACACGCG CTCGCCTGTC GACAGGCGCG CCGCGCCCTC    5460
TACTAGACTA GCCTTCACGT CCGGAACTCG TAACATAGCT TAGACCAGCG GACGGACGCA    5520
ACGTACGCGG GGATCGGCTG GCGGTGTCTG CTCGTTGGAC GCGGCCGTTC GGTGGCGCCA    5580
```

FIG. 3A-4

```
GTGCAGGCCT AGTTTGCGAA TGGCGTGACG GACAATTTGT GGCTTTAGAG CGGCGAACCG    5640
ATGACCCGTG GTGGCGACGA ACGAAATGAA GTTTGCATTG CGGCCCAACT CGTCTAGCCT    5700
GGTCTTCTTG TTTCGGGCAT AGATTTTCGG GATTAGGTTA CACTTTTTAT ATCCCAGTAC    5760
TGCGCACTCG TGTTTGCTTT TAGTGTGACT GATTATCTTC TTTGAGAAGT CAAACAGGCC    5820
CCGGGCGGCG GCTCGCCTAA TGCAAGCCAC GTCAAGCCTG AGAAACGAAC AGCATTCCAC    5880
CAGACACTCC AGGAACCTTT TGTGTAGCGT CTGTATTTGG GAACGGTTTC TGTGCTCAAG    5940
TAGGGAGAAT ATTCTATTTT TGTTTCCGTC GATGCGCGCG TGCTGGTCCG TGAGAATGGG    6000
CGCCAGCTCG TGGCGAATCT GTTCCACAAG AGGCTGCCCG TACACTTTAG AAATCGTGGC    6060
TGTCGCGGCC TTAAACCAGG ACACGTTTAG CCCATCCTTG CTGGAGACCA CAGATGGAAA    6120
GTTTGTGGTC CAAAATACGT TTTTTCGCCC CATTCTCACC ATGTACTGGT TTTCCAGTCC    6180
GTGCAGGTCC AACGTGGAGT TCCAATTTGC TATCGATACA GGAAATATGT GCCTGATTGG    6240
CAGAAAGCAT TCAGCGTAC CCATTGCGAA GAGAAAGTGC AGCATGTCCC CACTGATGTT    6300
GATGTTTATT GCGGTGCCTT GACACATGTT GTCGGAAAAA AACACGCTTA TGGTAAAAGA    6360
AGGTTCCTTT ACGGAGTACT TTCGTATAAC AAAATTGTTG GTCAATCTGG GGATGTTTAA    6420
AATAGTCTTT TGCAGGGTGT TAGGAACGTG GCAGCTTATC TTAGTGTTAA TCACCATGTT    6480
GGTGTTGAAT ATGGTGATCT TGAAGTTTTC CAAACTGACG TGTTTTGTGG GTTCCAGCAT    6540
GTCTGACACT GTAGAGCTGC CCAGAGTCCG CGCGTCCGTG GCCGCGTATC GTTGGAAGCA    6600
CGCCTGCAAA TTTCCTTTCA TGGCTGCTCG CCGGTCTTTC GGCGCGTACC GGATTCTTGA    6660
AAGCGTCGCC GCCAGGAGAC GCGGTGTCTC GTGGGTGCCT AAAAAGTTTG CGCAGGGGTG    6720
CAGTCCGCTG CACGAGTGGC CGATGCAGTC TGCCACTGCC ATACACATGA CGAGTCTGTA    6780
GATGGCCGGT GTGCCCGGAT ACACTAGATA GTAGGTACAA TCTGGGGTAC TGACGACCAC    6840
CCTGTATGGC TTTGGTCCGG GGTCCTTGCG TTGGATTTTT ACGTGCAGAC GGGACACGAG    6900
CTGGTTTAGA GCCAGCTGAA AGCCCACCAG ATCCCGTCCG TTAACCTTGA CGTCCTGGTG    6960
CTTACTCTGT TTCGACAGGT TCTTCAGCAC GGTGGGCAGT CGCTCTACGT TGTGAGCGAT    7020
GGCACGGCGC AGCGAGACCA GCTCTCCGTG CCACCCCCAC GTGGCCATGA AGCTGCTGAT    7080
GTTAAACTTT AAAAAATGTA GCTGTGCGTC TGGGGATGCG GGTGGCATTA TTGAAAACGA    7140
GAGATGCTTC AGGCTCTCCA GGAGTGCAAA ATAATTTTGA TAGATTGTGG GTTGTAGACT    7200
ATGGGGCAAC ACCGCCAGAA ACGCATGAAA ACACTGTTCG AACTCCCAGA ACTCCAGGTA    7260
CCTGCACACT ATCCTGAACA TGGCTTTGTA ACATATGGTG CACGTTAGTA GCGCGGGAAG    7320
ATACAGCGAG CGTAGCTCCC TGAATTCGCA GGGTTTATCA CAATCATCGG TAAGTTCCCA    7380
TGATCCCACC GCAGGTAGGT AGTTGTCGGT GTCTATCTGT CCGCGCGTAA ACACTCCACC    7440
```

FIG. 3A-5

```
ACCGTCAATT ATTAAACCTT CGCCGCTGTA CCGTCGACCC ACTTTTCCCA AAAGAGTCCC    7500
TTCTTGATGT ATAAAAGGGT GGAGGCGTTC CCCCAGGAGT AGTCTGCGTA TCGCTCTGCA    7560
GGCGAAAAAG GTGGGCTCGG GCTGCATCAT CTTATCAAGA CCTTCTAAGG TCAGCTCTGC    7620
CTGCAGGTGC GAGTTGGTGG CCAGACAGCA GAATATTTCC AGCTGTGATT CCCAAGTCGC    7680
TTGATAACAC GTGGTCTGCG GACTCGTCGT CAGGGAGGCG CTCGGTGGCA GTAGTAGGGG    7740
GCCCTCGAGC GCTGCCATGG AGGCGACCTT GGAGCAACGA CCTTTCCCGT ACCTCGCCAC    7800
GGAGGCCAAC CTCCTAACGC AGATTAAGGA GTCGGCTGCC GACGGACTCT TCAAGAGCTT    7860
TCAGCTATTG CTCGGCAAGG ACGCCAGAGA AGGCAGTGTC CGTTTCGAAG CGCTACTGGG    7920
CGTATATACC AATGTGGTGG AGTTTGTTAA GTTTCTGGAG ACCGCCCTCG CCGCCGCTTG    7980
CGTCAATACC GAGTTCAAGG ACCTGCGGAG AATGATAGAT GGAAAAATAC AGTTTAAAAT    8040
TTCAATGCCC ACTATTGCCC ACGGAGACGG GAGGAGGCCC AACAAGCAGA GACAGTATAT    8100
CGTCATGAAG GCTTGCAATA AGCACCACAT CGGTGCGGAG ATTGAGCTTG CGGCCGCAGA    8160
CATCGAGCTT CTCTTCGCCG AGAAAGAGAC GCCCTTGGAC TTCACAGAGT ACGCGGGTGC    8220
CATCAAGACG ATTACGTCGG CTTTGCAGTT TGGTATGGAC GCCCTAGAAC GGGGCTAGT    8280
GGACACGGTT CTCGCAGTTA AACTTCGGCA CGCTCCACCC GTCTTTATTT TAAAGACGCT    8340
GGGCGATCCC GTCTACTCTG AGAGGGGCCT CAAAAAGGCC GTCAAGTCTG ACATGGTATC    8400
CATGTTCAAG GCACACCTCA TAGAACATTC ATTTTTTCTA GATAAGGCCG AGCTCATGAC    8460
AAGGGGGAAG CAGTATGTCC TAACCATGCT CTCCGACATG CTGGCCGCGG TGTGCGAGGA    8520
TACCGTCTTT AAGGGTGTCA GCACGTACAC CACGGCCTCT GGGCAGCAGG TGGCCGGCGT    8580
CCTGGAGACG ACGGACAGCG TCATGAGACG GCTGATGAAC CTGCTGGGGC AAGTGGAAAG    8640
TGCCATGTCC GGGCCCGCGG CCTACGCCAG CTACGTTGTC AGGGGTGCCA ACCTCGTCAC    8700
CGCCGTTAGC TACGGAAGGG CGATGAGAAA CTTTGAACAG TTTATGGCAC GCATAGTGGA    8760
CCATCCCAAC GCTCTGCCGT CTGTGGAAGG TGACAAGGCC GCTCTGGCGG ACGGACACGA    8820
CGAGATTCAG AGAACCCGCA TCGCCGCCTC TCTCGTCAAG ATAGGGGATA AGTTTGTGGC    8880
CATTGAAAGT TTGCAGCGCA TGTACAACGA GACTCAGTTT CCCTGCCCAC TGAACCGGCG    8940
CATCCAGTAC ACCTATTTCT TCCCTGTTGG CCTTCACCTT CCCGTGCCCC GCTACTCGAC    9000
ATCCGTCTCA GTCAGGGGCG TAGAATCCCC GGCCATCCAG TCGACCGAGA CGTGGGTGGT    9060
TAATAAAAAC AACGTGCCTC TTTGCTTCGG TTACCAAAAC GCCCTCAAAA GCATATGCCA    9120
CCCTCGAATG CACAACCCCA CCCAGTCAGC CCAGGCACTA AACCAAGCTT TTCCCGATCC    9180
CGACGGGGGA CATGGGTACG GTCTCAGGTA TGAGCAGACG CCAAACATGA ACCTATTCAG    9240
AACGTTCCAC CAGTATTACA TGGGGAAAAA CGTGGCATTT GTTCCCGATG TGGCCCAAAA    9300
```

FIG. 3A-6

```
AGCGCTCGTA ACCACGGAGG ATCTACTGCA CCCAACCTCT CACCGTCTCC TCAGATTGGA    9360
GGTCCACCCC TTCTTTGATT TTTTTGTGCA CCCCTGTCCT GGAGCGAGAG GATCGTACCG    9420
CGCCACCCAC AGAACAATGG TTGGAAATAT ACCACAACCG CTCGCTCCAA GGGAGTTTCA    9480
GGAAAGTAGA GGGGCGCAGT TCGACGCTGT GACGAATATG ACACACGTCA TAGACCAGCT    9540
AACTATTGAC GTCATACAGG AGACGGCATT TGACCCCGCG TATCCCTGT TCTGCTATGT     9600
AATCGAAGCA ATGATTCACG GACAGGAAGA AAAATTCGTG ATGAACATGC CCCTCATTGC    9660
CCTGGTCATT CAAACCTACT GGGTCAACTC GGGAAAACTG GCGTTTGTGA ACAGTTATCA    9720
CATGGTTAGA TTCATCTGTA CGCATATTGG GAATGGAAGC ATCCCTAAGG AGGCGCACGG    9780
CCACTACCGG AAAATCTTAG GCGAGCTCAT CGCCCTTGAG CAGGCGCTTC TCAAGCTCGC    9840
GGGACACGAG ACGGTGGGTC GGACGCCGAT CACACATCTG GTTTCGGCTC TCCTCGACCC    9900
GCATCTGCTG CCTCCCTTTG CCTACCACGA TGTCTTTACG GATCTTATGC AGAAGTCATC    9960
CAGACAACCC ATAATCAAGA TCGGGGATCA AAACTACGAC AACCCTCAAA ATAGGGCGAC   10020
ATTCATCAAC CTCAGGGGTC GCATGGAGGA CCTAGTCAAT AACCTTGTTA ACATTTACCA   10080
GACAAGGGTC AATGAGGACC ATGACGAGAG ACACGTCCTG GACGTGGCGC CCCTGGACGA   10140
GAATGACTAC AACCCGGTCC TCGAGAAGCT ATTCTACTAT GTTTTAATGC CGGTGTGCAG   10200
TAACGGCCAC ATGTGCGGTA TGGGGGTCGA CTATCAAAAC GTGGCCCTGA CGCTGACTTA   10260
CAACGGCCCC GTCTTTGCGG ACGTCGTGAA CGCACAGGAT GATATTCTAC TGCACCTGGA   10320
GAACGGAACC TTGAAGGACA TTCTGCAGGC AGGCGACATA CGCCCGACGG TGGACATGAT   10380
CAGGGTGCTG TGCACCTCGT TTCTGACGTG CCCTTTCGTC ACCCAGGCCG CTCGCGTGAT   10440
CACAAAGCGG GACCCGGCCC AGAGTTTTGC CACGCACGAA TACGGGAAGG ATGTGGCGCA   10500
GACCGTGCTT GTTAATGGCT TTGGTGCGTT CGCGGTGGCG GACCGCTCTC GCGAGGCGGC   10560
GGAGACTATG TTTTATCCGG TACCCTTTAA CAAGCTCTAC GCTGACCCGT GGTGGCTGC    10620
CACACTGCAT CCGCTCCTGC CAAACTATGT CACCAGGCTC CCCAACCAGA GAAACGCGGT   10680
GGTCTTTAAC GTGCCATCCA ATCTCATGGC AGAATATGAG GAATGGCACA AGTCGCCCGT   10740
CGCGGCGTAT GCCGCGTCTT GTCAGGCCAC CCCGGGCGCC ATTAGCGCCA TGGTGAGCAT   10800
GCACCAAAAA CTATCTGCCC CCAGTTTCAT TTGCCAGGCA AAACACCGCA TGCACCCTGG   10860
TTTTGCCATG ACAGTCGTCA GGACGGACGA GGTTCTAGCA GAGCACATCC TATACTGCTC   10920
CAGGGCGTCG ACATCCATGT TTGTGGGCTT GCCTTCGGTG GTACGGCGCG AGGTACGTTC   10980
GGACGCGGTG ACTTTTGAAA TTACCCACGA GATCGCTTCC CTGCACACCG CACTTGGCTA   11040
CTCATCAGTC ATCGCCCCGG CCCACGTGGC CGCCATAACT ACAGACATGG GAGTACATTG   11100
TCAGGACCTC TTTATGATTT TCCCAGGGGA CGCGTATCAG GACCGCCAGC TGCATGACTA   11160
```

FIG. 3A-7

```
TATCAAAATG AAAGCGGGCG TGCAAACCGG CTCACCGGGA AACAGAATGG ATCACGTGGG   11220
ATACACTGCT GGGGTTCCTC GCTGCGAGAA CCTGCCCGGT TTGAGTCATG GTCAGCTGGC   11280
AACCTGCGAG ATAATTCCCA CGCCGGTCAC ATCTGACGTT GCCTATTTCC AGACCCCAG    11340
CAACCCCCGG GGGCGTGCGG CGTCGGTCGT GTCGTGTGAT GCTTACAGTA ACGAAAGCGC   11400
AGAGCGTTTG TTCTACGACC ATTCAATACC AGACCCCGCG TACGAATGCC GGTCCACCAA   11460
CAACCCGTGG GCTTCGCAGC GTGGCTCCCT CGGCGACGTG CTATACAATA TCACCTTTCG   11520
CCAGACTGCG CTGCCGGGCA TGTACAGTCC TTGTCGGCAG TTCTTCCACA AGGAAGACAT   11580
TATGCGGTAC AATAGGGGGT TGTACACTTT GGTTAATGAG TATTCTGCCA GGCTTGCTGG   11640
GGCCCCGCC ACCAGCACTA CAGACCTCCA GTACGTCGTG GTCAACGGTA CAGACGTGTT    11700
TTTGGACCAG CCTTGCCATA TGCTGCAGGA GGCCTATCCC ACGCTCGCCG CCAGCCACAG   11760
AGTTATGCTT GCCGAGTACA TGTCAAACAA GCAGACACAC GCCCAGTAC ACATGGGCCA    11820
GTATCTCATT GAAGAGGTGG CGCCGATGAA GAGACTATTA AAGCTCGGAA ACAAGGTGGT   11880
GTATTAGCTA ACCCTTCTAG CGTTGGCTAG TCATGGCACT CGACAAGAGT ATAGTGGTTA   11940
ACTTCACCTC CAGACTCTTC GCTGATGAAC TGGCCGCCCT TCAGTCAAAA ATAGGGAGCG   12000
TACTGCCGCT CGGAGATTGC CACCGTTTAC AAAATATACA GGCATTGGGC CTGGGGTGCG   12060
TATGCTCACG TGAGACATCT CCGGACTACA TCCAAATTAT GCAGTATCTA TCCAAGTGCA   12120
CACTCGCTGT CCTGGAGGAG GTTCGCCCGG ACAGCCTGCG CCTAACGCGG ATGGATCCCT   12180
CTGACAACCT TCAGATAAAA AACGTATATG CCCCCTTTTT TCAGTGGGAC AGCAACACCC   12240
AGCTAGCAGT GCTACCCCCA TTTTTTAGCC GAAAGGATTC CACCATTGTG CTCGAATCCA   12300
ACGGATTTGA CCCCGTGTTC CCCATGGTCG TGCCGCAGCA ACTGGGGCAC GCTATTCTGC   12360
AGCAGCTGTT GGTGTACCAC ATCTACTCCA AAATATCGGC CGGGGCCCCG GATGATGTAA   12420
ATATGGCGGA ACTTGATCTA TATACCACCA ATGTGTCATT TATGGGGCGC ACATATCGTC   12480
TGGACGTAGA CAACACGGAT CCACGTACTG CCCTGCGAGT GCTTGACGAT CTGTCCATGT   12540
ACCTTTGTAT CCTATCAGCC TTGGTTCCCA GGGGGTGTCT CCGTCTGCTC ACGGCGCTCG   12600
TGCGGCACGA CAGGCATCCT CTGACAGAGG TGTTTGAGGG GGTGGTGCCA GATGAGGTGA   12660
CCAGGATAGA TCTCGACCAG TTGAGCGTCC CAGATGACAT CACCAGGATG CGCGTCATGT   12720
TCTCCTATCT TCAGAGTCTC AGTTCTATAT TTAATCTTGG CCCCAGACTG CACGTGTATG   12780
CCTACTCGGC AGAGACTTTG GCGGCCTCCT GTTGGTATTC CCCACGCTAA CGATTTGAAG   12840
TGGGGGGGT ATGGCGTCAT CTGATATTCT GTCGGTTGCA AGGACGGATG ACGGCTCCGT    12900
CTGTGAAGTC TCCCTGCGTG GAGGTAGGAA AAAACTACC GTCTACCTGC CGGACACTGA    12960
ACCCTGGGTG GTAGAGACCG ACGCCATCAA AGACGCCTTC CTCAGCGACG GGATCGTGGA   13020
```

FIG. 3A-8

```
TATGGCTCGA AAGCTTCATC GTGGTGCCCT GCCCTCAAAT TCTCACAACG GCTTGAGGAT    13080
GGTGCTTTTT TGTTATTGTT ACTTGCAAAA TTGTGTGTAC CTAGCCCTGT TTCTGTGCCC    13140
CCTTAATCCT TACTTGGTAA CTCCCTCAAG CATTGAGTTT GCCGAGCCCG TTGTGGCACC    13200
TGAGGTGCTC TTCCCACACC CGGCTGAGAT GTCTCGCGGT TGCGATGACG CGATTTTCTG    13260
TAAACTGCCC TATACCGTGC CTATAATCAA CACCACGTTT GGACGCATTT ACCCGAACTC    13320
TACACGCGAG CCGGACGGCA GGCCTACGGA TTACTCCATG GCCCTTAGAA GGGCTTTTGC    13380
AGTTATGGTT AACACGTCAT GTGCAGGAGT GACATTGTGC CGCGGAGAAA CTCAGACCGC    13440
ATCCCGTAAC CACACTGAGT GGGAAAATCT GCTGGCTATG TTTTCTGTGA TTATCTATGC    13500
CTTAGATCAC AACTGTCACC GGAAGCACT GTCTATCGCG AGCGGCATCT TTGACGAGCG    13560
TGACTATGGA TTATTCATCT CTCAGCCCCG GAGCGTGCCC TCGCCTACCC CTTGCGACGT    13620
GTCGTGGGAA GATATCTACA ACGGGACTTA CCTAGCTCGG CCTGGAAACT GTGACCCCTG    13680
GCCCAATCTA TCCACCCCTC CCTTGATTCT AAATTTTAAA TAAAGGTGTG TCACTGGTTA    13740
CACCACGATT AAAAACCACT CACTGAGATG TCTTTTTAAC CGCTAAGGGA TTATACCGGG    13800
ATTTAAAACC GCCCACTGAT TTTTTTACGC TAAGAGTTGG GTGCTTGGGG GGTTTTGCAT    13860
TGCTCTGTTG TAAACTATAT ATAAGTTAAA CCAAAATTCG CAGGGAGACA AGGTGACGGT    13920
GGTGAGAACT CAGTTGAGAG TCAGAGAATA CAGTGCTAAT CAGGGTAGAT GAGCATGACT    13980
TTCCCCGTCT CCAGTCACCG GAGGAATGGT GGACGGCTCC GTCCTGGTGC GAATGGCCAC    14040
CAAGCCTCCC GTGATTGGTC TTATAACAGT GCTCTTCCTC CTAGTCATAG GCGCCTGCGT    14100
CTACTGCTGC ATTCGCGTGT TCCTGGCGGC TCGACTGTGG CGCGCCACCC CACTAGGCAG    14160
GGCCACCGTG GCGTATCAGG TCCTTCGCAC CCTGGGACCG CAGGCCGGGT CACATGCACC    14220
GCCGACGGTG GGCATAGCTA CCCAGGAGCC CTACCGTACA ATATACATGC CAGATTAGAA    14280
CGGGGTGTGT GCTATAATGG ATGGCTATGG GGGGGGGCTG TAGATAATTG AGCGCTGTGC    14340
TTTTATTGTG GGGATATGGG CTTGTACATG TGTCTATCAT CGGTAGCCAT AAAATGGGCC    14400
ATGACAACTG CCACAAGTAA GTCGTCCGAC ATGTGCTTTT GCTTGGCGCT GTATGACTGC    14460
CCTCCATCCC TAAGCGGGAC GCACTTGATC GCGCGGACCT GTTCTACCAG GTAGGTCACC    14520
GGGTCAAATG ATATTTTGAT GGTGTTGGAC ACCACCGTCT GGCTGGCGCT CAGGGTGCCG    14580
GAGTTCAGAG CGTAGATGAA TGTCTCAAAC GCGGAGGATT CTCGCCTCC CAACATGTAA    14640
ATTGGCCACT GCAGGGCGCT GCTCTTGTCA GTATAGTGTA GAAATGTAT GGGGAGCGGG    14700
CATATTTCGT TAAGGACGGT TGCAATGGCC ACCCCAGAAT CTTGGCTGCT GTTGCCTTCG    14760
ACCGCCGCGT TCACGCGCTC AATTGTGGTG TGGAGCACAG CGATCGCCTT AATCATCGTG    14820
CATGCGCAGG ACGCTATCTC GTAAGCAGCT GCGCCAGTGA GGTCGCGCAG GAAGAAATGC    14880
TCCATGCCCA ATATGAGGCT TCTGGTGGGA GTCTGAGTAC TCGTGACAAC GGCGCCCACG    14940
CCAGTACCGG ACGCCTCCGT GTTGTTCGTA TACGCGGGGT CGATGTAAAC AAACAGCTGT    15000
```

FIG. 3A-9

```
TTTCCAAGGC ACTTCTGAAC CTCCTGGGCG GTGGTGTCTA CCCGACACAT GTCAAACTGT   15060
GTCAGCGCTG CGTCACCCAC CACGCGGTAA AGCGTAGCAT TTGACGACGC TGCTCCCTCG   15120
CCCATTAGTT CGGTGTCGAA TGCCCCCTCC ATAAAGAGGT TGGTGGTGGT TTTGATGGAT   15180
TCGTCGATGG TGATGTACGT CGGAATGTGC AGTCTGTAAC AAGGACAGGA CACTAGTGCG   15240
TCTTGCAGGT GGAAATCTTC TCGGTGGTCC GCACACACGT AACTGACCAC ATTCAGCATC   15300
TTTTCCTGGG CGTTCCTGAG GTTAAGCAGG AAACTCGTGG AGCGGTCTGA CGAGTTCACG   15360
GATGATATAA ATATAAGCTT GGCGTCTTTC TGAAGCATGA AACCCAGAAT AGCCGGCAGT   15420
GCATCCTTTT TAATAAAATT CGCCTCGTCT ACGTAGAGCA GGTTAAAGGT CTGTCCCCGA   15480
ATGCTCTGCA GACACGGAAA GACACAAAAG AGGGGCTCAT AAGCGGCTAA CAGTAAAGGA   15540
GAGGAGGCGA ACAGTGCGTG GCTCTTGGTT CTTGGGAATA AAAGGGGGCG TGTGTGCCGA   15600
TCGATCGTAT GGGTGAGCCA GTGGATCCTG GACATGTGGT GAATGAGAAA GATTTTGAGG   15660
AGTGTGAACA ATTTTTCAGT CAACCCCTTA GGGAGCAAGT GGTCGCGGGG GTCAGGGCAC   15720
TCGACGGCCT CGGTCTCGCT GACTCTCTAT GTCACAAAAC AGAAAGACTC TGCCTGCTGA   15780
TGGACCTGGT GGGCACGGAG TGCTTTGCGA GGGTGTGCCG CCTAGACACC GGTGCGAAAT   15840
GAAGAGTGTG GCGAGTCCCT TATGTCAGTT CCACGGCGTG TTTTGCCTGT ACCAGTGTCG   15900
CCAGTGCCTG GCATACCACG TGTGTGATGG GGGCGCCGAA TGCGTTCTCC TGCATACGCC   15960
GGAGAGCGTC ATCTGCGAAC TAACGGGTAA CTGCATGCTC GGCAACATTC AAGAGGGCCA   16020
GTTTTTAGGG CCGGTACCGT ATCGGACTTT GGATAACCAG GTTGACAGGG ACGCATATCA   16080
TGGGATGCTA GCGTGTCTGA AACGGGACAT TGTGCGGTAT TTGCAGACAT GGCCGGACAC   16140
CACCGTAATC GTGCAGGAAA TAGCCCTGGG GACGGCGTC ACCGACACCA TCTCGGCCAT   16200
TATAGATGAA ACATTCGGTG AGTGTCTTCC CGTACTGGGG GAGGCCCAAG GCGGGTACGC   16260
CCTGGTCTGT AGCATGTATC TGCACGTTAT CGTCTCCATC TATTCGACAA AAACGGTGTA   16320
CAACAGTATG CTATTTAAAT GCACAAAGAA TAAAAAGTAC GACTGCATTG CCAAGCGGGT   16380
GCGGACAAAA TGGATGCGCA TGCTATCAAC GAAAGATACG TAGGTCCTCG CTGCCACCGT   16440
TTGGCCCACG TGGTGCTGCC TAGGACCTTT CTGCTGCATC ACGCCATACC CCTGGAGCCC   16500
GAGATCATCT TTTCCACCTA CACCCGGTTC AGCCGGTCGC CAGGGTCATC CCGCCGGTTG   16560
GTGGTGTGTG GGAAACGTGT CCTGCCAGGG GAGGAAAACC AACTTGCGTC TTCACCTTCT   16620
GGTTTGGCGC TTAGCCTGCC TCTGTTTTCC CACGATGGGA ACTTTCATCC ATTTGACATC   16680
TCGGTACTGC GCATTTCCTG CCCTGGTTCT AATCTTAGTC TTACTGTCAG ATTTCTCTAT   16740
CTATCTCTGG TGGTGGCTAT GGGGGCGGGA CGGAATAATG CGCGGAGTCC GACCGTTGAC   16800
GGGTATCGC CGCCAGAGGG CGCCGTAGCC CACCCTTTGG AGGAACTGCA GAGGCTGGCG    16860
GTGCTACGC CGGACCCGGC ACTCACCCGT GGACCGTTGC AGGTCCTGAC CGGCCTTCTC    16920
GCGCAGGGT CAGACGGAGA CCGCGCCACT CACCACATGG CGCTCGAGGC TCCGGGAACC    16980
```

FIG. 3A-10

```
GTGCGTGGAG AAAGCCTAGA CCCGCCTGTT TCACAGAAGG GGCCAGCGCG CACACGCCAC   17040
AGGCCACCCC CCGTGCGACT GAGCTTCAAC CCCGTCAATG CCGATGTACC CGCTACCTGG   17100
CGAGACGCCA CTAACGTGTA CTCGGGTGCT CCCTACTATG TGTGTGTTTA CGAACGCGGT   17160
GGCCGTCAGG AAGACGACTG GCTGCCGATA CCACTGAGCT TCCCAGAAGA GCCCGTGCCC   17220
CCGCCACCGG GCTTAGTGTT CATGGACGAC TTGTTCATTA ACACGAAGCA GTGCGACTTT   17280
GTGGACACGC TAGAGGCCGC CTGTCGCACG CAAGGCTACA CGTTGAGACA GCGCGTGCCT   17340
GTCGCCATTC CTCGCGACGC GGAAATCGCA GACGCAGTTA ATCGCACTT TTTAGAGGCG    17400
TGCCTAGTGT TACGGGGGCT GGCTTCGGAG GCTAGTGCCT GGATAAGAGC TGCCACGTCC   17460
CCGCCCCTTG GCCGCCACGC CTGCTGGATG GACGTGTTAG GATTATGGGA AAGCCGCCCC   17520
CACACTCTAG GTTTGGAGTT ACGCGGCGTA AACTGTGGCG GCACGGACGG TGACTGGTTA   17580
GAGATTTTAA AACAGCCCGA TGTGCAAAAG ACAGTCAGCG GGAGTCTTGT GGCATGCGTG   17640
ATCGTCACAC CCGCATTGGA AGCCTGGCTT GTGTTACCTG GGGGTTTTGC TATTAAAGCC   17700
CGCTATAGGG CGTCGAAGGA GGATCTGGTG TTCATTCGAG GCCGCTATGG CTAGCCGGAG   17760
GCGCAAACTT CGGAATTTCC TAAACAAGGA ATGCATATGG ACTGTTAACC CAATGTCAGG   17820
GGACCATATC AAGGTCTTTA ACGCCTGCAC CTCTATCTCG CCGGTGTATG ACCCTGAGCT   17880
GGTAACCAGC TACGCACTGA GCGTGCCTGC TTACAATGTG TCTGTGGCTA TCTTGCTGCA   17940
TAAAGTCATG GGACCGTGTG TGGCTGTGGG AATTAACGGA GAAATGATCA TGTACGTCGT   18000
AAGCCAGTGT GTTTCTGTGC GGCCCGTCCC GGGGCGCGAT GGTATGGCGC TCATCTACTT   18060
TGGACAGTTT CTGGAGGAAG CATCCGGACT GAGATTTCCC TACATTGCTC CGCCGCCGTC   18120
GCGCGAACAC GTACCTGACC TGACCAGACA AGAATTAGTT CATACCTCCC AGGTGGTGCG   18180
CCGCGGCGAC CTGACCAATT GCACTATGGG TCTCGAATTC AGGAATGTGA ACCCTTTTGT   18240
TTGGCTCGGG GGCGGATCGG TGTGGCTGCT GTTCTTGGGC GTGGACTACA TGGCGTTCTG   18300
TCCGGGTGTC GACGGAATGC CGTCGTTGGC AAGAGTGGCC GCCCTGCTTA CCAGGTGCGA   18360
CCACCCAGAC TGTGTCCACT GCCATGGACT CCGTGGACAC GTTAATGTAT TTCGTGGGTA   18420
CTGTTCTGCG CAGTCGCCGG GTCTATCTAA CATCTGTCCC TGTATCAAAT CATGTGGGAC   18480
CGGGAATGGA GTGACTAGGG TCACTGGAAA CAGAAATTTT CTGGGTCTTC TGTTCGATCC   18540
CATTGTCCAG AGCAGGGTAA CAGCTCTGAA GATAACTAGC CACCCAACCC CCACGCACGT   18600
CGAGAATGTG CTAACAGGAG TGCTCGACGA CGGCACCTTG GTGCCGTCCG TCCAAGGCAC   18660
CCTGGGTCCT CTTACGAATG TCTGACTACT TCAGCCGCTT GCTGATATAT GAGTGTAAAA   18720
AACTTAAGGC CCTGGGCTTA CGTTCTTATT GAAGCATGTT GCGCACATCA GCGAGCTGGA   18780
CCGTCCTCCG GGTCGCGTGT AGATTATGGT TCCGTTCTCC TTCTTGATGT TTAAATTTTT   18840
```

FIG. 3A-11

```
GGGGGGGAAC CACCGACAAA GCGTCTTTAT GATTTCCGCG AACACGGAGT TGGCTACGTG    18900
CTTTTGGTGG GCTACGTACC CAATGTTAAT GTTCTCTACG GATGCCAGTA GCATGCTGAT    18960
GATCGCCACC ACTATCCATG TCTTTCCGTG TCTCCTTGGT ATTAGGAATA CGCTTGCCTT    19020
TTGCTTAAAC GTCTGTAAAA CACTGTTTGG AGTTTCAAAT AAACCGAAGT ACTGCTTAAA    19080
CAATCCAAAC AACTGGTGCG TCTTTTGTGG GGCCTTGATT GAAACCAAAA AGAAAAAAGT    19140
GTGCATTACT AGCTGCTGTT GGAAGGGCTC CAGCCAGTGC ACCCCGGGAA CGTAACAGCC    19200
GTTCAGAAAG GACGAAAGGT TAACCAGAAA AGCCTGAAGT TCGCGGTAGA CAGAGCAGGC    19260
GTGCAGGGAG TCGTGTGTTT TTCTGCCCGC CTGGTACTCG ACCAGTTGAT CGGCCGTGGA    19320
GACGTGCGCG TCCTCGCGCA CACACCGCAT CTGCAAGTAT GTTGATAGGG ACTCCAATAG    19380
GCGCGGCTTT GCGGGGACGT TGTCCTCGGA CGGTCTGGGG GTTCCACGT CGGGATTTGC     19440
TGACGTGGGC GTGGCGGGAT GGTGCCGTGT GCAGTATGTT CCAGGACCG AACTGTATGA     19500
GTTTATTCTG TGCACCACGC CAATAAAAGG GTGCGCCATC CGTGCCGTTT TGGGACAGTG    19560
TCGCGTGAAT GTCGGGGCAC TCAGTTCCCA CCTCTCTCCG GCGTCTTTGG CGGTCTCCTC    19620
CAGGTTGGCG GCAAGGCGCT CCCTGTGACG GCTGAGCAGC ATGTTTGCTT TGAGCTCGCT    19680
CGTGTCCGAG GGTGACCCGG AGGTGACCAG TAGGTACGTC AAGGGCGTAC AACTTGCCCT    19740
GGACCTTAGC GAGAACACAC CTGGACAATT TAAGTTGATA GAAACTCCCC TGAACAGCTT    19800
CCTCTTGGTT TCCAACGTGA TGCCCGAGGT CCAGCCAATC TGCAGTGGCC GGCCGGCCTT    19860
GCGGCCAGAC TTTAGTAATC TCCACTTGCC TAGACTGGAG AAGCTCCAGA GAGTCCTCGG    19920
GCAGGGTTTC GGGGCGGCGG GTGAGGAAAT CGCACTGGAC CCGTCTCACG TAGAAACACA    19980
CGAAAAGGGC CAGGTGTTCT ACAACCACTA TGCTACCGAG GAGTGGACGT GGGCTTTGAC    20040
TCTGAATAAG GATGCGCTCC TTCGGGAGGC TGTAGATGGC CTGTGTGACC CCGGAACTTG    20100
GAAGGGTCTT CTTCCTGACG ACCCCCTTCC GTTGCTATGG CTGCTGTTCA ACGGACCCGC    20160
CTCTTTTTGT CGGGCCGACT GTTGCCTGTA CAAGCAGCAC TGCGGTTACC CGGGCCCGGT    20220
GCTACTTCCA GGTCACATGT ACGCTCCCAA ACGGGATCTT TTGTCGTTCG TTAATCATGC    20280
CCTGAAGTAC ACCAAGTTTC TATACGGAGA TTTTTCCGGG ACATGGGCGG CGGCTTGCCG    20340
CCCGCCATTC GCTACTTCTC GGATACAAAG GGTAGTGAGT CAGATGAAAA TCATAGATGC    20400
TTCCGACACT TACATTTCCC ACACCTGCCT CTTGTGTCAC ATATATCAGC AAAATAGCAT    20460
AATTGCGGGT CAGGGGACCC ACGTGGGTGG AATCCTACTG TTGAGTGGAA AAGGGACCCA    20520
GTATATAACA GGCAATGTTC AGACCCAAAG GTGTCCAACT ACGGGCGACT ATCTAATCAT    20580
CCCATCGTAT GACATACCGG CGATCATCAC CATGATCAAG GAGAATGGAC TCAACCAACT    20640
CTAAAAGAGA GTTTATTAAG TCGGCTCTGG AGGCCAACAT CAACAGGAGG GCAGCTGTAT    20700
CGCTATTTGA                                                          20710
```

FIG. 3B

SEQ. I.D. NO. 36

```
GGATCCCTCT GACAACCTTC AGATAAAAAA CGTATATGCC CCCTTTTTTC AGTGGGACAG    60
CAACACCCAG CTAGCAGTGC TACCCCCATT TTTTAGCCGA AAGGATTCCA CCATTGTGCT   120
CGAATCCAAC GGATTTGACC CCGTGTTCCC CATGGTCGTG CCGCAGCAAC TGGGGCACGC   180
TATTCTGCAG CAGCTGTTGG TGTACCACAT CTACTCCAAA ATATCGGCCG GGGCCCCGGA   240
TGATGTAAAT ATGGCGGAAC TTGATCTATA TACCACCAAT GTGTCATTTA TGGGGCGCAC   300
ATATCGTCTG GACGTAGACA ACACGGATCC                                    330
```

FIG. 3C

SEQ. I.D. NO. 37

```
GGATCCGCTG GCAGGTGGGC GCGCACCTCG TCGGGTAGCT TGGAGACAAA CAGCTCCAGG    60
CCAGTCCGCG CCGTAGCGCC TGCAGGTGCC TCACCACCGG GGCCGGGTCA TGCGATCTGT   120
TTAGTCCGGA GAAGATAGGG CCCTTGGGAA GCCGCTGAAC CAGCTCCAGG GTCTCCAAGA   180
TGCGCACCGG TTGTCGGAGC TGTCGCGATA GAGGTTAGGG TAGGTGTCCG GTCCGTCCGT   240
GGGCTCAAAC CTGCCCAGAC ACACCACTGT CTGCTGGGGG ATCATCCTTC TCAGGGAGAT   300
GCATTCTTTG GAAGTAGTGG TAGAGATGGA GCAGACTGCC AGGGCGTTGC AGGAGTGGTG   360
GCGATGGTGC GCACCGTTTT TAAGAAACCC CCCAGGGTGG GGACTCCCGC TCCCTGCAGC   420
ATCTCGGCCT GCTGTACGTC CTTGGCGAAT ATGCGACGAA ATCGGCTGTG CGCACGGGGT   480
CCCAGGGCCG GTCCGGTGGC ATACAGGCCG GTGAGGGCCC CCTGGGTCTG TCCGCCTGGA   540
AACAGGGTGC TGTGAAACAA CAGGTTGCAA GGCCGCGAAT ACCCCTCTGC ACGCTGCTGT   600
GGACGTGGGT GTATGCTCCG TGGATCC                                      627
```

FIG. 3D
SEQ. I.D. NO. 38

```
AGCCGAAAGG ATTCCACCAT TGTGCTCGAA TCCAACGGAT TTGACCCCGT GTTCCCCATG    60
GTCGTGCCGC AGCAACTGGG GCACGCTATT CTGCAGCAGC TGTTGGTGTA CCACATCTAC   120
TCCAAAATAT CGGCCCGGGGC CCCGGATGAT GTAAATATGG CGGAACTTGA TCTATATACC   180
ACCAATGTGT CATTTATGGG GCGCACATAT CGTCTGGACG TAGACAACAC GGA          233
```

FIG. 3E

SEQ. I.D. NO. 39

```
GAAATTACCC ACGAGATCGC TTCCCTGCAC ACCGCACTTG GCTACTCATC AGTCATCGCC    60
CCGGCCCACG TGGCCCGCCAT AACTACAGAC ATGGGAGTAC ATTGTCAGGA CCTCTTTATG   120
ATTTTCCCAG GGGACGCGTA TCAGGACCGC CAGCTGCATG ACTATATCAA AATGAAAGCG   180
GGCGTGCAAA CCGGCTCACC GGGAAACAGA ATGGATCACG TGGGATACAC TGCTGGGGTT   240
CCTCGCTGCG AGAACCTGCC CGGTTTGAGT CATGGTCAGC TGGCAACCTG CGAGATAATT   300
CCCACGCCGG TCACATCTGA CGTTGCCT                                      328
```

FIG. 3F

SEQ. I.D. NO. 40

```
AACACGTCAT GTGCAGGAGT GACATTGTGC CGCGGAGAAA CTCAGACCGC ATCCCGTAAC    60
CACACTGAGT GGGAAAATCT GCTGGCTATG TTTTCTGTGA TTATCTATGC CTTAGATCAC   120
AACTGTCACC CG                                                      132
```

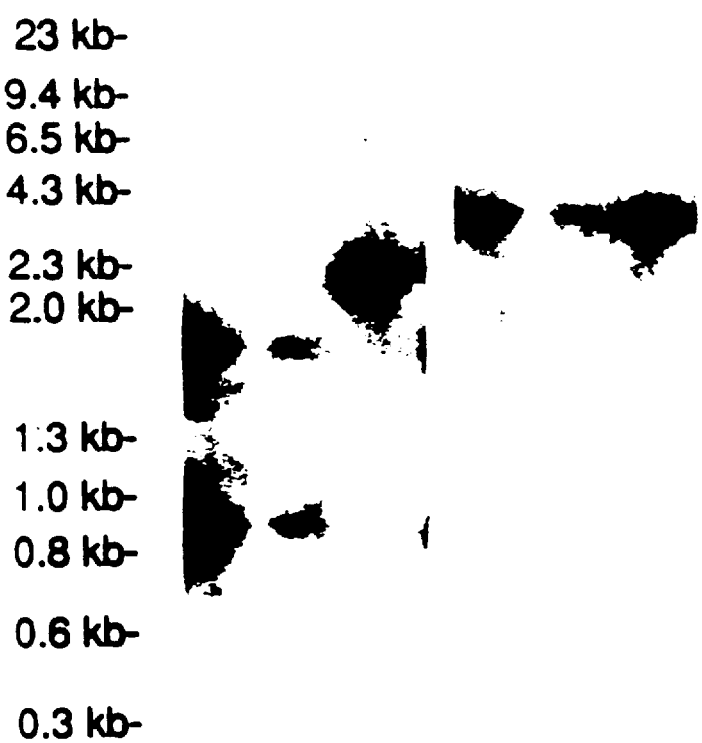

FIG. 6

```
              1
HSVSA  MLTDKTIIVS  LTSRLFADEI  TKLQKKIGSI  LPLQDPHKLQ  SLDTLGLNAV
   KS  MALDKSIVVN  FTSRLFADEL  AALQSKIGSV  LPLGDCHRLQ  NIQALGLGCV       50
  EBV  ..MDLKVVVS  LSSRLYTDEI  AKMQQRIGCI  LPLASTHGTQ  NVQGLGLGQV

51
HSVSA  CSRDVFPDYV  HMFSYLSKCT  LAILEEVNPD  NLILTRLDPS  ETYQIKNVYE
   KS  CSRETSPDYI  QIMQYLSKCT  LAVLEEVRPD  SLRLTRMDPS  DNLQIKNVYA      100
  EBV  YSLETVPDYV  SMYNYLSDCT  LAVLDEVSVD  SLILTKIVPG   QTYAIKNKYQ

101
HSVSA  PMFQWDGFSN  LTVIPPVFGR  QQATVTLESN  GFDLVFPSVV  PSDLAQAIIG
   KS  PFFQWDSNTQ  LAVLPFFSR   KDSTIVLESN  GFDPVFPMVV  PQQLGHAILQ      150
  EBV  PFFQWHGTGS  LSVMPPVFGR  EHATVKLESN  DVDIVFPMVL  PTPIAEEVLQ

151
HSVSA  KILLYNLYSR  LVESDP.EIN  IEEVNMYTTN  VTHMGRHYVL  DINHNNFNEA
   KS  QLLVMHIYSK  ISAGAPDDVN  MAELDLYTTN  VSFMGRTYRL  DVDNTDPRTA      200
  EBV  KILLFNVYSR  VVMQAPGNAD  EHATVKLESN  VSYLGHHMEL  ALPEVPGPLG

201
HSVSA  LKSLDDLAVY  TCILSALIPR  ACLRMTILM   RHDQHELLDV  FRGIVPREVY
   KS  LRVLDDLSMY  LGILSALVPR  GCLRLLTALV  RHDRHPLTEV  FEGVVPDEVT      250
  EBV  LALDNLSLY   FCIMVTLLPR  ASMRLVRGLI  RHEHHDLLNL  FQEMVPDEIA

251
HSVSA  EIDANALSIG  DDITRMTTFI  TYLQSLSSIF  NLGAKLHLSS  MASETQTATC
   KS  RIDLDQLSVP  DDITRMRVMF  SYLQSLSSIF  NLGPRLHVYA  YSAETLAASC     300
  EBV  RIDLDDLSVA  DDLSRMRVMM  TYLQSLASLF  NLGPRLATAA  YSQETLTATC

301
HSVSA  WISYC
   KS  WYSPR
  EBV  WLR
```

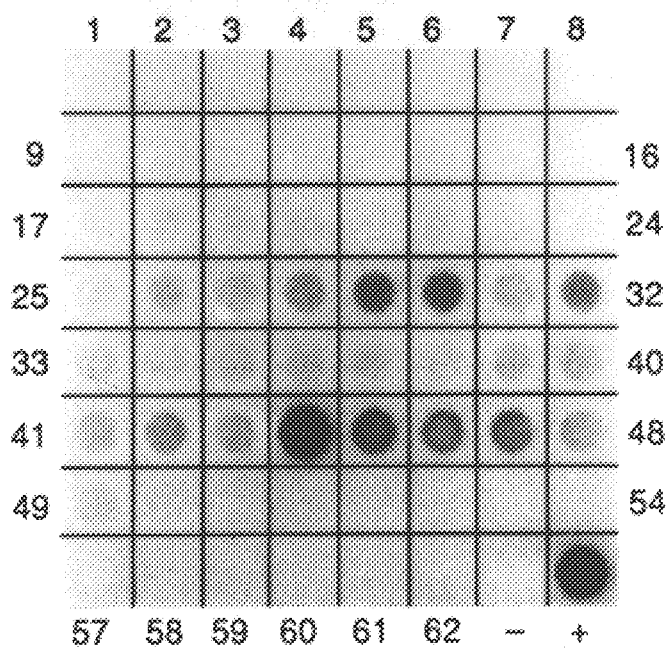

FIG. 12

| KSHV ORF | Start | ATG | Stop | aa | TATA | polyA |
|---|---|---|---|---|---|---|
| ORF20* | 20090 | 20153 |  | 184 |  |  |
| ORF21 | 20436 | 20343 | 18601 | 580 |  | 18684 |
| ORF22 | 18631 | 18613 | 16421 | 730 | 18685 | 16414 |
| ORF23 | 15206 | 15210 | 16422 | 403 | 14955 | 16422 |
| ORF24 | 12843 | 12948 | 15206 | 752 | 11641 | 16422 |
| ORF25 | 13021 | 12949 | 8819 | 1376 | 13256 | 8849 |
| ORF26 | 8808 | 8793 | 7876 | 305 | 13256 | 6987 |
| ORF27 | 7870 | 7855 | 6983 | 290 | 7419 | 6987 |
| ORF28 | 6740 | 6737 | 6367 | 120 | 6830 | 5274 |
| ORF29b | 5029 |  | 6363 | 430 | 4507 | 6359 |
| ORF30 | 5186 | 5102 | 4869 | 77 | 5340 | 4362 |
| ORF31 | 4971 | 4962 | 4288 | 224 | 5340 | 4362 |
| ORF32 | 4360 | 4319 | 2957 | 454 | 5340 | 3019 |
| ORF33 | 3072 | 2964 | 2028 | 312 | 3020 | 1653 |
| ORF29a | 743 | 1049 | 1987 | 312 |  |  |
| ORF34 | 1065 | 1050 | 69 | 327 | 3020 |  |
| ORF35* |  |  | 138 | 45 |  | 54 |

Gene Homologs

| HVS ORF | %I, %S | EHV-2 ORF | %I, %S | EBV ORF | %I, %S | F |
|---|---|---|---|---|---|---|
| ORF20 |  | ORF20 |  | BXRF1 |  |  |
| ORF21 | 32%,50% | ORF21 | 31%,51% | BXLF1 | 28%,50% | TK |
| ORF22 | 35%,55% | ORF22 | 31%,52% | BXLF2 | 26%,48% | gH |
| ORF23 | 33%,57% | ORF23 | 34%,56% | BTRF1 | 31%,51% |  |
| ORF24 | 45%,66% | ORF24 | 41%,58% | BCRF1 | 38%,57% |  |
| ORF25 | 65%,81% | ORF25 | 63%,79% | BCLF1 | 56%,75% | MCP |
| ORF26 | 58%,76% | ORF26 | 46%,70% | BDLF1 | 49%,73% | VP23 |
| ORF27 | 29%,49% | ORF27 | 20%,44% | BDLF2 | 19%,43% |  |
| --- |  | --- |  | --- |  |  |
| ORF29b | 64%,83% | ORF29b | 68%,82% | BDRF1 | 60%,76% | SG |
| ORF30 | 33%,55% | ORF30 | 38%,56% | BDLF3.5 | 30%,53% |  |
| ORF31 | 43%,63% | ORF31 | 38%,64% | BDLF4 | 36%,58% |  |
| ORF32 | 30%,52% | ORF32 | 32%,51% | BGLF1 | 27%,47% |  |
| ORF33 | 36%,58% | ORF33 | 33%,56% | BGLF2 | 32%,52% |  |
| ORF29a | 53%,68% | ORF29a | 52%,68% | BGRF1 | 41%,57% | SG |
| ORF34 | 42%,59% | ORF34 | 29%,60% | BGLF3 | 33%,55% |  |
| ORF35 |  | ORF35 |  | BGLF3.5 |  |  |

The nomenclature used for KSHV ORFs is relative to the HVS ORF nomenclature.
*, incomplete ORFs; S, strand (C, complementary); TATA; location of upstream TATA elements (TATTAA, TATAAA, TATAAT); polyadenylation signal, (AATAAA, ATTAAA); %I, percentage of aligned amino acid identity; %S, percentage of aligned similar amino acids; F, function; TK, thymidine kinase; gH, glycoprotein H; MCP, major capsid protein; VP23, virion protein; SG, putative DNA packaging spliced gene.

FIG. 13

| Patient no. AIDS-KS Cases | HIV Risk Group* | Non-absorbed HBL-6 | P3H3 | P3H3-absorbed HBL-6 | P3H3 |
|---|---|---|---|---|---|
| 1 | H/B | 4050 | 1350 | 4050 | 50 |
| 2 | H/B | 450 | 50 | 450 | 50 |
| 3 | H/B | 450 | 450 | 450 | 50 |
| 4 | H/B | 450 | 450 | 150 | <50 |
| 5 | H/B | 4050 | 1350 | 1350 | 150 |
| 6 | H/B | 4050 | 1350 | 450 | 50 |
| 7 | H/B | 12,150 | 450 | 12,150 | 150 |
| 8 | H/B | 1350 | 1350 | 1350 | 150 |
| 9 | H/B | 1350 | 450 | 1350 | 50 |
| 10 | H/B | 150 | 150 | 150 | <50 |
| 11 | H/B | 150 | 450 | 50 | <50 |
| 12 | H/B | 450 | 450 | 450 | 50 |
| 13 | H/B | 1350 | 450 | 1350 | 50 |
| 14 | H/B | 4050 | 1350 | 4050 | 50 |
| GMT | | 1153 | 526 | 780 | 63 |
| HIV/AIDS Controls | | | | | |
| 1 | H/B | 150 | 150 | 50 | 50 |
| 2 | H/B | 150 | 150 | 50 | 50 |
| 3 | H/B | 12,150 | 4050 | 150 | 150 |
| 4 | H/B | 1350 | 4050 | 150 | 150 |
| 5 | H/B | 4050 | 4050 | 450 | 450 |
| 6 | IVDU-F | 1350 | 1350 | 150 | 150 |
| 7 | IVDU-F | 12,150 | 12,150 | 450 | 450 |
| 8 | Hemo | 50 | 150 | <50 | <50 |
| 9 | Hemo | 50 | 50 | <50 | <50 |
| 10 | Hemo | 150 | 150 | <50 | <50 |
| 11 | Hemo | 450 | 1350 | 50 | 150 |
| 12 | Hemo | 150 | 450 | 50 | 50 |
| 13 | Hemo | 50 | 50 | <50 | <50 |
| 14 | Hemo | 50 | <50 | <50 | <50 |
| 15 | Hemo | 150 | 450 | 50 | 50 |
| 16 | Hemo | 150 | 150 | 50 | 50 |
| GMT | | 342 | 450 | 81 | 87 |
| Kruskall-Wallace H value** | | 4.3 | 0.31 | 15.4 | 1.2 |
| p value** | | 0.04 | 0.6 | 0.00009 | 0.30 |

*H/B=Homosexual/bisexual males, IVDU-F=Female intravenous drug user, Hemo=hemophiliac male.
**Comparison between log titers for case and control sera.

FIG. 21

| | Initial Sample | Second Sample |
|---|---|---|
| AIDS-KS, n=21 | | |
| Months prior to or after AIDS-KS | | |
| median (range) | -13 (-87 to -4) | +1 (-6 to +20) |
| CD4+ count, mm³ | | |
| median (range) | 432 (63 to 866) | 124 (8 to 640) |
| KSHV positivity | | |
| no. (%) | 9 (43%) | 12 (57%) |
| Gay/Bisexual AIDS without KS, n=23 | | |
| Months prior to AIDS diagnosis | | |
| median (range) | -55 (-106 to -13) | -5 (-8 to -0) |
| CD4+ count, mm³ | | |
| median (range) | 612 (333 to 1309) | 215 (11 to 598) |
| KSHV positivity | | |
| no. (%) | 1 (4%) | 2 (9%) |
| Hemophilic AIDS without KS, n=19 | | |
| CD4+ count, mm³* | | |
| median (range) | 344 (83 to 559) | |
| KSHV positivity | | |
| no. (%) | 2 (11%) | |

*CD4+ counts available for 15 hemophilic patients at or prior to sample collection date.

FIG. 22

PCR analysis of $KS330_{233}$ in DNA samples from patients with Kaposi's sarcoma and tumor controls

|  | No. tested | KS $KS330_{233}$ positive (%) |
|---|---|---|
| KS tissue: |  |  |
| AIDS-KS | 24 | 22 (92) |
| Endemic KS | 20 | 17 (85) |
| Total | 44 | 39 (89) |
| Control Tumors: |  |  |
| HIV seropositive | 7 | 1 (14) |
| HIV seronegative | 15 | 2 (13) |
| Total | 22 | 3 (14) |

FIG. 23  KSHV LONG UNIQUE CODING REGION

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 615 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..615

( x ) SEQUENCE DESCRIPTION: SEQ ID NO:1:

```
ATG  TGC  TGG  TTC  AAG  TTG  TGG  TCT  CTC  TTG  CTG  GTC  GGT  TCA  CTG  CTG         48
Met  Cys  Trp  Phe  Lys  Leu  Trp  Ser  Leu  Leu  Leu  Val  Gly  Ser  Leu  Leu
 1              5                        10                       15

GTA  TCT  GGA  ACG  CGG  GGC  AAG  TTG  CCG  GAC  GCC  CCC  GAG  TTT  GAA  AAG         96
Val  Ser  Gly  Thr  Arg  Gly  Lys  Leu  Pro  Asp  Ala  Pro  Glu  Phe  Glu  Lys
                20                       25                       30

GAT  CTT  CTC  ATT  CAG  AGA  CTC  AAT  TGG  ATG  CTA  TGG  GTG  ATC  GAT  GAA        144
Asp  Leu  Leu  Ile  Gln  Arg  Leu  Asn  Trp  Met  Leu  Trp  Val  Ile  Asp  Glu
                35                       40                       45

TGC  TTC  CGC  GAC  CTC  TGT  TAC  CGT  ACC  GGC  ATC  TGC  AAG  GGT  ATT  CTA        192
Cys  Phe  Arg  Asp  Leu  Cys  Tyr  Arg  Thr  Gly  Ile  Cys  Lys  Gly  Ile  Leu
      50                       55                       60

GAG  CCC  GCT  GCT  ATT  TTT  CAT  CTG  AAA  CTA  CCA  GCC  ATC  AAC  GAT  ACT        240
Glu  Pro  Ala  Ala  Ile  Phe  His  Leu  Lys  Leu  Pro  Ala  Ile  Asn  Asp  Thr
 65                       70                       75                       80

GAT  CAC  TGC  GGG  TTA  ATA  GGA  TTT  AAT  GAG  ACT  AGC  TGC  CTT  AAA  AAG        288
Asp  His  Cys  Gly  Leu  Ile  Gly  Phe  Asn  Glu  Thr  Ser  Cys  Leu  Lys  Lys
                85                       90                       95

CTC  GCC  GAT  GGC  TTT  TTT  GAA  TTC  GAG  GTG  TTG  TTT  AAG  TTT  TTA  ACG        336
Leu  Ala  Asp  Gly  Phe  Phe  Glu  Phe  Glu  Val  Leu  Phe  Lys  Phe  Leu  Thr
                100                      105                      110

ACG  GAG  TTT  GGA  AAA  TCA  GTG  ATA  AAC  GTG  GAC  GTC  ATG  GAG  CTT  CTG        384
Thr  Glu  Phe  Gly  Lys  Ser  Val  Ile  Asn  Val  Asp  Val  Met  Glu  Leu  Leu
                115                      120                      125

ACG  AAG  ACC  TTA  GGA  TGG  GAC  ATA  CAG  GAA  GAG  CTC  AAT  AAG  CTG  ACT        432
Thr  Lys  Thr  Leu  Gly  Trp  Asp  Ile  Gln  Glu  Glu  Leu  Asn  Lys  Leu  Thr
      130                      135                      140

AAG  ACG  CAC  TAC  AGT  CCA  CCC  AAA  TTT  GAC  CGC  GGT  CTA  TTA  GGG  AGG        480
Lys  Thr  His  Tyr  Ser  Pro  Pro  Lys  Phe  Asp  Arg  Gly  Leu  Leu  Gly  Arg
145                      150                      155                      160

CTT  CAG  GGA  CTT  AAG  TAT  TGG  GTG  AGA  CAC  TTT  GCT  TCG  TTT  TAT  GTT        528
Leu  Gln  Gly  Leu  Lys  Tyr  Trp  Val  Arg  His  Phe  Ala  Ser  Phe  Tyr  Val
                165                      170                      175

CTG  AGT  GCA  ATG  GAA  AAG  TTT  GCA  GGT  CAA  GCG  GTG  CGT  GTT  TTG  GAC        576
Leu  Ser  Ala  Met  Glu  Lys  Phe  Ala  Gly  Gln  Ala  Val  Arg  Val  Leu  Asp
                180                      185                      190

TCT  ATC  CCA  GAC  GTG  ACT  CCT  GAC  GTC  CAC  GAT  AAG  TAA                       615
Ser  Ile  Pro  Asp  Val  Thr  Pro  Asp  Val  His  Asp  Lys   *
                195                      200                      205
```

KAPOSI'S SARCOMA-ASSOCIATED HERPESVIRUS (KSHV) INTERLEUKIN 6 (IL-6) AND USES THEREOF

The invention disclosed herein was made with Government support under a co-operative agreement CCU210852 from the Centers for Disease Control and Prevention, of the Department of Health and Human Services. Accordingly, the U.S. Government has certain rights in this invention.

Throughout this application, various publications may be referenced by Arabic numerals in brackets. Full citations for these publications may be found at the end of each Experimental Details Section. The disclosures of the publications cited herein are in their entirety hereby incorporated by reference into this application to more fully describe the state of the art to which this invention pertains.

BACKGROUND OF THE INVENTION

Kaposi's sarcoma-associated herpesvirus (KSHV) is a new human herpesvirus (HHV8). Kaposi's sarcoma (KS) is the most common neoplasm occurring in persons with acquired immunodeficiency syndrome (AIDS). Approximately 15–20% of AIDS patients develop this neoplasm which rarely occurs in immunocompetent individuals [13, 14]. Epidemiologic evidence suggests that AIDS-associated KS (AIDS-KS) has an infectious etiology. Gay and bisexual AIDS patients are approximately twenty times more likely than hemophiliac AIDS patients to develop KS, and KS may be associated with specific sexual practices among gay men with AIDS [6, 15, 55, 83]. KS is uncommon among adult AIDS patients infected through heterosexual or parenteral HIV transmission, or among pediatric AIDS parenteral HIV transmission, or among pediatric AIDS patients infected through vertical HIV transmission [77]. Agents previously suspected of causing KS include cytomegalovirus, hepatitis B virus, human papillomavirus, Epstein-Barr virus, human herpesvirus 6, human immunodeficiency virus (HIV), and Mycoplasma penetrans [18, 23, 85, 91, 92]. Non-infectious environmental agents, such as nitrite inhalants, also have been proposed to play a role in KS tumorigenesis [33]. Extensive investigations, however, have not demonstrated an etiologic association between any of these agents and AIDS-KS [37, 44, 46, 90].

BRIEF DESCRIPTION OF THE FIGURES

FIGS. 3A–3F: Nucleotide sequences of the DNA herpesvirus associated with KS (KSHV/HHV8).

FIG. 4A shows the agarose gel of the amplification products from 19 KS DNA samples (lanes 1–19) and FIG. 4B shows specific hybridization of the PCR products to a $^{32}$P end-labelled 25 bp internal oligonucleotide (FIG. 3B) after transfer of the gel to a nitrocellulose filter. Negative samples in lanes 3 and 15 respectively lacked microscopically detectable KS in the sample or did not amplify the constitutive p53 exon 6, suggesting that these samples were negative for technical reasons. An additional 8 AIDS-KS samples were amplified and all were positive for KS330$_{234}$. Lane 20 is a negative control and Lane M is a molecular weight marker.

FIG. 5: Southern blot hybridization of KS330Bam and KS627Bam to AIDS-KS genomic DNA extracted from three subjects (lanes 1, 2, and 3) and digested with PvuII. Based on sequence information (FIG. 3A), restricted sites for Pvu II occur between bp 12361–12362 of the KSHV sequence (FIG. 3A, SEQ ID NO: 1), at bp 134 in KS330Bam (FIG. 3B, SEQ ID NO: 2) and bp 414 in KS627Bam (FIG. 3C, SEQ ID NO: 3). KS330Bam and KS627Bam failed to hybridize to the same fragments in the digests indicating that the two sequences are separated from each other by one or more intervening Bam HI restriction fragments. Digestion with Pvu II and hybridization to KS330Bam resulted in two distinct banding patterns (lanes 1 and 2 vs. lane 3) suggesting variation between KS samples.

FIG. 6: Comparison of amino acid homologies between EBV ORF BDLF1, HSVSA ORF 26 and a 918 bp reading frame of the Kaposi's sarcoma agent which includes KS330Bam. Amino acid identity is denoted by reverse lettering. In HSVSA, ORF 26 encodes a minor capsid VP23 which is a late gene product.

The 220 kD band is absent from the Western blots using patient sera without KS.

FIG. 11: In this figure, 0.5 ml aliquots of the gradient have been fractionated (fractions 1–62) with the 30% gradient fraction being at fraction No. 1. and the 10% gradient fraction being at fraction No. 62. Each fraction has been dot hybridized to a nitrocellulose membrane and then a $^{32}$P-labeled KSHV DNA fragment, KS631Bam has been hybridized to the membrane using standard techniques. The figure shows that the major solubilized fraction of the KSHV genome bands (i.e. is isolated) in fractions 42 through 48 of the gradient with a high concentration of the genome being present in fraction 44. A second band of solubilized KSHV DNA occurs in fractions 26 through 32.

FIG. 12: Location, feature, and relative homologies of KS5 open reading frames compared to translation products of herpesvirus saimiri (HSV), equine herpesvirus 2 (EHV2) and Epstein-Barr virus (EBV).

FIG. 13: Indirect immunofluorescence end-point and geometric mean titers (GMT) in AIDS-KS and AIDS control sera against BHL-6 and P3H3 prior to and after adsorption with P3H3.

Figure 14:
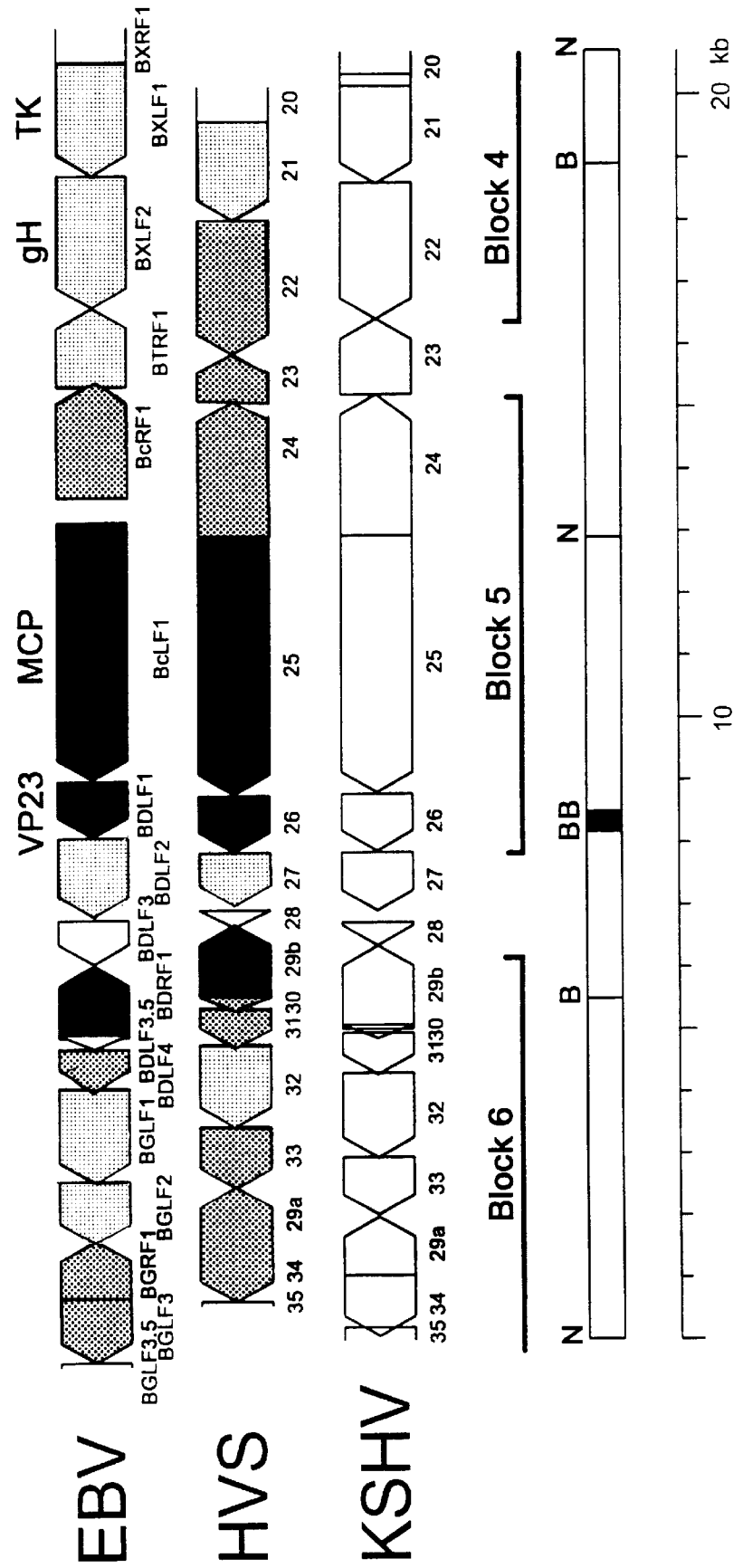

FIG. 14: Genetic map of KS5, a 20.7 kb lambda phage clone insert derived from a human genomic library prepared from an AIDS-KS lesion. Seventeen partial and complete open reading frames (ORFs) are identified with arrows denoting reading frame orientations. Comparable regions of the Epstein-Barr virus (EBV) and herpesvirus saimiri (HVS) genomes are shown for comparison. Levels of amino acid similarity between KSHV ORFs are indicated by shading of EBV and HVS ORFs (black, over 70% similarity; dark gray, 55–70% similarity; light gray, 40–54% similarity; white, no detectable homology). Domains of conserved herpesvirus sequence blocks and locations of restriction endonuclease sites used in subcloning are shown beneath the KSHV map (B, Bam HI site; N, Not I site). The small Bam HI fragment (black) in the VP23 gene homolog corresponds to the KS330Bam fragment generated by representational difference analysis which was used to identify the KS5 lambda phage clone.

Figure 15A:
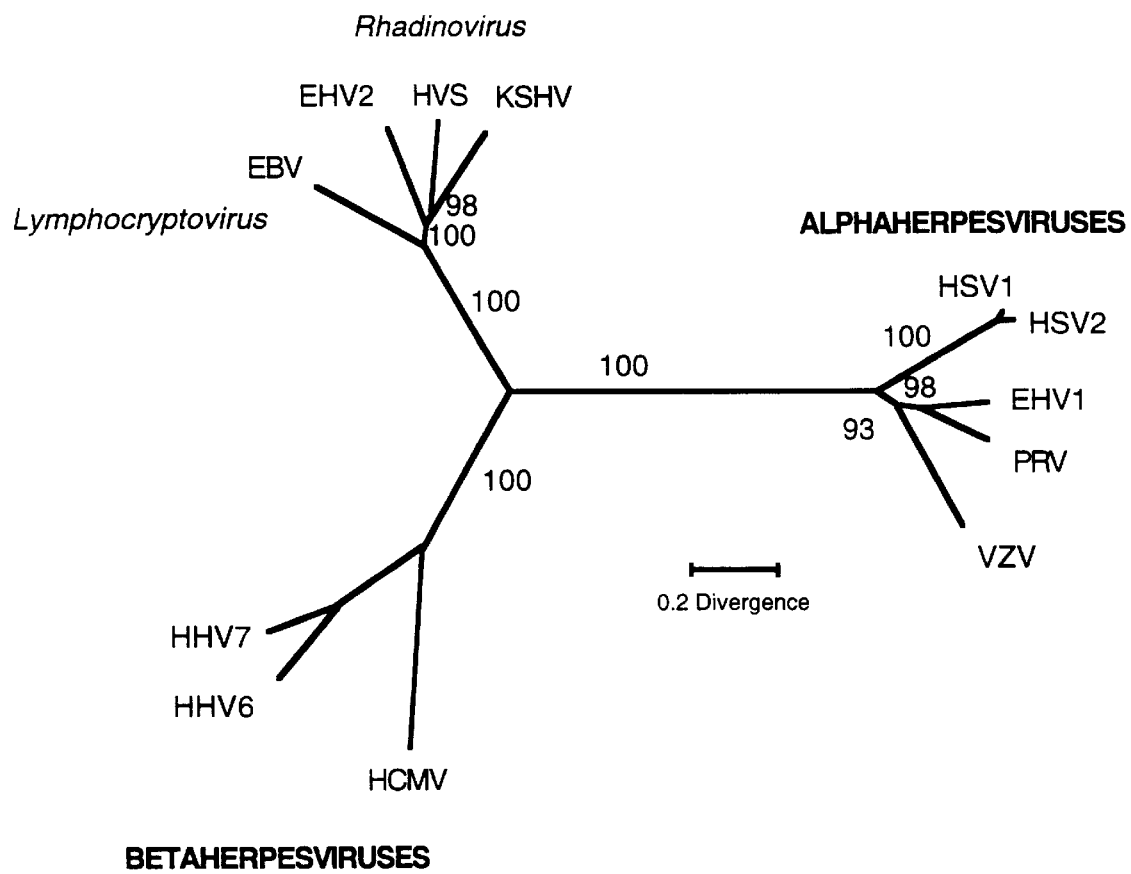
Figure 15B:
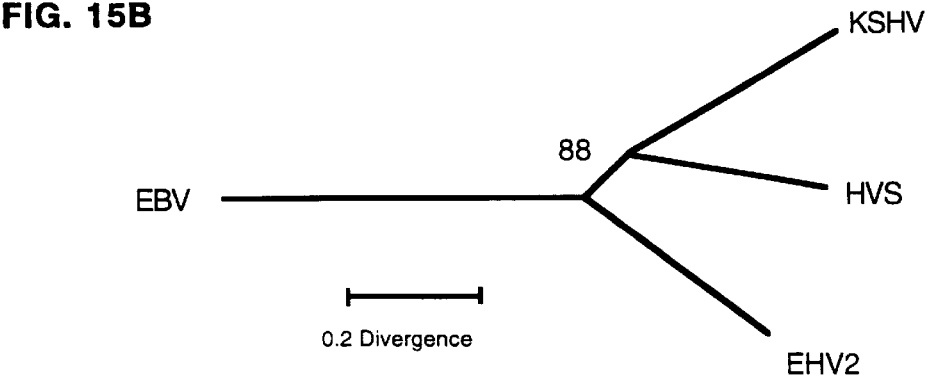

FIGS. 15A–15B: Phylogenetic trees of KSHV based on comparison of aligned amino acid sequences between herpesviruses for the MCP gene and for a concatenated nine-gene set. The comparison of MCP sequences (FIG. 15A) was obtained by the neighbor-joining method and is shown in unrooted form with branch lengths proportional to divergence (mean number of substitution events per site) between the nodes bounding each branch. Comparable results were obtained by maximum parsimony analysis. The number of times out of 100 bootstrap samplings the division indicated by each internal branch was obtained are shown next to each branch; bootstrap values below 75 are not shown. FIG. 15B is a phylogenetic tree of gammaherpesvirus sequences based on a nine-gene set CS1 (see text) and demonstrates that KSHV is most closely related to the gamma-2 herpesvirus sublineage, genus Rhadinovirus. The CS1 amino acid sequence was used to infer a tree by the Protml maximum likelihood method; comparable results, not shown were obtained with the neighbor-joining and maximum parsimony methods. The bootstrap value for the central branch is marked. On the basis of the MCP analysis, the root must lie between EBV and the other three species. Abbreviations for virus species used in the sequence comparisons are 1) Aherpesvirinae: HSV1 and HSV2, herpes simplex virus types 1 and 2; EHV1, equine herpesvirus 1; PRV, pseudorabies virus; and VZV, varicella-zoster virus, 2) Betaherpesvirinae: HCMV, human cytomegalovirus; HHV6 and HHV7, human herpesviruses 6 and 7, and 3) Gammaherpesvirinae: HVS, herpesvirus saimiri; EHV2, equine herpesvirus 2; EBV, Epstein-Barr virus; and Kaposi's sarcoma-associated herpesvirus.

Figure 16A:
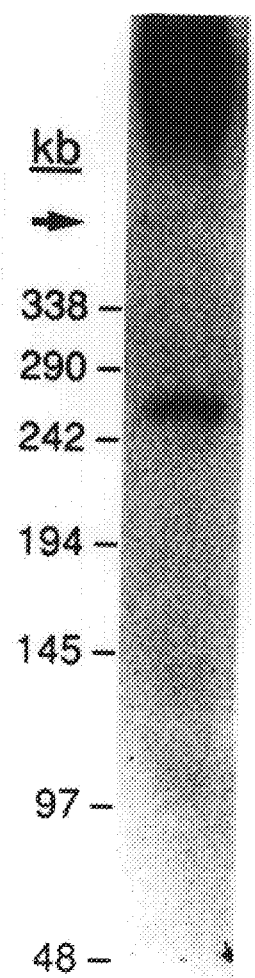
Figure 16B:
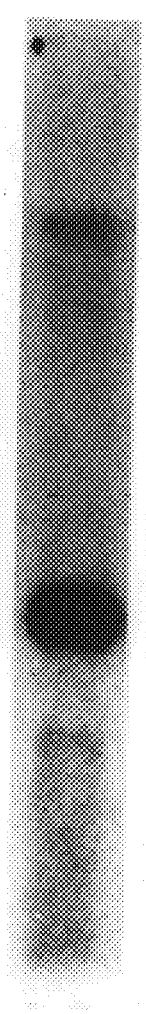

FIGS. 16A–16B: CHEF gel electrophoresis of BCBL-1 DNA hybridized to KS631Bam (FIG. 16A) and EBV terminal repeat (FIG. 16B). KS631Bam hybridizes to a band at 270 kb as well as to a diffuse band at the origin. The EBV termini sequence hybridizes to a 150–160 kb band consistent with the linear form of the genome. Both KS631Bam (dark arrow) and an EBV terminal sequence hybridize to high molecular weight bands immediately below the origin indicating possible concatemeric or circular DNA. The high molecular weight KS631Bam hybridizing band reproduces poorly but is visible on the original autoradiographs.

Figure 17:
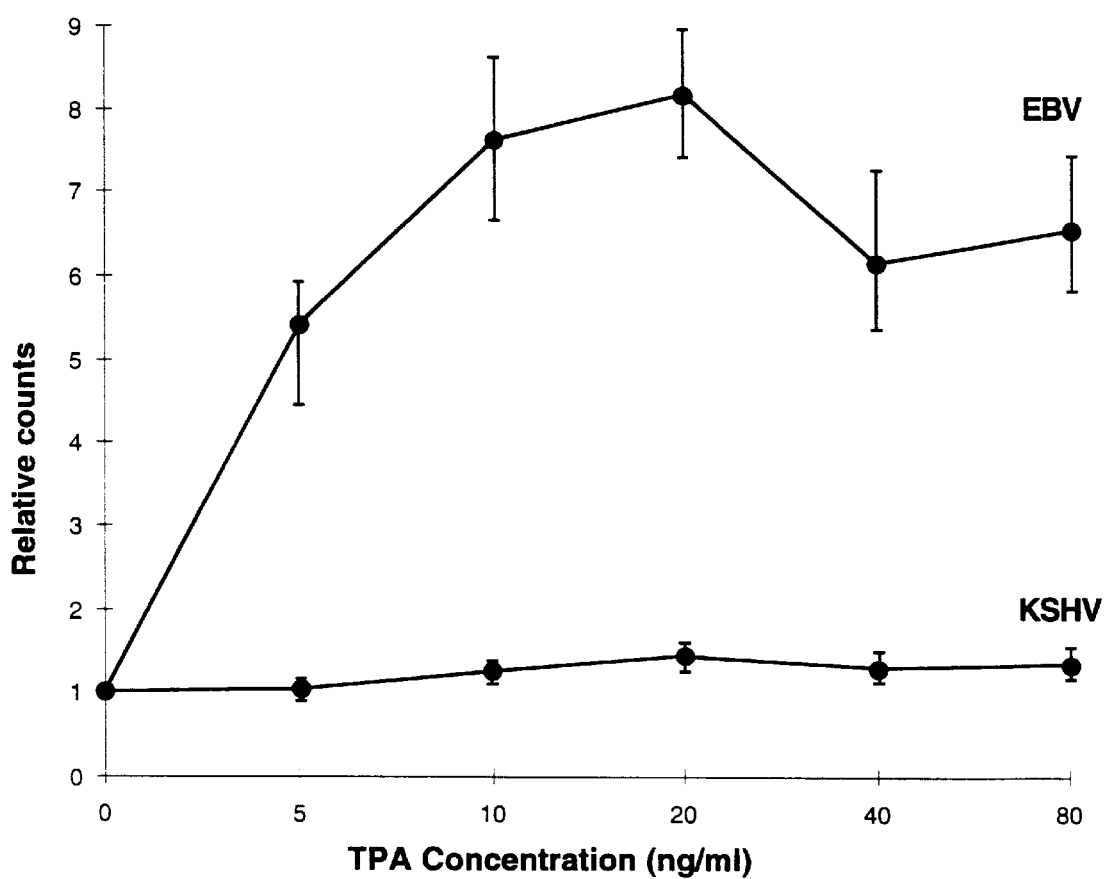

FIG. 17: Induction of KSHV and EBV replication in BCBL-1 with increasing concentrations of TPA. Each determination was made in triplicate after 48 h of TPA incubation and hybridization was standardized to the amount of cellular DNA by hybridization to beta-actin. The figure shows the mean and range of relative increase in hybridizing genome for EBV and KSHV induced by TPA compared to uninduced BCBL-1. TPA at 20 ng/ml induced an eight-fold increase in EBV genome (upper line) at 48 h compared to only a 1.4 fold increase in KSHV genome (lower line). Despite the lower level of KSHV induction, increased replication of KSHV genome after induction with TPA concentrations over 10 ng/ml was reproducibly detected.

Figure 18A:
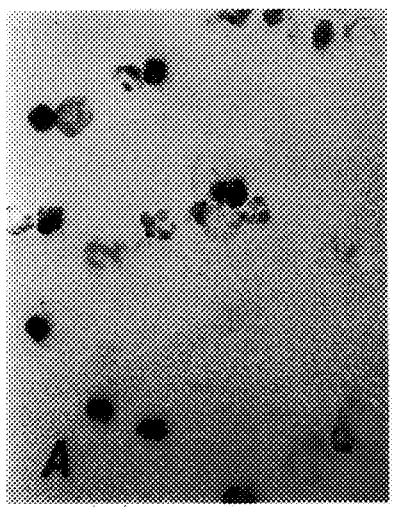
Figure 18B:
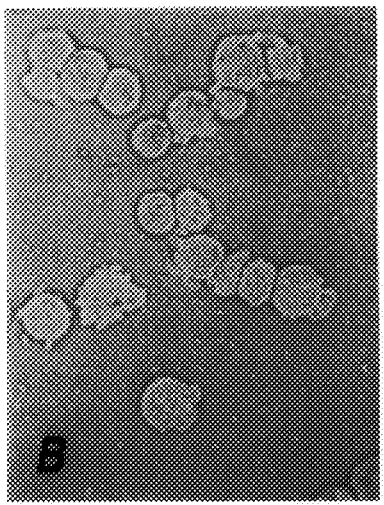
Figure 18C:
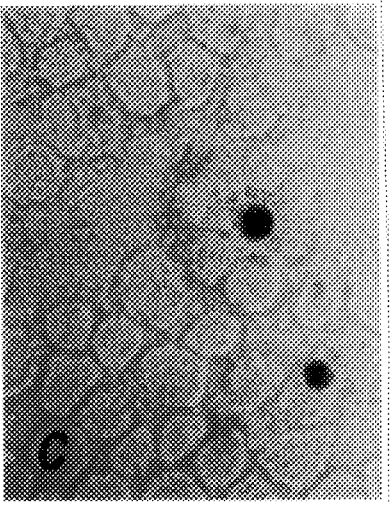

FIGS. 18A–18C: In situ hybridization with an ORF26 oligomer to BCBL-1, Raji and RCC-1 cells. Hybridization occurred to nuclei of KSHV infected BCBL-1 (FIG. 18A), but not to uninfected Raji cells (FIG. 18B). RCC-1, a Raji cell line derived by cultivation of Raji with BCBL-1 in communicating chambers separated by a 0.45 $\mu$ filter, shows rare cells with positive hybridization to the KSHV ORF26 probe (FIG. 18C).

Figure 19A:
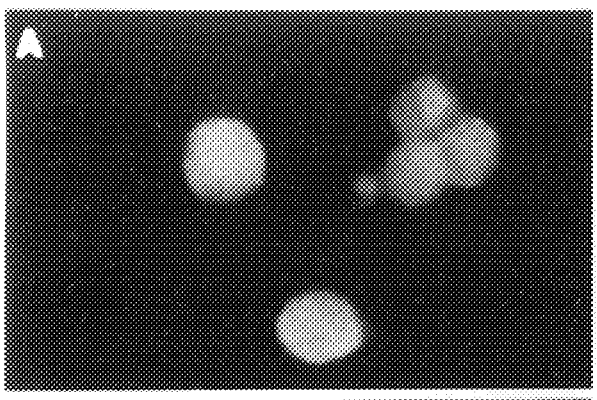
Figure 19B:
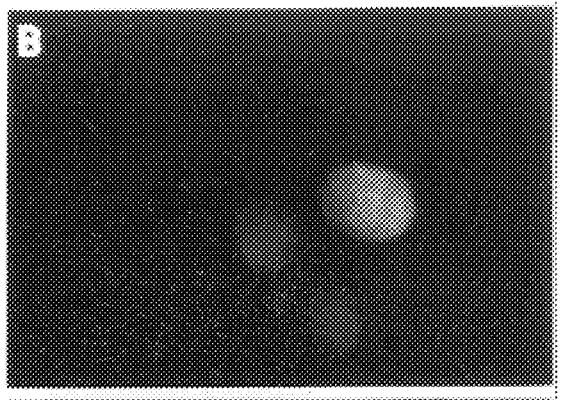
Figure 19C:
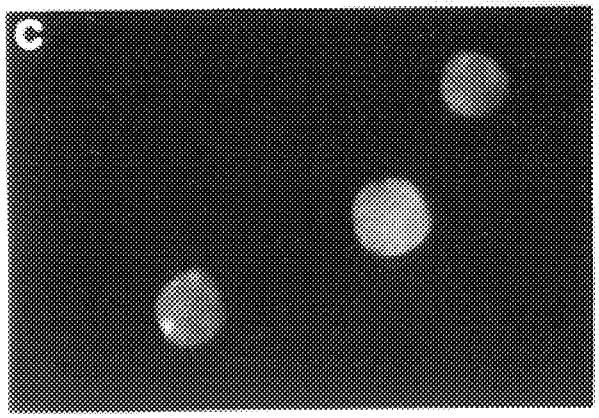
Figure 19D:
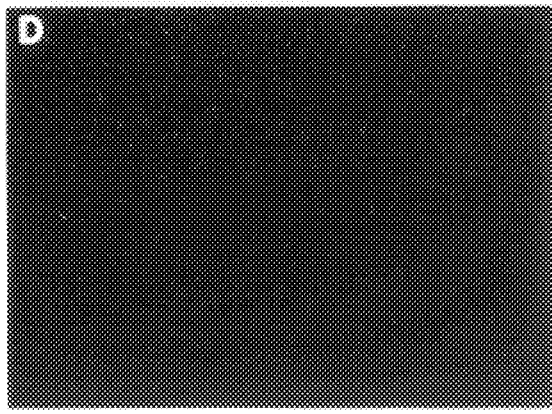

FIGS. 19A–19D: Representative example of IFA staining of BHL-6 with AIDS-KS patient sera and control sera from HIV-infected patients without KS. Both AIDS-KS (FIG. 19A) and control (FIG. 19B) sera show homogeneous staining of BHL-6 at 1:50 dilution. After adsorption with paraformaldehyde-fixed P3H3 to remove cross-reacting antibodies directed against lymphocyte and EBV antigens, antibodies from AIDS-KS sera localize to BHL-6 nuclei (FIG. 19C). P3H3 adsorption of control sera eliminates immunofluorescent staining of BHL-6 (FIG. 19D).

Figure 20A:
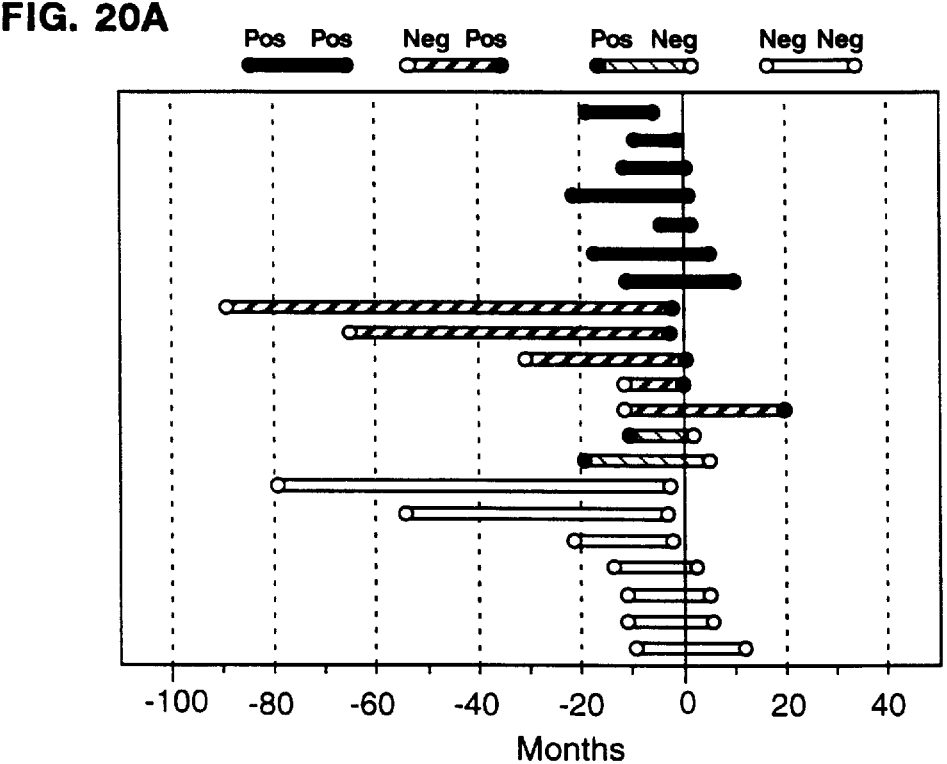
Figure 20B:
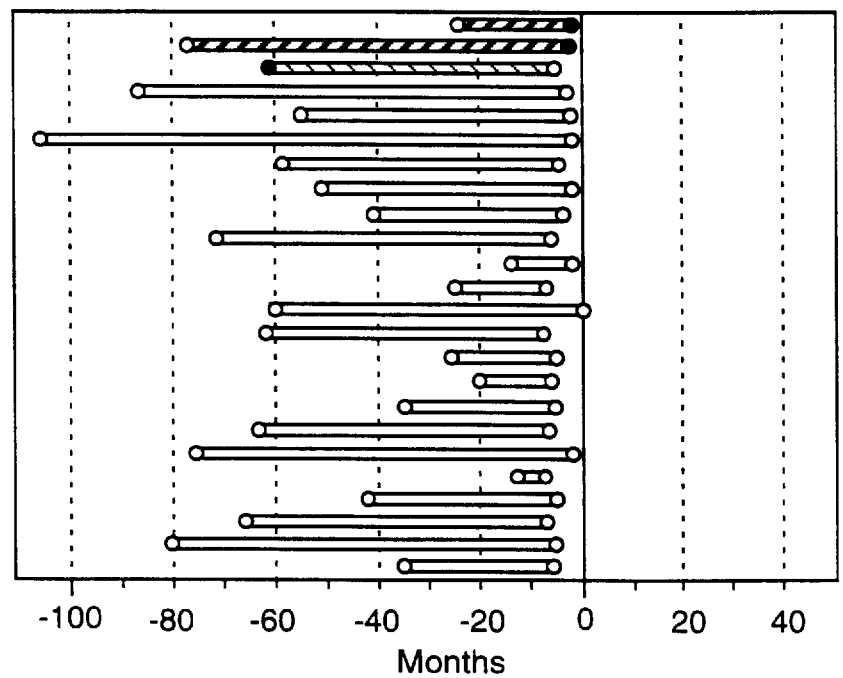

FIGS. 20A–20B: Longitudinal PCR examination for KSHV DNA of paired PBMC samples from AIDS-KS patients (A) and homosexual/bisexual AIDS patients without KS (B). Time 0 is the date of KS onset for cases or other AIDS-defining illness for controls. All samples were randomized and examined blindly. Overall, 7 of the KS patients were KSHV positive at both examination dates (solid bars) and 5 converted from a negative to positive PBMC sample (forward striped bars) immediately prior to or after KS onset. Two previously positive KS patients were negative after KS diagnosis (reverse striped bars) and the remaining KS patients were negative at both timepoints (open bars). Two homosexual/bisexual control PBMC samples without KS converted from negative to positive and one control patient reverted from PCR positive to negative for KSHV DNA.

FIG. 21: Sample collection characteristics for AIDS-KS patients, gay/bisexual AIDS patients and hemophilic AIDS patients.

FIG. 22: PCR analysis of KS330$_{233}$ in DNA samples from patients with Kaposi's sarcoma and tumor controls.

Figure 23:
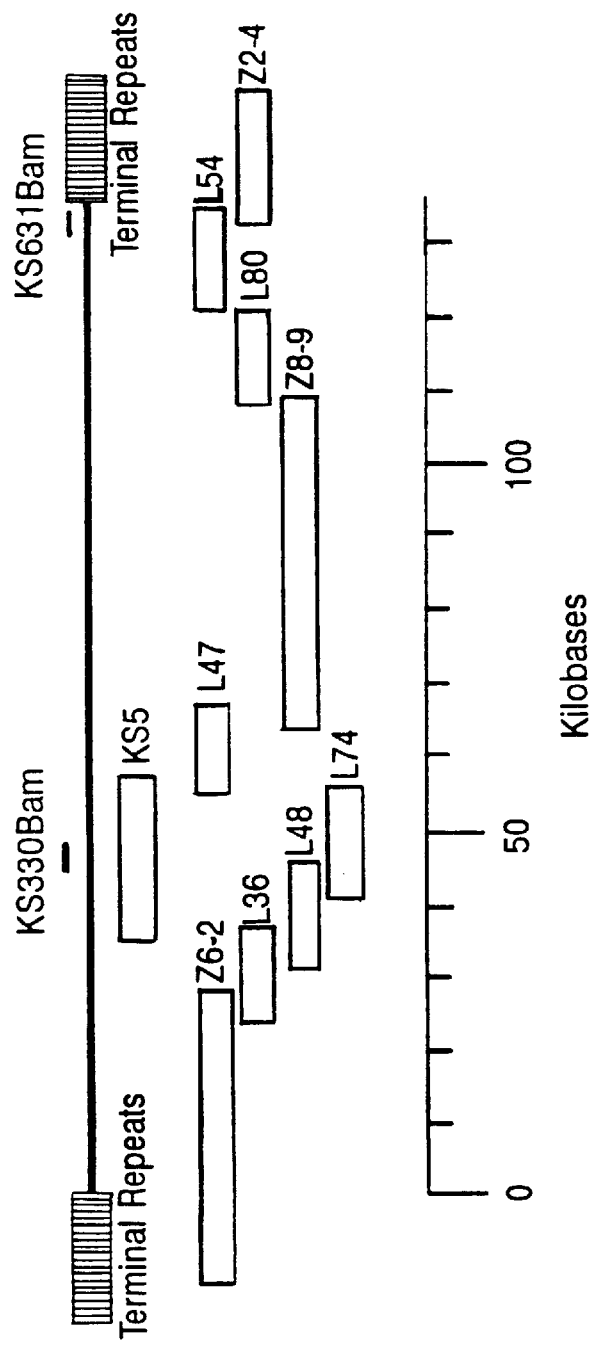

FIG. 23: Map of the long unique coding region of the KSHV/HHV8 genome mapped with overlapping cosmid (Z-#) and lambda phage (L-#) inserts.

Figure 24:
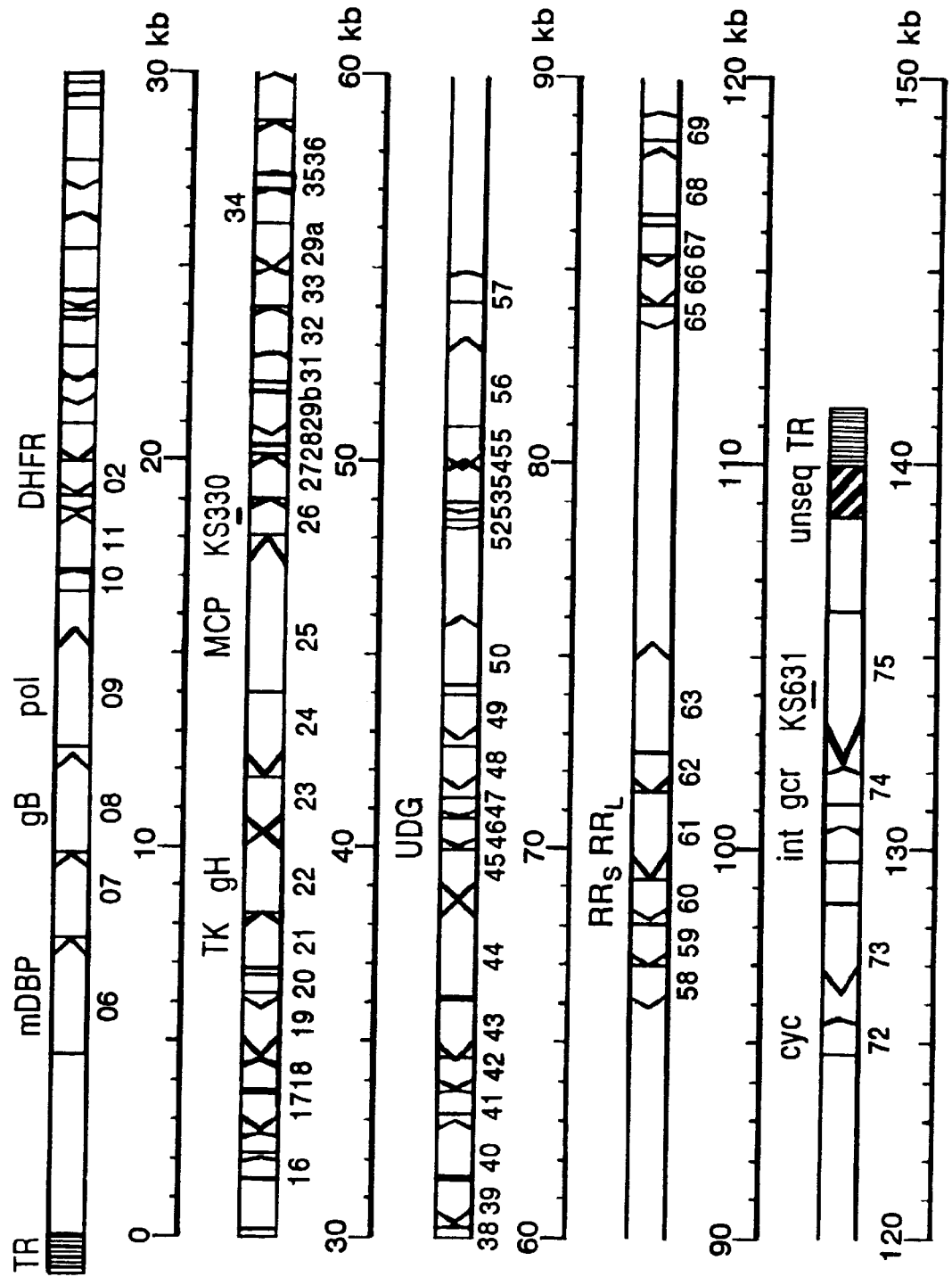

FIG. 24: Partial gene map of the KSHV sequence based on sequencing of the cosmid and lambda inserts shown in FIG. 23. The entire genome has been sequenced but for a small region, about 2 kilobase, at the right end (unseq) which is present in cosmid Z2–4. Numbers indicate putative open reading frames (ORFs). Terminal repeat (TR). Proteins identified by sequence homology include, but are not limited to: single-stranded DNA binding protein (mDBP/SSBP), glycoprotein B (gB), DNA-dependent DNA polymerase (pol), dihydrofolate reductase (DHFR), thymidine kinase (TK), glycoprotein H (gH), major capsid protein (MCP), uracil-DNA glycosylase (UDG), ribonucleotide reductase small subunit (RR$_S$), ribonucleotide reductase large subunit (RR$_L$), cyclin D homolog (cyc), integrin homolog (int), G-protein coupled receptor (gcr).

DETAILED DESCRIPTION OF THE INVENTION

Definitions

The following standard abbreviations are used throughout the specification to indicate specific nucleotides:

C=cytosine A=adenosine

T=thymidine G=guanosine

The term "nucleic acids", as used herein, refers to either DNA or RNA. "Nucleic acid sequence" or "polynucleotide sequence" refers to a single- or double-stranded polymer of deoxyribonucleotide or ribonucleotide bases read from the 5' to the 3' end. It includes both self-replicating plasmids, infectious polymers of DNA or RNA and nonfunctional DNA or RNA.

By a nucleic acid sequence "homologous to" or "complementary to", it is meant a nucleic acid that selectively hybridizes, duplexes or binds to viral DNA sequences encoding proteins or portions thereof when the DNA sequences encoding the viral protein are present in a human genomic or cDNA library. A DNA sequence which is similar or complementary to a target sequence can include sequences which are shorter or longer than the target sequence so long as they meet the functional test set forth. Hybridization conditions are specified along with the source of the cDNA library.

Typically, the hybridization is done in a Southern blot protocol using a 0.2×SSC, 0.1% SDS, 65° C. wash. The term "SSC" refers to a citrate-saline solution of 0.15M sodium chloride and 20 mM sodium citrate. Solutions are often expressed as multiples or fractions of this concentration. For example, 6×SSC refers to a solution having a sodium chloride and sodium citrate concentration of 6 times this amount or 0.9M sodium chloride and 120 mM sodium citrate. 0.2×SSC refers to a solution 0.2 times the SSC concentration or 0.03M sodium chloride and 4 mM sodium citrate.

The phrase "nucleic acid molecule encoding" refers to a nucleic acid molecule which directs the expression of a specific protein or peptide. The nucleic acid sequences include both the DNA strand sequence that is transcribed into RNA and the RNA sequence that is translated into protein. The nucleic acid molecule include both the full length nucleic acid sequences as well as non-full length sequences derived from the full length protein. It being further understood that the sequence includes the degenerate codons of the native sequence or sequences which may be introduced to provide codon preference in a specific host cell.

The phrase "expression cassette", refers to nucleotide sequences which are capable of affecting expression of a structural gene in hosts compatible with such sequences. Such cassettes include at least promoters and optionally, transcription termination signals. Additional factors necessary or helpful in effecting expression may also be used as described herein.

The term "operably linked" as used herein refers to linkage of a promoter upstream from a DNA sequence such that the promoter mediates transcription of the DNA sequence.

The term "vector", refers to viral expression systems, autonomous self-replicating circular DNA (plasmids), and includes both expression and nonexpression plasmids. Where a recombinant microorganism or cell culture is described as hosting an "expression vector," this includes both extrachromosomal circular DNA and DNA that has been incorporated into the host chromosome(s). Where a vector is being maintained by a host cell, the vector may either be stably replicated by the cells during mitosis as an autonomous structure, or is incorporated within the host's genome.

The term "plasmid" refers to an autonomous circular DNA molecule capable of replication in a cell, and includes both the expression and nonexpression types. Where a recombinant microorganism or cell culture is described as hosting an "expression plasmid", this includes latent viral DNA integrated into the host chromosome(s). Where a plasmid is being maintained by a host cell, the plasmid is either being stably replicated by the cells during mitosis as an autonomous structure or is incorporated within the host's genome.

The phrase "recombinant protein" or "recombinantly produced protein" refers to a peptide or protein produced using non-native cells that do not have an endogenous copy of DNA able to express the protein. The cells produce the protein because they have been genetically altered by the introduction of the appropriate nucleic acid sequence. The recombinant protein will not be found in association with proteins and other subcellular components normally associated with the cells producing the protein.

The following terms are used to describe the sequence relationships between two or more nucleic acid molecules or polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence.

Optimal alignment of sequences for aligning a comparison window may be conducted by the local homology algorithm of Smith and Waterman (1981) *Adv. Appl. Math.* 2:482, by the homology alignment algorithm of Needleman and Wunsch (1970) *J. Mol. Biol.* 48:443, by the search for similarity method of Pearson and Lipman (1988) *Proc. Natl. Acad. Sci. (USA)* 85:2444, or by computerized implementations of these algorithms (GAP, BESTFIT, FASTA, and TFASTA in the Wisconsin Genetics Software Package Release 7.0, Genetics Computer Group, 575 Science Dr., Madison, Wis.).

As applied to polypeptides, the terms. "substantial identity" or "substantial sequence identity" mean that two peptide sequences, when optimally aligned, such as by the programs GAP or BESTFIT using default gap which share at least 90 percent sequence identity, preferably at least 95 percent sequence identity, more preferably at least 99 percent sequence identity or more.

"Percentage amino acid identity" or "percentage amino acid sequence identity" refers to a comparison of the amino acids of two polypeptides which, when optimally aligned, have approximately the designated percentage of the same amino acids. For example, "95% amino acid identity" refers to a comparison of the amino acids of two polypeptides which when optimally aligned have 95% amino acid identity. Preferably, residue positions which are not identical differ by conservative amino acid substitutions. For example, the substitution of amino acids having similar chemical properties such as charge or polarity are not likely to effect the properties of a protein. Examples include glutamine for asparagine or glutamic acid for aspartic acid.

The phrase "substantially purified" or "isolated" when referring to a herpesvirus peptide or protein, means a chemical composition which is essentially free of other cellular components. It is preferably in a homogeneous state although it can be in either a dry or aqueous solution. Purity and homogeneity are typically determined using analytical chemistry techniques such as polyacrylamide gel electrophoresis or high performance liquid chromatography. A protein which is the predominant species present in a preparation is substantially purified. Generally, a substantially purified or isolated protein will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The phrase "specifically binds to an antibody" or "specifically immunoreactive with", when referring to a protein or peptide, refers to a binding reaction which is determinative of the presence of the herpesvirus of the invention in the presence of a heterogeneous population of proteins and other biologics including viruses other than the herpesvirus. Thus, under designated immunoassay conditions, the specified antibodies bind to the herpesvirus antigens and do not bind in a significant amount to other antigens present in the sample. Specific binding to an antibody under such conditions may require an antibody that is selected for its specificity for a particular protein. For example, antibodies raised to the human herpesvirus immunogen described herein can be selected to obtain antibodies specifically immunoreactive with the herpesvirus proteins and not with other proteins. These antibodies recognize proteins homologous to the human herpesvirus protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane [32] for a description of immunoassay formats and conditions that can be used to determine specific immunoreactivity.

"Biological sample" as used herein refers to any sample obtained from a living organism or from an organism that has died. Examples of biological samples include body fluids and tissue specimens.

I. Kaposis's Sarcoma (KS)—Associated Herpesvirus

This invention provides an isolated nucleic acid molecule which encodes Kaposi's sarcoma-associated herpesvirus (KSHV) interleukin 6 (IL-6).

In one embodiment, the isolated nucleic acid molecule which encodes IL-6 has the nucleic acid sequence as set forth in SEQ ID NO: 1.

In another embodiment, the isolated nucleic acid molecule which encodes IL-6 encodes the amino acid sequence as set forth in SEQ ID NO: 1.

In one embodiment the isolated nucleic acid molecule is genomic DNA. In another embodiment the isolated DNA molecule is cDNA. In another embodiment RNA is derived from the isolated nucleic acid molecule or is capable of hybridizing with the isolated DNA molecule. As used herein "genomic" means both coding and non-coding regions of the isolated nucleic acid molecule.

Further, the nucleic acid molecule above may be associated with lymphoproliferative diseases including, but not limited to: Hodgkin's disease, non-Hodgkin's lymphoma, lymphatic leukemia, lymphosarcoma, splenomegaly, reticular cell sarcoma, Sezary's syndrome, mycosis fungoides, central nervous system lymphoma, AIDS related central nervous system lymphoma, post-transplant lymphoproliferative disorders, and Burkitt's lymphoma. A lymphoproliferative disorder is characterized as being the uncontrolled clonal or polyclonal expansion of lymphocytes involving lymph nodes, lymphoid tissue and other organs.

This invention provides an isolated polypeptide encoding IL-6. In one embodiment, the isolated polypeptide has the amino acid sequence as set forth in SEQ ID NO: 1.

This invention provides for a replicable vector comprising the isolated nucleic acid molecule of the DNA virus. The vector includes, but is not limited to: a plasmid, cosmid, λ phage or yeast artificial chromosome (YAC) which contains at least a portion of the isolated nucleic acid molecule.

As an example to obtain these vectors, insert and vector DNA can both be exposed to a restriction enzyme to create complementary ends on both molecules which base pair with each other and are then ligated together with DNA ligase. Alternatively, linkers can be ligated to the insert DNA which correspond to a restriction site in the vector DNA, which is then digested with the restriction enzyme which cuts at that site. Other means are also available and known to an ordinary skilled practitioner.

Regulatory elements required for expression include promoter or enhancer sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art, for example the methods described above for constructing vectors in general.

This invention provides a host cell containing the above vector. The host cell may contain the isolated DNA molecule artificially introduced into the host cell. The host cell may be a eukaryotic or bacterial cell (such as *E. coli*), yeast cells, fungal cells, insect cells and animal cells. Suitable animal cells include, but are not limited to Vero cells, HeLa cells, Cos cells, CV1 cells and various primary mammalian cells.

A. Sequence identity of the viral DNA and its proteins

The human herpesvirus of the invention is not limited to the virus having the specific DNA sequences described herein. The KS-associated human herpesvirus DNA shows substantial sequence identity, as defined above, to the viral DNA sequences described herein. DNA from the human herpesvirus typically selectively hybridizes to one or more of the following three nucleic acid probes:

Probe 1:

| AGCCGAAAGG | ATTCCACCAT | TGTGCTCGAA | TCCAACGGAT | TTGACCCCGT |
|---|---|---|---|---|
| GTTCCCCATG | GTCGTGCCGC | AGCAACTGGG | GCACGCTATT | CTGCAGCAGC |
| TGTTGGTGTA | CCACATCTAC | TCCAAAATAT | CGGCCGGGGC | CCCGGATGAT |
| GTAAATATGG | CGGAACTTGA | TCTATATACC | ACCAATGTGT | CATTTATGGG |
| GCGCACATAT | CGTCTGGACG | TAGACAACAC | GGA | |

Probe 2:

| GAAATTACCC | ACGAGATCGC | TTCCCTGCAC | ACCGCACTTG | GCTACTCATC |
|---|---|---|---|---|
| AGTCATCGCC | CCGGCCCACG | TGGCCGCCAT | AACTACAGAC | ATGGGAGTAC |
| ATTGTCAGGA | CCTCTTTATG | ATTTTCCCAG | GGGACGCGTA | TCAGGACCGC |
| CAGCTGCATG | ACTATATCAA | AATGAAAGCG | GGCGTGCAAA | CCGGCTCACC |
| GGGAAACAGA | ATGGATCACG | TGGGATACAC | TGCTGGGGTT | CCTCGCTGCG |
| AGAACCTGCC | CGGTTTGAGT | CATGGTCAGC | TGGCAACCTG | CGAGATAATT |
| CCCACGCCGG | TCACATCTGA | CGTTGCCT | | |

Probe 3:

| AACACGTCAT | GTGCAGGAGT | GACATTGTGC | CGCGGAGAAA | CTCAGACCGC |
|---|---|---|---|---|
| ATCCCGTAAC | CACACTGAGT | GGGAAAATCT | GCTGGCTATG | TTTTCTGTGA |
| TTATCTATGC | CTTAGATCAC | AACTGTCACC | CG | |

Hybridization of a viral DNA to the nucleic acid probes listed above is determined by using standard nucleic acid hybridization techniques as described herein. In particular, PCR amplification of a viral genome can be carried out using the following three sets of PCR primers:

| 1) | AGCCGAAAGGATTCCACCAT; |
|---|---|
| | TCCGTGTTGTCTACGTCCAG |
| 2) | GAAATTACCCACGAGATCGC; |
| | AGGCAACGTCAGATGTGA |
| 3) | AACACGTCATGTGCAGGAGTGAC; |
| | CGGGTGACAGTTGTGATCTAAGG |

In PCR techniques, oligonucleotide primers, as listed above complementary to the two 3' borders of the DNA region to be amplified are synthesized. The polymerase chain reaction is then carried out using the two primers. See *PCR Protocols: A Guide to Methods and Applications* [74]. Following PCR amplification, the PCR-amplified regions of a viral DNA can be tested for their ability to hybridize to the three specific nucleic acid probes listed above. Alternatively, hybridization of a viral DNA to the above nucleic acid probes can be performed by a Southern blot procedure without viral DNA amplification and under stringent hybridization conditions as described herein.

Oligonucleotides for use as probes or PCR primers are chemically synthesized according to the solid phase phosphoramidite triester method first described by Beaucage and Carruthers [19] using an automated synthesizer, as described in Needham-VanDevanter [69]. Purification of oligonucleotides is by either native acrylamide gel electrophoresis or by anion-exchange HPLC as described in Pearson, J. D. and Regnier, F. E. [75A]. The sequence of the synthetic oligonucleotide can be verified using the chemical degradation method of Maxam, A. M. and Gilbert, W. [63].

B. Isolation and propagation of KS-inducing strains of the Human Herpesvirus

Using conventional methods, the human herpesvirus can be propagated in vitro. For example, standard techniques for growing herpes viruses are described in Ablashi, D. V. [1]. Briefly, PHA stimulated cord blood mononuclear cells, macrophage, neuronal, or glial cell lines are cocultivated with cerebrospinal fluid, plasma, peripheral blood leukocytes, or tissue extracts containing viral infected cells or purified virus. The recipient cells are treated with 5 $\mu$g/ml polybrene for 2 hours at 37° C. prior to infection. Infected cells are observed by demonstrating morphological changes, as well as being positive for antigens from the human herpesvirus by using monoclonal antibodies immunoreactive with the human herpes virus in an immunofluorescence assay.

For virus isolation, the virus is either harvested directly from the culture fluid by direct centrifugation, or the infected cells are harvested, homogenized or lysed and the virus is separated from cellular debris and purified by standard methods of isopycnic sucrose density gradient centrifugation.

One skilled in the art may isolate and propagate the DNA herpesvirus associated with Kaposi's sarcoma (KSHV) employing the following protocol. Long-term establishment of a B lymphoid cell line infected with the KSHV from body-cavity based lymphomas (RCC-1 or BHL-6) is prepared extracting DNA from the Lymphoma tissue using standard techniques [27, 49, 66].

The KS associated herpesvirus may be isolated from the cell DNA in the following manner. An infected cell line (BHL-6 RCC-1), which can be lysed using standard methods such as hyposomatic shocking and Dounce homogenization, is first pelleted at 2000×g for 10 minutes, the supernatant is removed and centrifuged again at 10,000×g for 15 minutes to remove nuclei and organelles. The supernatant is filtered through a 0.45$\mu$ A filter and centrifuged again at 100,000×g for 1 hour to pellet the virus. The virus can then be washed and centrifuged again at 100,000×g for 1 hour.

The DNA is tested for the presence of the KSHV by Southern blotting and PCR using the specific probes as described hereinafter. Fresh lymphoma tissue containing viable infected cells is simultaneously filtered to form a single cell suspension by standard techniques [49, 66]. The cells are separated by standard Ficoll-Plaque centrifugation and lymphocyte layer is removed. The lymphocytes are then placed at >1×10$^6$ cells/ml into standard lymphocyte tissue culture medium, such as RMP 1640 supplemented with 10% fetal calf serum. Immortalized lymphocytes containing the KSHV virus are indefinitely grown in the culture media while nonimmortilized cells die during course of prolonged cultivation.

Further, the virus may be propagated in a new cell line by removing media supernatant containing the virus from a continuously infected cell line at a concentration of >1×10$^6$ cells/ml. The media is centrifuged at 2000×g for 10 minutes and filtered through a 0.45µ filter to remove cells. The media is applied in a 1:1 volume with cells growing at >1×10$^6$ cells/ml for 48 hours. The cells are washed and pelleted and placed in fresh culture medium, and tested after 14 days of growth.

RCC-1 and RCC-1$_{2F5}$ were deposited on Oct. 19, 1994 under ATCC Accession No. CRL 11734 and CRL 11735, respectively, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. BHL-6 was deposited on Nov. 18, 1994 under ATCC Accession No. CRL 11762 pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.

C. Immunological Identity of the Virus

The KS-associated human herpesvirus can also be described immunologically. KS-associated human herpesviruses are selectively immunoreactive to antisera generated against a defined immunogen such as the viral major capsid protein depicted in SEQ. ID NO. 12 , herein. Immunoreactivity is determined in an immunoassay using a polyclonal antiserum which was raised to the protein which is encoded by the amino acid sequence or nucleic acid sequence of SEQ ID NOs: 18–20. This antiserum is selected to have low crossreactivity against other herpes viruses and any such crossreactivity is removed by immunoabsorbtion prior to use in the immunoassay.

In order to produce antisera for use in an immunoassay, the protein which is encoded by the amino acid sequence or nucleic acid of SEQ ID NOs: 18–20 is isolated as described herein. For example, recombinant protein can be produced in a mammalian cell line. An inbred strain of mice such as balb/c is immunized with the protein which is encoded by the amino acid sequence or nucleic acid of SEQ ID NOs: 2–37 using a standard adjuvant, such as Freund's adjuvant, and a standard mouse immunization protocol (see [32], supra). Alternatively, a synthetic peptide derived from the sequences disclosed herein and conjugated to a carrier protein can be used an immunogen. Polyclonal sera are collected and titered against the immunogen protein in an immunoassay, for example, a solid phase immunoassay with the immunogen immobilized on a solid support. Polyclonal antisera with a titer of 10$^4$ or greater are selected and tested for their cross reactivity against other viruses of the gammaherpesvirinae subfamily, particularly human herpes virus types 1–7, by using a standard immunoassay as described in [32], supra. These other gammaherpesvirinae virus can be isolated by standard techniques for isolation herpes viruses as described herein.

The ability of the above viruses to compete with the binding of the antisera to the immunogen protein is determined. The percent crossreactivity for other viruses is calculated, using standard calculations. Those antisera with less than 10% crossreactivity with each of the other viruses listed above is selected and pooled. The cross-reacting antibodies are then removed from the pooled antisera by immunoabsorption with the above-listed viruses.

The immunoabsorbed and pooled antisera are then used in a competitive binding immunoassay procedure as described above to compare an unknown virus preparation to the specific KS herpesvirus preparation described herein and containing the nucleic acid sequence described in SEQ ID NO:1. In order to make this comparison, the immunogen protein which is encoded by the amino acid sequence or nucleic acid of SEQ ID NO:1 is the labeled antigen and the virus preparations are each assayed at a wide range of concentrations. The amount of each virus preparation required to inhibit 50% of the binding of the antisera to the labeled immunogen protein is determined. Those viruses that specifically bind to an antibody generated to an immunogen consisting of the protein of SEQ ID NO:1 are those virus where the amount of virus needed to inhibit 50% of the binding to the protein does not exceed an established amount. This amount is no more than 10 times the amount of the virus that is needed for 50% inhibition for the KS-associated herpesvirus containing the DNA sequence of SEQ ID NO: 1. Thus, the KS-associated herpesviruses of the invention can be defined by immunological comparison to the specific strain of the KS-associated herpesvirus for which nucleic acid sequences are provided herein.

This invention provides, a nucleic acid molecule of at least 14 nucleotides capable of specifically hybridizing with the isolated DNA molecule. In one embodiment, the molecule is DNA. In another embodiment, the molecule is RNA. In another embodiment the nucleic acid molecule may be 14–20 nucleotides in length. In another embodiment the nucleic acid molecule may be 16 nucleotides in length.

This invention provides, a nucleic acid molecule of at least 14 nucleotides capable of specifically hybridizing with a nucleic acid molecule which is complementary to the isolated DNA molecule. In one embodiment, the molecule is DNA. In another embodiment, the molecule is RNA.

The nucleic acid molecule of at least 14 nucleotides may hybridize with moderate stringency to at least a portion of a nucleic acid molecule with a sequence shown in FIGS. 3A–3F.

High stringent hybridization conditions are selected at about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.02 molar at pH 7 and the temperature is at least about 60° C. As other factors may significantly affect the stringency of hybridization, including, among others, base composition and size of the complementary strands, the presence of organic solvents, ie. salt or formamide concentration, and the extent of base mismatching, the combination of parameters is more important than the absolute measure of any one. For Example high stringency may be attained for example by overnight hybridization at about 68° C. in a 6× SSC solution, washing at room temperature with 6× SSC solution, followed by washing at about 68° C. in a 6× SSC in a 0.6× SSX solution.

Hybridization with moderate stringency may be attained for example by: 1) filter pre-hybridizing and hybridizing with a solution of 3× sodium chloride, sodium citrate (SSC), 50% formamide, 0.1M Tris buffer at Ph 7.5, 5× Denhardt's solution; 2.) Pre-hybridization at 37° C. for 4 hours; 3) hybridization at 37° C. with amount of labelled probe equal to 3,000,000 cpm total for 16 hours; 4) wash in 2× SSC and 0.1% SDS solution; 5) wash 4× for 1 minute each at room temperature at 4× at 60° C. for 30 minutes each; and 6) dry and expose to film.

The phrase "selectively hybridizing to" refers to a nucleic acid probe that hybridizes, duplexes or binds only to a particular target DNA or RNA sequence when the target sequences are present in a preparation of total cellular DNA or RNA. By selectively hybridizing it is meant that a probe binds to a given target in a manner that is detectable in a different manner from non-target sequence under high stringency conditions of hybridization. "Complementary" or "target" nucleic acid sequences refer to those nucleic acid sequences which selectively hybridize to a nucleic acid probe. Proper annealing conditions depend, for example, upon a probe's length, base composition, and the number of mismatches and their position on the probe, and must often be determined empirically. For discussions of nucleic acid probe design and annealing conditions, see, for example, Sambrook et al., [81] or Ausubel, F., et al., [8].

It will be readily understood by those skilled in the art and it is intended here, that when reference is made to particular sequence listings, such reference includes sequences which substantially correspond to its complementary sequence and those described including allowances for minor sequencing errors, single base changes, deletions, substitutions and the like, such that any such sequence variation corresponds to the nucleic acid sequence of the pathogenic organism or disease marker to which the relevant sequence listing relates.

Nucleic acid probe technology is well known to those skilled in the art who readily appreciate that such probes may vary greatly in length and may be labeled with a detectable label, such as a radioisotope or fluorescent dye, to facilitate detection of the probe. DNA probe molecules may be produced by insertion of a DNA molecule having the full-length or a fragment of the isolated nucleic acid molecule of the DNA virus into suitable vectors, such as plasmids or bacteriophages, followed by transforming into suitable bacterial host cells, replication in the transformed bacterial host cells and harvesting of the DNA probes, using methods well known in the art. Alternatively, probes may be generated chemically from DNA synthesizers.

DNA virus nucleic acid rearrangements/mutations may be detected by Southern blotting, single stranded conformational polymorphism gel electrophoresis (SSCP), PCR or other DNA based techniques, or for RNA species by Northern blotting, PCR or other RNA-based techniques.

RNA probes may be generated by inserting the full length or a fragment of the isolated nucleic acid molecule of the DNA virus downstream of a bacteriophage promoter such as T3, T7 or SP6. Large amounts of RNA probe may be produced by incubating the labeled nucleotides with a linearized isolated nucleic acid molecule of the DNA virus or its fragment where it contains an upstream promoter in the presence of the appropriate RNA polymerase.

As defined herein nucleic acid probes may be DNA or RNA fragments. DNA fragments can be prepared, for example, by digesting plasmid DNA, or by use of PCR, or synthesized by either the phosphoramidite method described by Beaucage and Carruthers, [19], or by the triester method according to Matteucci, et al., [62], both incorporated herein by reference. A double stranded fragment may then be obtained, if desired, by annealing the chemically synthesized single strands together under appropriate conditions or by synthesizing the complementary strand using DNA polymerase with an appropriate primer sequence. Where a specific sequence for a nucleic acid probe is given, it is understood that the complementary strand is also identified and included. The complementary strand will work equally well in situations where the target is a double-stranded nucleic acid. It is also understood that when a specific sequence is identified for use a nucleic probe, a subsequence of the listed sequence which is 25 basepairs or more in length is also encompassed for use as a probe.

The DNA molecules of the subject invention also include DNA molecules coding for polypeptide analogs, fragments or derivatives of antigenic polypeptides which differ from naturally-occurring forms in terms of the identity or location of one or more amino acid residues (deletion analogs containing less than all of the residues specified for the protein, substitution analogs wherein one or more residues specified are replaced by other residues and addition analogs where in one or more amino acid residues is added to a terminal or medial portion of the polypeptides) and which share some or all properties of naturally-occurring forms. These molecules include: the incorporation of codons "preferred" for expression by selected non-mammalian hosts; the provision of sites for cleavage by restriction endonuclease enzymes; and the provision of additional initial, terminal or intermediate DNA sequences that facilitate construction of readily expressed vectors.

This invention also provides a method of producing a polypeptide encoded by isolated DNA molecule, which comprises growing the above host vector system under suitable conditions permitting production of the polypeptide and recovering the polypeptide so produced.

This invention provides an isolated polypeptide encoded by the isolated DNA molecule associated with Kaposi's sarcoma. Further, this invention provides a host cell which expresses the polypeptide of isolated DNA molecule.

In one embodiment the isolated polypeptide is encoded by at least a portion of an isolated nucleic acid molecule. In another embodiment the isolated polypeptide is encoded by at least a portion of a nucleic acid molecule with a sequence as set forth in SEQ ID NOs: 1 and 3.

Further, the isolated polypeptide encoded by the isolated DNA molecule may be linked to a second polypeptide encoded by a nucleic acid molecule to form a fusion protein by expression in a suitable host cell. In one embodiment the second nucleic acid molecule encodes beta-galactosidase. Other nucleic acid molecules which are used to form a fusion protein are known to those skilled in the art.

This invention provides an antibody which specifically binds to the polypeptide encoded by the isolated DNA molecule. In one embodiment the antibody is a monoclonal antibody. In another embodiment the antibody is a polyclonal antibody.

The antibody or DNA molecule may be labelled with a detectable marker including, but not limited to: a radioactive label, or a calorimetric, a luminescent, or a fluorescent marker, or gold. Radioactive labels include, but are not limited to: $^{3}$H, $^{14}$C, $^{32}$P, $^{33}$P, $^{35}$S, $^{36}$Cl, $^{51}$Cr, $^{57}$Co, $^{59}$Co, $^{59}$Fe, $^{90}$Y, $^{125}$I, $^{131}$I, and $^{186}$Re. Fluorescent markers include but are not limited to: fluorescein, rhodamine and auramine. Colorimetric markers include, but are not limited to: biotin, and digoxigenin. Methods of producing the polyclonal or monoclonal antibody are known to those of ordinary skill in the art.

Further, the antibody or nucleic acid molecule complex may be detected by a second antibody which may be linked to an enzyme, such as alkaline phosphatase or horseradish peroxidase. Other enzymes which may be employed are well known to one of ordinary skill in the art.

This invention provides a method to select specific regions on the polypeptide encoded by the isolated DNA molecule of the DNA virus to generate antibodies. The protein sequence may be determined from the cDNA sequence. Amino acid sequences may be analyzed by methods well known to those skilled in the art to determine whether they produce hydrophobic or hydrophilic regions in the proteins which they build. In the case of cell membrane proteins, hydrophobic regions are well known to form the part of the protein that is inserted into the lipid bilayer of the cell membrane, while hydrophilic regions are located on the cell surface, in an aqueous environment. Usually, the hydrophilic regions will be more immunogenic than the hydrophobic regions. Therefore the hydrophilic amino acid sequences may be selected and used to generate antibodies specific to polypeptide encoded by the isolated nucleic acid molecule encoding the DNA virus. The selected peptides may be prepared using commercially available machines. As an alternative, DNA, such as a cDNA or a fragment thereof, may be cloned and expressed and the resulting polypeptide recovered and used as an immunogen.

Polyclonal antibodies against these peptides may be produced by immunizing animals using the selected peptides. Monoclonal antibodies are prepared using hybridoma technology by fusing antibody producing B cells from immunized animals with myeloma cells and selecting the resulting hybridoma cell line producing the desired antibody. Alternatively, monoclonal antibodies may be produced by in vitro techniques known to a person of ordinary skill in the art. These antibodies are useful to detect the expression of polypeptide encoded by the isolated DNA molecule of the DNA virus in living animals, in humans, or in biological tissues or fluids isolated from animals or humans.

II. Immunoassays

The antibodies raised against the viral strain or peptides may be detectably labelled, utilizing conventional labelling techniques well-known to the art. Thus, the antibodies may be radiolabelled using, for example, radioactive isotopes such as $^3$H, $^{125}$I, $^{131}$I, and $^{35}$S.

The antibodies may also be labelled using fluorescent labels, enzyme labels, free radical labels, or bacteriophage labels, using techniques known in the art. Typical fluorescent labels include fluorescein isothiocyanate, rhodamine, phycoerythrin, phycocyanin, alophycocyanin, and Texas Red.

Since specific enzymes may be coupled to other molecules by covalent links, the possibility also exists that they might be used as labels for the production of tracer materials. Suitable enzymes include alkaline phosphatase, beta-galactosidase, glucose-6-phosphate dehydrogenase, maleate dehydrogenase, and peroxidase. Two principal types of enzyme immunoassay are the enzyme-linked immunosorbent assay (ELISA), and the homogeneous enzyme immunoassay, also known as enzyme-multiplied immunoassay (EMIT, Syva Corporation, Palo Alto, Calif.). In the ELISA system, separation may be achieved, for example, by the use of antibodies coupled to a solid phase. The EMIT system depends on deactivation of the enzyme in the tracer-antibody complex; the activity can thus be measured without the need for a separation step.

Additionally, chemiluminescent compounds may be used as labels. Typical chemiluminescent compounds include luminol, isoluminol, aromatic acridinium esters, imidazoles, acridinium salts, and oxalate esters. Similarly, bioluminescent compounds may be utilized for labelling, the bioluminescent compounds including luciferin, luciferase, and aequorin.

Once labeled, the antibody may be employed to identify and quantify immunologic counterparts (antibody or antigenic polypeptide) utilizing techniques well-known to the art.

A description of a radioimmunoassay (RIA) may be found in *Laboratory Techniques in Biochemistry and Molecular Biology* [52], with particular reference to the chapter entitled "An Introduction to Radioimmune Assay and Related Techniques" by Chard, T., incorporated by reference herein.

A description of general immunometric assays of various types can be found in the following U.S. Pat. Nos. 4,376,110 (David et al.) or 4,098,876 (Piasio).

A. Assays for viral antigens

In addition to the detection of the causal agent using nucleic acid hybridization technology, one can use immunoassays to detect for the virus, specific peptides, or for antibodies to the virus or peptides. A general overview of the applicable technology is in Harlow and Lane [32], incorporated by reference herein.

In one embodiment, antibodies to the human herpesvirus can be used to detect the agent in the sample. In brief, to produce antibodies to the agent or peptides, the sequence being targeted is expressed in transfected cells, preferably bacterial cells, and purified. The product is injected into a mammal capable of producing antibodies. Either monoclonal or polyclonal antibodies (as well as any recombinant antibodies) specific for the gene product can be used in various immunoassays. Such assays include competitive immunoassays, radioimmunoassays, Western blots, ELISA, indirect immunofluorescent assays and the like. For competitive immunoassays, see Harlow and Lane [32] at pages 567–573 and 584–589.

Monoclonal antibodies or recombinant antibodies may be obtained by various techniques familiar to those skilled in the art. Briefly, spleen cells or other lymphocytes from an animal immunized with a desired antigen are immortalized, commonly by fusion with a myeloma cell (see, Kohler and Milstein [50], incorporated herein by reference). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. New techniques using recombinant phage antibody expression systems can also be used to generate monoclonal antibodies. See for example: McCafferty, J et al. [64]; Hoogenboom, H. R. et al. [39]; and Marks, J. D. et al. [60].

Such peptides may be produced by expressing the specific sequence in a recombinantly engineered cell such as bacteria, yeast, filamentous fungal, insect (especially employing baculoviral vectors), and mammalian cells. Those of skill in the art are knowledgeable in the numerous expression systems available for expression of herpes virus protein.

Briefly, the expression of natural or synthetic nucleic acids encoding viral protein will typically be achieved by operably linking the desired sequence or portion thereof to a promoter (which is either constitutive or inducible), and incorporated into an expression vector. The vectors are suitable for replication or integration in either prokaryotes or eukaryotes. Typical cloning vectors contain antibiotic resistance markers, genes for selection of transformants, inducible or regulatable promoter regions, and translation terminators that are useful for the expression of viral genes.

Methods for the expression of cloned genes in bacteria are also well known. In general, to obtain high level expression of a cloned gene in a prokaryotic system, it is advisable to construct expression vectors containing a strong promoter to direct mRNA transcription. The inclusion of selection markers in DNA vectors transformed in E. coli is also useful. Examples of such markers include genes specifying resistance to antibiotics. See [81] supra, for details concerning selection markers and promoters for use in E. coli. Suitable eukaryote hosts may include plant cells, insect cells, mammalian cells, yeast, and filamentous fungi.

Methods for characterizing naturally processed peptides bound to MHC (major histocompatibility complex) I molecules have been developed. See, Falk et al. [24], and PCT publication No. WO 92/21033 published Nov. 26, 1992, both of which are incorporated by reference herein. Typically, these methods involve isolation of MHC class I molecules by immunoprecipitation or affinity chromatography from an appropriate cell or cell line. Other methods involve direct amino acid sequencing of the more abundant peptides in various HPLC fractions by known automatic sequencing of peptides eluted from Class I molecules of the B cell type (Jardetzkey, et al. [45], incorporated by reference herein, and of the human MHC class I molecule, HLA-A2.1 type by mass spectrometry (Hunt, et al. [40], incorporated by reference herein). See also, Rötzschke and Falk [79], incorporated by reference herein for a general review of the characterization of naturally processed peptides in MHC class I. Further, Marloes, et al. [61], incorporated by reference herein, describe how class I binding motifs can be applied to the identification of potential viral immunogenic peptides in vitro.

The peptides described herein produced by recombinant technology may be purified by standard techniques well known to those of skill in the art. Recombinantly produced viral sequences can be directly expressed or expressed as a fusion protein. The protein is then purified by a combination of cell lysis (e.g., sonication) and affinity chromatography. For fusion products, subsequent digestion of the fusion protein with an appropriate proteolytic enzyme releases the desired peptide.

The proteins may be purified to substantial purity by standard techniques well known in the art, including selective precipitation with such substances as ammonium sulfate, column chromatography, immunopurification methods, and others. See, for instance, Scopes, R. [84], incorporated herein by reference.

B. Serological tests for the presence of antibodies to the human herpesvirus

This invention further embraces diagnostic kits for detecting the presence of a KS agent in biological samples, such as serum or solid tissue samples, comprising a container containing antibodies to the human herpesvirus, and instructional material for performing the test. Alternatively, inactivated viral particles or peptides or viral proteins derived from the human herpesvirus may be used in a diagnostic kit to detect for antibodies specific to the KS associated human herpesvirus.

Diagnostic kits for detecting the presence of a KS agent in tissue samples, such as skin samples or samples of other affected tissue, comprising a container containing a nucleic acid sequence specific for the human herpesvirus and instructional material for detecting the KS-associated herpesvirus are also included. A container containing nucleic acid primers to any one of such sequences is optionally included as are antibodies to the human herpesvirus as described herein.

Antibodies reactive with antigens of the human herpesvirus can also be measured by a variety of immunoassay methods that are similar to the procedures described above for measurement of antigens. For a review of immunological and immunoassay procedures applicable to the measurement of antibodies by immunoassay techniques, see Basic and Clinical Immunology 7th Edition [12], and [32], supra.

In brief, immunoassays to measure antibodies reactive with antigens of the KS-associated human herpesvirus can be either competitive or noncompetitive binding assays. In competitive binding assays, the sample analyte competes with a labeled analyte for specific binding sites on a capture agent bound to a solid surface. Preferably the capture agent is a purified recombinant human herpesvirus protein produced as described above. Other sources of human herpesvirus proteins, including isolated or partially purified naturally occurring protein, may also be used. Noncompetitive assays are typically sandwich assays, in which the sample analyte is bound between two analyte-specific binding reagents. One of the binding agents is used as a capture agent and is bound to a solid surface. The second binding agent is labelled and is used to measure or detect the resultant complex by visual or instrument means. A number of combinations of capture agent and labelled binding agent can be used. A variety of different immunoassay formats, separation techniques and labels can be also be used similar to those described above for the measurement of the human herpesvirus antigens.

Hemagglutination Inhibition (HI) and Complement Fixation (CF) which are two laboratory tests that can be used to detect infection with human herpesvirus by testing for the presence of antibodies against the virus or antigens of the virus.

Serological methods can be also be useful when one wishes to detect antibody to a specific variant. For example, one may wish to see how well a vaccine recipient has responded to the new variant. Alternatively, one may take serum from a patient to see which variant the patient responds to the best.

This invention provides an antagonist capable of blocking the expression of the peptide or polypeptide encoded by the isolated DNA molecule. In one embodiment the antagonist is capable of hybridizing with a double stranded DNA molecule. In another embodiment the antagonist is a triplex oligonucleotide capable of hybridizing to the DNA molecule. In another embodiment the triplex oligonucleotide is capable of binding to at least a portion of the isolated DNA molecule with a nucleotide sequence as shown in FIG. 3A–3F.

This invention provides an antisense molecule capable of hybridizing to the isolated DNA molecule. In one embodiment the antisense molecule is DNA. In another embodiment the antisense molecule is RNA.

The antisense molecule may be DNA or RNA or variants thereof (i.e. DNA or RNA with a protein backbone). The present invention extends to the preparation of antisense nucleotides and ribozymes that may be used to interfere with the expression of the receptor recognition proteins at the translation of a specific mRNA, either by masking that MRNA with an antisense nucleic acid or cleaving it with a ribozyme.

Antisense nucleic acids are DNA or RNA molecules that are complementary to at least a portion of a specific MRNA molecule. In the cell, they hybridize to that MRNA, forming a double stranded molecule. The cell does not translate an MRNA in this double-stranded form. Therefore, antisense nucleic acids interfere with the expression of MRNA into protein. Oligomers of about fifteen nucleotides and molecules that hybridize to the AUG initiation codon are particularly efficient, since they are easy to synthesize and are likely to pose fewer problems than larger molecules upon introduction to cells.

This invention provides a transgenic nonhuman mammal which comprises at least a portion of the isolated DNA molecule introduced into the mammal at an embryonic stage. Methods of producing a transgenic nonhuman mammal are known to those skilled in the art.

This invention provides a cell line containing the isolated KS associated herpesvirus of the subject invention. In one embodiment the isolated DNA molecule is artificially introduced into the cell. Cell lines include, but are not limited to: fibroblasts, such as HFF, NIH/3T3; Epithelial cells, such as 5637; lymphocytes, such as FCB; T-cells, such as CCRF-CEM (ATCC CCL 119); B-cells, such as BJAB and Raji (ATCC CCL 86); and myeloid cells such as K562 (ATCC CCL 243); Vero cells and carcinoma cells. Methods of producing such cell lines are known to those skilled in the art. In one embodiment the isolated KS associated herpesvirus is introduced into a RCC-1 cell line.

III. In vitro diagnostic assays for the detection of KS

This invention provides a method of diagnosing Kaposi's sarcoma in a subject which comprises: (a) obtaining a nucleic acid molecule from a tumor lesion of the subject; (b) contacting the nucleic acid molecule with a labelled nucleic acid molecule of at least 15 nucleotides capable of specifically hybridizing with the isolated DNA, under hybridizing conditions; and (c) determining the presence of the nucleic acid molecule hybridized, the presence of which is indicative of Kaposi's sarcoma in the subject, thereby diagnosing Kaposi's sarcoma in the subject.

In one embodiment the DNA molecule from the tumor lesion is amplified before step (b). In another embodiment PCR is employed to amplify the nucleic acid molecule. Methods of amplifying nucleic acid molecules are known to those skilled in the art.

A person of ordinary skill in the art will be able to obtain appropriate DNA sample for diagnosing Kaposi's sarcoma in the subject. The DNA sample obtained by the above described method may be cleaved by restriction enzyme. The uses of restriction enzymes to cleave DNA and the conditions to perform such cleavage are well-known in the art.

In the above described methods, a size fractionation may be employed which is effected by a polyacrylamide gel. In one embodiment, the size fractionation is effected by an agarose gel. Further, transferring the DNA fragments into a solid matrix may be employed before a hybridization step. One example of such solid matrix is nitrocellulose paper.

This invention provides a method of diagnosing Kaposi's sarcoma in a subject which comprises: (a) obtaining a nucleic acid molecule from a suitable bodily fluid of the subject; (b) contacting the nucleic acid molecule with a labelled nucleic acid molecules of at least 15 nucleotides capable of specifically hybridizing with the isolated DNA, under hybridizing conditions; and (c) determining the presence of the nucleic acid molecule hybridized, the presence of which is indicative of Kaposi's sarcoma in the subject, thereby diagnosing Kaposi's sarcoma in the subject.

This invention provides a method of diagnosing a DNA virus in a subject, which comprises (a) obtaining a suitable bodily fluid sample from the subject, (b) contacting the suitable bodily fluid of the subject to a support having already bound thereto a Kaposi's sarcoma antibody, so as to bind the Kaposi's sarcoma antibody to a specific Kaposi's sarcoma antigen, (c) removing unbound bodily fluid from the support, and (d) determining the level of Kaposi's sarcoma antibody bound by the Kaposi's sarcoma antigen, thereby diagnosing the subject for Kaposi's sarcoma.

This invention provides a method of diagnosing Kaposi's sarcoma in a subject, which comprises (a) obtaining a suitable bodily fluid sample from the subject, (b) contacting the suitable bodily fluid of the subject to a support having already bound thereto a Kaposi's sarcoma antigen, so as to bind Kaposi's sarcoma antigen to a specific Kaposi's sarcoma antibody, (c) removing unbound bodily fluid from the support, and (d) determining the level of the Kaposi's sarcoma antigen bound by the Kaposi's sarcoma antibody, thereby diagnosing Kaposi's sarcoma.

This invention provides a method of detecting expression of a DNA virus associated with Kaposi's sarcoma in a cell which comprises obtaining total cDNA obtained from the cell, contacting the cDNA so obtained with a labelled DNA molecule under hybridizing conditions, determining the presence of cDNA hybridized to the molecule, and thereby detecting the expression of the DNA virus. In one embodiment mRNA is obtained from the cell to detect expression of the DNA virus.

The suitable bodily fluid sample is any bodily fluid sample which would contain Kaposi's sarcoma antibody, antigen or fragments thereof. A suitable bodily fluid includes, but is not limited to: serum, plasma, cerebrospinal fluid, lymphocytes, urine, transudates, or exudates. In the preferred embodiment, the suitable bodily fluid sample is serum or plasma. In addition, the bodily fluid sample may be cells from bone marrow, or a supernatant from a cell culture. Methods of obtaining a suitable bodily fluid sample from a subject are known to those skilled in the art. Methods of determining the level of antibody or antigen include, but are not limited to: ELISA, IFA, and Western blotting. Other methods are known to those skilled in the art. Further, a subject infected with a DNA virus associated with Kaposi's sarcoma may be diagnosed with the above described methods.

The detection of the human herpesvirus and the detection of virus-associated KS are essentially identical processes. The basic principle is to detect the virus using specific ligands that bind to the virus but not to other proteins or nucleic acids in a normal human cell or its environs. The ligands can either be nucleic acid or antibodies. The ligands can be naturally occurring or genetically or physically modified such as nucleic acids with non-natural or antibody derivatives, i.e., Fab or chimeric antibodies. Serological tests for detection of antibodies to the virus may also be performed by using protein antigens obtained from the human herpesvirus, and described herein.

Samples can be taken from patients with KS or from patients at risk for KS, such as AIDS patients. Typically the samples are taken from blood (cells, serum and/or plasma) or from solid tissue samples such as skin lesions. The most accurate diagnosis for KS will occur if elevated titers of the virus are detected in the blood or in involved lesions. KS may also be indicated if antibodies to the virus are detected and if other diagnostic factors for KS is present.

A. Nucleic acid assays

The diagnostic assays of the invention can be nucleic acid assays such as nucleic acid hybridization assays and assays which detect amplification of specific nucleic acid to detect for a nucleic acid sequence of the human herpesvirus described herein.

Accepted means for conducting hybridization assays are known and general overviews of the technology can be had from a review of: *Nucleic Acid Hybridization*: A Practical Approach [72]; Hybridization of Nucleic Acids Immobilized on Solid Supports [41]; *Analytical Biochemistry* [4] and Innis et al., PCR Protocols [74], supra, all of which are incorporated by reference herein.

If PCR is used in conjunction with nucleic acid hybridization, primers are designed to target a specific portion of the nucleic acid of the herpesvirus. For example, the primers set forth in SEQ ID NOs: 38–40 may be used to target detection of regions of the herpesvirus genome encoding ORF 25 homologue—ORF 32 homologue. From the information provided herein, those of skill in the art will be able to select appropriate specific primers.

Target specific probes may be used in the nucleic acid hybridization diagnostic assays for KS. The probes are specific for or complementary to the target of interest. For precise allelic differentiations, the probes should be about 14 nucleotides long and preferably about 20–30 nucleotides. For more general detection of the human herpesvirus of the invention, nucleic acid probes are about 50 to about 1000 nucleotides, most preferably about 200 to about 400 nucleotides.

A sequence is "specific" for a target organism of interest if it includes a nucleic acid sequence which when detected is determinative of the presence of the organism in the presence of a heterogeneous population of proteins and other biologics. A specific nucleic acid probe is targeted to that portion of the sequence which is determinative of the organism and will not hybridize to other sequences especially those of the host where a pathogen is being detected.

The specific nucleic acid probe can be RNA or DNA polynucleotide or oligonucleotide, or their analogs. The probes may be single or double stranded nucleotides. The probes of the invention may be synthesized enzymatically, using methods well known in the art (e.g., nick translation, primer extension, reverse transcription, the polymerase chain reaction, and others) or chemically (e.g., by methods such as the phosphoramidite method described by Beaucage and Carruthers [19], or by the triester method according to Matteucci, et al. [62], both incorporated herein by reference).

The probe must be of sufficient length to be able to form a stable duplex with its target nucleic acid in the sample, i.e., at least about 14 nucleotides, and may be longer (e.g., at least about 50 or 100 bases in length). Often the probe will be more than about 100 bases in length. For example, when probe is prepared by nick-translation of DNA in the presence of labeled nucleotides the average probe length may be about 100–600 bases.

As noted above, the probe will be capable of specific hybridization to a specific KS-associated herpes virus nucleic acid. Such "specific hybridization" occurs when a probe hybridizes to a target nucleic acid, as evidenced by a detectable signal, under conditions in which the probe does not hybridize to other nucleic acids (e.g., animal cell or other bacterial nucleic acids) present in the sample. A variety of factors including the length and base composition of the probe, the extent of base mismatching between the probe and the target nucleic acid, the presence of salt and organic solvents, probe concentration, and the temperature affect hybridization, and optimal hybridization conditions must often be determined empirically. For discussions of nucleic acid probe design and annealing conditions, see, for example, [81], supra, Ausubel, F., et al. [8] [hereinafter referred to as Sambrook], Methods in Enzymology [67] or Hybridization with Nucleic Acid Probes [42] all of which are incorporated herein by reference.

Usually, at least a part of the probe will have considerable sequence identity with the target nucleic acid. Although the extent of the sequence identity required for specific hybridization will depend on the length of the probe and the hybridization conditions, the probe will usually have at least 70% identity to the target nucleic acid, more usually at least 80% identity, still more usually at least 90% identity and most usually at least 95% or 100% identity.

A probe can be identified as capable of hybridizing specifically to its target nucleic acid by hybridizing the probe to a sample treated according the protocol of this invention where the sample contains both target virus and animal cells (e.g., nerve cells). A probe is specific if the probe's characteristic signal is associated with the herpesvirus DNA in the sample and not generally with the DNA of the host cells and non-biological materials (e.g., substrate) in a sample.

The following stringent hybridization and washing conditions will be adequate to distinguish a specific probe (e.g., a fluorescently labeled DNA probe) from a probe that is not specific: incubation of the probe with the sample for 12 hours at 37° C. in a solution containing denatured probe, 50% formamide, 2× SSC, and 0.1% (w/v) dextran sulfate, followed by washing in 1× SSC at 70° C. for 5 minutes; 2× SSC at 37° C. for 5 minutes; 0.2× SSC at room temperature for 5 minutes, and $H_2O$ at room temperature for 5 minutes. Those of skill will be aware that it will often be advantageous in nucleic acid hybridizations (i.e., in situ, Southern, or other) to include detergents (e.g., sodium dodecyl sulfate), chelating agents (e.g., EDTA) or other reagents (e.g., buffers, Denhardt's solution, dextran sulfate) in the hybridization or wash solutions. To test the specificity of the virus specific probes, the probes can be tested on host cells containing the KS-associated herpesvirus and compared with the results from cells containing non-KS-associated virus.

It will be apparent to those of ordinary skill in the art that a convenient method for determining whether a probe is specific for a KS-associated viral nucleic acid utilizes a Southern blot (or Dot blot) using DNA prepared from one or more KS-associated human herpesviruses of the invention. Briefly, to identify a target specific probe DNA is isolated from the virus. Test DNA either viral or cellular is transferred to a solid (e.g., charged nylon) matrix. The probes are labelled following conventional methods. Following denaturation and/or prehybridization steps known in the art, the probe is hybridized to the immobilized DNAs under stringent conditions. Stringent hybridization conditions will depend on the probe used and can be estimated from the calculated Tm (melting temperature) of the hybridized probe (see, e.g., Sambrook for a description of calculation of the $T_m$). For radioactively-labeled DNA or RNA probes an example of stringent hybridization conditions is hybridization in a solution containing denatured probe and 5×SSC at 65° C. for 8–24 hours followed by washes in 0.1×SSC, 0.1% SDS (sodium dodecyl sulfate) at 50°–65° C. In general, the temperature and salt concentration are chosen so that the post hybridization wash occurs at a temperature that is about 5° C. below the $T_M$ of the hybrid. Thus for a particular salt concentration the temperature may be selected that is 5° C. below the $T_M$ or conversely, for a particular temperature, the salt concentration is chosen to provide a $T_M$ for the hybrid that is 5° C. warmer than the wash temperature. Following stringent hybridization and washing, a probe that hybridizes to the KS-associated viral DNA but not to the non-KS associated viral DNA, as evidenced by the presence of a signal associated with the appropriate target and the absence of a signal from the non-target nucleic acids, is identified as specific for the KS associated virus. It is further appreciated that in determining probe specificity and in utilizing the method of this invention to detect KS-associated herpesvirus, a certain amount of background signal is typical and can easily be distinguished by one of skill from a specific signal. Two fold signal over background is acceptable.

A preferred method for detecting the KS-associated herpesvirus is the use of PCR and/or dot blot hybridization. The presence or absence of an KS agent for detection or prognosis, or risk assessment for KS includes Southern transfers, solution hybridization or non-radioactive detection systems, all of which are well known to those of skill in the art. Hybridization is carried out using probes. Visualization of the hybridized portions allows the qualitative determination of the presence or absence of the causal agent.

Similarly, a Northern transfer may be used for the detection of message in samples of RNA or reverse transcriptase PCR and cDNA can be detected by methods described above. This procedure is also well known in the art. See [81] incorporated by reference herein.

An alternative means for determining the presence of the human herpesvirus is in situ hybridization, or more recently, in situ polymerase chain reaction. In situ PCR is described in Neuvo et al. [71], Intracellular localization of polymerase chain reaction (PCR)-amplified Hepatitis C cDNA; Bagasra et al. [10], Detection of Human Immunodeficiency virus type 1 provirus in mononuclear cells by in situ polymerase chain reaction; and Heniford et al. [35], Variation in cellular EGF receptor mRNA expression demonstrated by in situ reverse transcriptase polymerase chain reaction. In situ hybridization assays are well known and are generally described in *Methods Enzymol.* [67] incorporated by reference herein. In an in situ hybridization, cells are fixed to a solid support, typically a glass slide. The cells are then contacted with a hybridization solution at a moderate temperature to permit annealing of target-specific probes that are labelled. The probes are preferably labelled with radioisotopes or fluorescent reporters.

The above described probes are also useful for in-situ hybridization or in order to locate tissues which express this gene, or for other hybridization assays for the presence of this gene or its MRNA in various biological tissues. In-situ hybridization is a sensitive localization method which is not dependent on expression of antigens or native vs. denatured conditions.

Oligonucleotide (oligo) probes, synthetic oligonucleotide probes or riboprobes made from KSHV phagemids/plasmids, are relatively homogeneous reagents and successful hybridization conditions in tissue sections is readily transferable from one probe to another. Commercially synthesized oligonucleotide probes are prepared against the identified genes. These probes are chosen for length (45–65 mers), high G-C content (50–70%) and are screened for uniqueness against other viral sequences in GenBank.

Oligonucleotides are 3'end-labeled with $[\alpha-^{35}S]DATP$ to specific activities in the range of $1\times10^{10}$ dpm/ug using terminal deoxynucleotidyl transferase. Unincorporated labeled nucleotides are removed from the oligo probe by centrifugation through a Sephadex G-25 column or by elution from a Waters Sep Pak C-18 column.

KS tissue embedded in OCT compound and snap frozen in freezing isopentane cooled with dry ice is cut at 6 $\mu$m intervals and thawed onto 3-aminopropyltriethoxysilane treated slides and allowed to air dry. The slides are then be fixed in 4% freshly prepared paraformaldehyde, rinsed in water. Formalin-fixed, paraffin embedded KS tissues cut at 6 $\mu$m and baked onto glass slides can also be used. The sections are then deparaffinized in xylenes and rehydrated through graded alcohols. Prehybridization in 20 mM Tris Ph 7.5, 0.02% Denhardt's solution, 10% dextran sulfate for 30 min at 37° C. is followed by hybridization overnight in a solution of 50% formamide (v/v), 10% dextran sulfate (w/v), 20 mM sodium phosphate (Ph 7.4), 3× SSC, 1× Denhardt's solution, 100 ug/ml salmon sperm DNA, 125 ug/ml yeast tRNA and the oligo probe ($10^6$ cpm/ml) at 42° C. overnight. The slides are washed twice with 2× SSC and twice with 1× SSC for 15 minutes each at room temperature and visualized by autoradiography. Briefly, sections are dehydrated through graded alcohols containing 0.3M ammonium acetate and air dried. The slides are dipped in Kodak NTB2 emulsion, exposed for days to weeks, developed, and counterstained with hematoxylin and eoxin. Alternative immunohistochemical protocols may be employed which are known to those skilled in the art.

IV. Treatment of human herpesvirus-induced KS

This invention provides a method of treating a subject with Kaposi's sarcoma, comprising administering to the subject an effective amount of the antisense molecule capable of hybridizing to the isolated DNA molecule under conditions such that the antisense molecule selectively enters a tumor cell of the subject, so as to treat the subject.

This invention provides a method of inhibiting HIV replication, comprising administering to the subject or treating cells of a subject with an effective amount of a protein which is encoded by a nucleic acid molecule, so as to inhibit replication of HIV. In one embodiment the protein is a KSHV MIP1 homolog.

This invention provides a method for treating a subject with Kaposi's sarcoma (KS) comprising administering to the subject having a human herpesvirus-associated KS a pharmaceutically effective amount of an antiviral agent in a pharmaceutically acceptable carrier, wherein the agent is effective to treat the subject with KS-associated human herpes virus.

Further, this invention provides a method of prophylaxis or treatment for Kaposi's sarcoma (KS) by administering to a patient at risk for KS, an antibody that binds to the human herpesvirus in a pharmaceutically acceptable carrier. In one embodiment the antiviral drug is used to treat a subject with the DNA herpesvirus of the subject invention.

The use of combinations of antiviral drugs and sequential treatments are useful for treatment of herpesvirus infections and will also be useful for the treatment of herpesvirus-induced KS. For example, Snoeck et al. [88], found additive or synergistic effects against CMV when combining anti-herpes drugs (e.g., combinations of zidovudine [3'-azido-3'-deoxythymidine, AZT] with HPMPC, ganciclovir, foscarnet or acyclovir or of HPMPC with other antivirals). Similarly, in treatment of cytomegalovirus retinitis, induction with ganciclovir followed by maintenance with foscarnet has been suggested as a way to maximize efficacy while minimizing the adverse side effects of either treatment alone. An anti-herpetic composition that contains acyclovir and, e.g., 2-acetylpyridine-5-((2-pyridylamino)thiocarbonyl)-thiocarbonohydrazone is described in U.S. Pat. No. 5,175,165 (assigned to Burroughs Wellcome Co.). Combinations of TS-inhibitors and viral TK-inhibitors in antiherpetic medicines are disclosed in U.S. Pat. No. 5,137,724, assigned to Stichting Rega VZW. A synergistic inhibitory effect on EBV replication using certain ratios of combinations of HPMPC with AZT was reported by Lin et al. [56].

U.S. Pat. Nos. 5,164,395 and 5,021,437 (Blumenkopf; Burroughs Wellcome) describe the use of a ribonucleotide reductase inhibitor (an acetylpyridine derivative) for treatment of herpes infections, including the use of the acetylpyridine derivative in combination with acyclovir. U.S. Pat. No. 5,137,724 (Balzari et al. [11]) describes the use of thymilydate synthase inhibitors (e.g., 5-fluoro-uracil and 5-fluro-2'-deoxyuridine) in combination with compounds having viral thymidine kinase inhibiting activity.

With the discovery of a disease causal agent for KS now identified, effective therapeutic or prophalactic protocols to alleviate or prevent the symptoms of herpes virus-associated KS can be formulated. Due to the viral nature of the disease, antiviral agents have application here for treatment, such as interferons, nucleoside analogues, ribavirin, amantadine, and pyrophosphate analogues of phosphonoacetic acid (foscarnet) (reviewed in Gorbach, S. L., et al. [28]) and the like. Immunological therapy will also be effective in many cases to manage and alleviate symptoms caused by the disease agents described here. Antiviral agents include agents or compositions that directly bind to viral products and interfere with disease progress; and, excludes agents that do not impact directly on viral multiplication or viral titer. Antiviral agents do not include immunoregulatory agents that do not directly affect viral titer or bind to viral products. Antiviral agents are effective if they inactivate the virus, otherwise inhibit its infectivity or multiplication, or alleviate the symptoms of KS.

A. Antiviral Agents

The antiherpesvirus agents that will be useful for treating virus-induced KS can be grouped into broad classes based on their presumed modes of action. These classes include agents that act (i) by inhibition of viral DNA polymerase, (ii) by targeting other viral enzymes and proteins, (iii) by miscellaneous or incompletely understood mechanisms, or (iv) by binding a target nucleic acid (i.e., inhibitory nucleic acid therapeutics). Antiviral agents may also be used in combination (i.e., together or sequentially) to achieve synergistic or additive effects or other benefits.

Although it is convenient to group antiviral agents by their supposed mechanism of action, the applicants do not intend to be bound by any particular mechanism of antiviral action. Moreover, it will be understood by those of skill that an agent may act on more than one target in a virus or virus-infected cell or through more than one mechanism.

i) Inhibitors of viral DNA polymerase

Many antiherpesvirus agents in clinical use or in development today are nucleoside analogs believed to act through inhibition of viral DNA replication, especially through inhibition of viral DNA polymerase. These nucleoside analogs act as alternative substrates for the viral DNA polymerase or as competitive inhibitors of DNA polymerase substrates. Usually these agents are preferentially phosphorylated by viral thymidine kinase (TK), if one is present, and/or have higher affinity for viral DNA polymerase than for the cellular DNA polymerases, resulting in selective antiviral activity. Where a nucleoside analogue is incorporated into the viral DNA, viral activity or reproduction may be affected in a variety of ways. For example, the analogue may act as a chain terminator, cause increased lability (e.g., susceptibility to breakage) of analogue-containing DNA, and/or impair the ability of the substituted DNA to act as template for transcription or replication (see, e.g., Balzarini et al. [11]).

It will be known to one of skill that, like many drugs, many of the agents useful for treatment of herpes virus infections are modified (i.e., "activated") by the host, host cell, or virus-infected host cell metabolic enzymes. For example, acyclovir is triphosphorylated to its active form, with the first phosphorylation being carried out by the herpes virus thymidine kinase, when present. Other examples are the reported conversion of the compound HOE 602 to ganciclovir in a three-step metabolic pathway (Winkler et al. [95]) and the phosphorylation of ganciclovir to its active form by, e.g., a CMV nucleotide kinase. It will be apparent to one of skill that the specific metabolic capabilities of a virus can affect the sensitivity of that virus to specific drugs, and is one factor in the choice of an antiviral drug. The mechanism of action of certain anti-herpesvirus agents is discussed in De Clercq [22] and in other references cited supra and infra, all of which are incorporated by reference herein.

Anti-herpesvirus medications suitable for treating, viral induced KS include, but are not limited to, nucleoside analogs including acyclic nucleoside 60 phosphonate analogs (e.g., phosphonylmethoxyalkylpurines and -pyrimidines), and cyclic nucleoside analogs. These include drugs such as: vidarabine (9-β-D-arabinofuranosyladenine; adenine arabinoside, ara-A, Vira-A, Parke-Davis); 1-β-D-arabinofuranosyluracil (ara-U); 1-β-D-arabinofuranosyl-cytosine (ara-C); HPMPC [(S)-1-[3-hydroxy-2-(phosphonylmethoxy)propyl]cytosine (e.g., GS 504 Gilead Science)] and its cyclic form (cHPMPC); HPMPA [(S)-9-(3-hydroxy-2-phosphonylmethoxypropyl)adenine] and its cyclic form (cHPMPA); (S)-HPMPDAP [(S)-9-(3-hydroxy-2-phosphonylmethoxypropyl)-2,6-diaminopurine]; PMEDAP [9- (2-phosphonyl-methoxyethyl) -2,6-diaminopurine]; HOE 602 [2-amino-9-(1,3-bis(isopropoxy) -2-propoxymethyl)purine]; PMEA [9-(2-phosphonylmethoxyethyl)adenine]; bromovinyl-deoxyuridine (Burns and Sandford. [21]); 1-β-D-arabinofuranosyl-E-5-(2-bromovinyl)-uridine or -2'-deoxyuridine; BVaraU (1-β-D-arabinofuranosyl-E-5-(2-bromovinyl)-uracil, brovavir, Bristol-Myers Squibb, Yamsa Shoyu); BVDU [(E)-5-(2-bromovinyl)-2'-deoxyuridine, brivudin, e.g., Helpin] and its carbocyclic analogue (in which the sugar moiety is replaced by a cyclopentane ring); IVDU [(E)-5-(2-iodovinyl)-2'-deoxyuridine] and its carbocyclic analogue, C-IVDU (Balzarini et al. [11])]; and 5-mercutithio analogs of 2'-deoxyuridine (Holliday, J., and Williams, M. V. [38]); acyclovir [9-([2-hydroxyethoxy] methyl)guanine; e.g., Zovirax (Burroughs Wellcome)]; penciclovir (9-[4-hydroxy-2-(hydroxymethyl)butyl]-guanine); ganciclovir [(9-[1,3-dihydroxy-2 propoxymethyl]-guanine) e.g., Cymevene, Cytovene (Syntex), DHPG (Stals et al. [89]]; isopropylether derivatives of ganciclovir (see, e.g., Winkelmann et al. [94]); cygalovir; famciclovir [2-amino-9-(4-acetoxy-3-(acetoxymethyl)but-1-yl)purine (Smithkline Beecham)]; valacyclovir (Burroughs Wellcome); desciclovir [(2-amino-9-(2-ethoxymethyl)purine)] and 2-amino-9-(2-hydroxyethoxymethyl)-9H-purine, prodrugs of acyclovir]; CDG (carbocyclic 2'-deoxyguanosine); and purine nucleosides with the pentafuranosyl ring replaced by a cyclo butane ring (e.g., cyclobut-A [(+-)-9- [1β, 2α, 3β)-2,3-bis (hydroxymethyl)-1-cyclobutyl]adenine], cyclobut-G [(+-)-9-[1β, 2α, 3β)-2,3-bis(hydroxymethyl)-1-cyclobutyl] guanine], BHCG [(R)-(1α, 2β, 1α)-9-(2,3-bis (hydroxymethyl)cyclobutyl] guanine], and an active isomer of racemic BHCG, SQ 34,514 [1R-1α,2β,3α)-2-amino-9-[2,3-bis(hydroxymethyl)cyclobutyl] -6H-purin-6-one (see, Braitman et al. (1991) [20]]. Certain of these antiherpesviral agents are discussed in Gorach et al. [28]; Saunders et al. [82]; Yamanaka et al., [96]; Greenspan et al. [29], all of which are incorporated by reference herein.

Triciribine and triciribine monophosphate are potent inhibitors against herpes viruses. (Ickes et al. [43], incorporated by reference herein), HIV-1 and HIV-2 (Kucera et al. [51], incorporated by reference herein) and are additional nucleoside analogs that may be used to treat KS. An exemplary protocol for these agents is an intravenous injection of about 0.35 mg/meter$^2$ (0.7 mg/kg) once weekly or every other week for at least two doses, preferably up to about four to eight weeks.

Acyclovir and ganciclovir are of interest because of their accepted use in clinical settings. Acyclovir, an acyclic analogue of guanine, is phosphorylated by a herpesvirus thymidine kinase and undergoes further phosphorylation to be incorporated as a chain terminator by the viral DNA polymerase during viral replication. It has therapeutic activity against a broad range of herpesviruses, Herpes simplex Types 1 and 2, Varicella- Zoster, Cytomegalovirus, and Epstein-Barr Virus, and is used to treat disease such as herpes encephalitis, neonatal herpesvirus infections, chickenpox in immunocompromised hosts, herpes zoster recurrences, CMV retinitis, EBV infections, chronic fatigue syndrome, and hairy leukoplakia in AIDS patients. Exemplary intravenous dosages or oral dosages are 250 mg/kg/m$^2$ body surface area, every 8 hours for 7 days, or maintenance doses of 200–400 mg IV or orally twice a day to suppress recurrence. Ganciclovir has been shown to be more active than acyclovir against some herpesviruses. See, e.g., Oren and Soble [73]. Treatment protocols for ganciclovir are 5 mg/kg twice a day IV or 2.5 mg/kg three times a day for 10–14 days. Maintenance doses are 5–6 mg/kg for 5–7 days.

Also of interest is HPMPC. HPMPC is reported to be more active than either acyclovir or ganciclovir in the chemotherapy and prophylaxis of various HSV-1, HSV-2, TK- HSV, VZV or CMV infections in animal models ([22], supra).

Nucleoside analogs such as BVaraU are potent inhibitors of HSV-1, EBV, and VZV that have greater activity than acyclovir in animal models of encephalitis. FIAC (fluroidoarbinosyl cytosine) and its related fluroethyl and iodo compounds (e.g., FEAU, FIAU) have potent selective activity against herpesviruses, and HPMPA ((S)-1-([3-hydroxy-2-phosphorylmethoxy]propyl)adenine) has been demonstrated to be more potent against HSV and CMV than acyclovir or ganciclovir and are of choice in advanced cases of KS. Cladribine (2-chlorodeoxyadenosine) is another nucleoside analogue known as a highly specific antilymphocyte agent (i.e., a immunosuppressive drug).

Other useful antiviral agents include: 5-thien-2-yl-2'-deoxyuridine derivatives, e.g., BTDU [5-5(5-bromothien-2-yl)-2'-deoxyuridine] and CTDU [b-(5-chlorothien-2-yl)-2'-deoxyuridine]; and OXT-A [9-(2-deoxy-2-hydroxymethyl-β-D-erythro-oxetanosyl)adenine] and OXT-G [9-(2-deoxy-2-hydroxymethyl-β-D-erythro-oxetanosyl)guanine]. Although OXT-G is believed to act by inhibiting viral DNA synthesis its mechanism of action has not yet been elucidated. These and other compounds are described in Andrei et al. [5] which is incorporated by reference herein. Additional antiviral purine derivatives useful in treating herpesvirus infections are disclosed in U.S. Pat. No. 5,108,994 (assigned to Beecham Group P.L.C.). 6-Methoxypurine arabinoside (ara-M; Burroughs Wellcome) is a potent inhibitor of varicella-zoster virus, and will be useful for treatment of KS.

Certain thymidine analogs [e.g., idoxuridine (5-ido-2'-deoxyuridine)] and triflurothymidine) have antiherpes viral activity, but due to their systemic toxicity, are largely used for topical herpesviral infections, including HSV stromal keratitis and uveitis, and are not preferred here unless other options are ruled out.

Other useful antiviral agents that have demonstrated antiherpes viral activity include foscarnet sodium (trisodium phosphonoformate, PFA, Foscavir (Astra)) and phosphonoacetic acid (PAA). Foscarnet is an inorganic pyrophosphate analogue that acts by competitively blocking the pyrophosphate-binding site of DNA polymerase. These agents which block DNA polymerase directly without processing by viral thymidine kinase. Foscarnet is reported to be less toxic than PAA.

ii) Agents that target viral proteins other than DNA polymerase or other viral functions Although applicants do not intend to be bound by a particular mechanism of antiviral action, the antiherpesvirus agents described above are believed to act through inhibition of viral DNA polymerase. However, viral replication requires not only the replication of the viral nucleic acid but also the production of viral proteins and other essential components. Accordingly, the present invention contemplates treatment of KS by the inhibition of viral proliferation by targeting viral proteins other than DNA polymerase (e.g., by inhibition of their synthesis or activity, or destruction of viral proteins after their synthesis). For example, administration of agents that inhibit a viral serine protease, e.g., such as one important in development of the viral capsid will be useful in treatment of viral induced KS.

Other viral enzyme targets include: OMP decarboxylase inhibitors (a target of, e.g., parazofurin), CTP synthetase inhibitors (targets of, e.g., cyclopentenylcytosine), IMP dehydrogenase, ribonucleotide reductase (a target of, e.g., carboxyl-containing N-alkyldipeptides as described in U.S. Pat. No. 5,110,799 (Tolman et al., Merck)), thymidine kinase (a target of, e.g., 1-[2-(hydroxymethyl) cycloalkylmethyl]-5-substituted -uracils and -guanines as described in, e.g., U.S. Pat. Nos. 4,863,927 and 4,782,062 (Tolman et al.; Merck)) as well as other enzymes. It will be apparent to one of ordinary skill in the art that there are additional viral proteins, both characterized and as yet to be discovered, that can serve as target for antiviral agents.

iv) Other agents and modes of antiviral action

Kutapressin is a liver derivative available from Schwarz Parma of Milwaukee, Wisconsin in an injectable form of 25 mg/ml. The recommended dosage for herpesviruses is from 200 to 25 mg/ml per day for an average adult of 150 pounds.

Poly(I) Poly($Cl_{12}U$), an accepted antiviral drug known as Ampligen from HEM Pharmaceuticals of Rockville, MD has been shown to inhibit herpesviruses and is another antiviral agent suitable for treating KS. Intravenous injection is the preferred route of administration. Dosages from about 100 to 600 mg/M$^2$ are administered two to three times weekly to adults averaging 150 pounds. It is best to administer at least 200 mg/m$^2$ per week.

Other antiviral agents reported to show activity against herpes viruses (e.g., varicella zoster and herpes simplex) and will be useful for the treatment of herpesvirus-induced KS include mappicine ketone (SmithKline Beecham); Compounds A, 79296 and A, 73209 (Abbott) for varicella zoster, and Compound 882C87 (Burroughs Wellcome) [see, The Pink Sheet 55(20) May 17, 1993].

Interferon is known inhibit replication of herpes viruses. See [73], supra. Interferon has known toxicity problems and it is expected that second generation derivatives will soon be available that will retain interferon's antiviral properties but have reduced side affects.

It is also contemplated that herpes virus-induced KS may be treated by administering a herpesvirus reactivating agent to induce reactivation of the latent virus. Preferably the reactivation is combined with simultaneous or sequential administration of an anti-herpesvirus agent. Controlled reactivation over a short period of time or reactivation in the presence of an antiviral agent is believed to minimize the adverse effects of certain herpesvirus infections (e.g., as discussed in PCT Application WO 93/04683). Reactivating agents include agents such as estrogen, phorbol esters, forskolin and β-adrenergic blocking agents.

Agents useful for treatment of herpesvirus infections and for treatment of herpesvirus-induced KS are described in numerous U.S. Patents. For example, ganciclovir is an example of a antiviral guanine acyclic nucleotide of the type described in U.S. Pat. Nos. 4,355,032 and 4,603,219.

Acyclovir is an example of a class of antiviral purine derivatives, including 9-(2-hydroxyethylmethyl)adenine, of the type described in U.S. Pat. Nos. 4,287,188, 4,294,831 and 4,199,574.

Brivudin is an example of an antiviral deoxyuridine derivative of the type described in U.S. Pat. No. 4,424,211.

Vidarabine is an example of an antiviral purine nucleoside of the type described in British Pat. 1,159,290.

Brovavir is an example of an antiviral deoxyuridine derivative of the type described in U.S. Pat. Nos. 4,542,210 and 4,386,076.

BHCG is an example of an antiviral carbocyclic nucleoside analogue of the type described in U.S. Pat. Nos. 5,153,352, 5,034,394 and 5,126,345.

HPMPC is an example of an antiviral phosphonyl methoxyalkyl derivative with of the type described in U.S. Pat. No. 5,142,051.

CDG (Carbocyclic 2'-deoxyguanosine) is an example of an antiviral carbocyclic nucleoside analogue of the type described in U.S. Pat. Nos. 4,543,255, 4,855,466, and 4,894,458.

Foscarnet is described in U.S. Pat. No. 4,339,445.

Trifluridine and its corresponding ribonucleoside is described in U.S. Pat. No. 3,201,387.

U.S. Pat. No. 5,321,030 (Kaddurah-Daouk et al.; Amira) describes the use of creatine analogs as antiherpes viral agents. U.S. Pat. No. 5,306,722 (Kim et al.; Bristol-Meyers Squibb) describes thymidine kinase inhibitors useful for treating HSV infections and for inhibiting herpes thymidine kinase. Other antiherpesvirus compositions are described in U.S. Pat. Nos. 5,286,649 and 5,098,708 (Konishi et al., Bristol-Meyers Squibb) and 5,175,165 (Blumenkopf et al.; Burroughs Wellcome). U.S. Pat. No. 4,880,820 (Ashton et al.; Merck) describes the antiherpes virus agent (S)-9-(2,3-dihydroxy-1-propoxymethyl)guanine.

U.S. Pat. No. 4,708,935 (Suhadolnik et al.; Research Corporation) describes a 3'-deoxyadenosine compound effective in inhibiting HSV and EBV. U.S. Pat. No. 4,386,076 (Machida et al.; Yamasa Shoyu Kabushiki Kaisha) describes use of (E)-5-(2-halogenovinyl)-arabinofuranosyluracil as an ahtiherpesvirus agent. U.S. Pat. No. 4,340,599 (Lieb et al.; Bayer Aktiengesellschaft) describes phosphonohydroxyacetic acid derivatives useful as antiherpes agents. U.S. Pat. Nos. 4,093,715 and 4,093,716 (Lin et al. Research Corporation) describe 5'-amino-5'-deoxythymidine and 5-iodo-5'-amino-2',5'-dideoxycytidine as potent inhibitors of herpes simplex virus. U.S. Pat. No. 4,069,382 (Baker et al.; Parke, Davis & Company) describes 9-(5-O-Acyl-beta-D-arabinofuranosyl) adenine compounds useful as antiviral agents. U.S. Pat. No. 3,927,216 (Witkowski et al.) describes the use of 1,2,4-triazole-3-carboxamide and 1,2,4-triazole-3-thiocarboxamide for inhibiting herpes virus infections. U.S. Pat. No. 5,179,093 (Afonso et al., Schering) describes quinoline-2,4-dione derivatives active against herpes simplex virus 1 and 2, cytomegalovirus and Epstein Barr virus.

v) Inhibitory nucleic acid therapeutics

Also contemplated here are inhibitory nucleic acid therapeutics which can inhibit the activity of herpesviruses in patients with KS. Inhibitory nucleic acids may be single-stranded nucleic acids, which can specifically bind to a complementary nucleic acid sequence. By binding to the appropriate target sequence, an RNA-RNA, a DNA-DNA, or RNA-DNA duplex or triplex is formed. These nucleic acids are often termed "antisense" because they are usually complementary to the sense or coding strand of the gene, although recently approaches for use of "sense" nucleic acids have also been developed. The term "inhibitory nucleic acids" as used herein, refers to both "sense" and "antisense" nucleic acids.

By binding to the target nucleic acid, the inhibitory nucleic acid can inhibit the function of the target nucleic acid. This could, for example, be a result of blocking DNA transcription, processing or poly(A) addition to mRNA, DNA replication, translation, or promoting inhibitory mechanisms of the cells, such as promoting RNA degradation. Inhibitory nucleic acid methods therefore encompass a number of different approaches to altering expression of herpesvirus genes. These different types of inhibitory nucleic acid technology are described in Helene, C. and Toulme, J. [34], which is hereby incorporated by reference and is referred to hereinafter as "Helene and Toulme."

In brief, inhibitory nucleic acid therapy approaches can be classified into those that target DNA sequences, those that target RNA sequences (including pre-mRNA and mRNA), those that target proteins (sense strand approaches), and those that cause cleavage or chemical modification of the target nucleic acids.

Approaches targeting DNA fall into several categories. Nucleic acids can be designed to bind to the major groove of the duplex DNA to form a triple helical or "triplex" structure. Alternatively, inhibitory nucleic acids are designed to bind to regions of single stranded DNA resulting from the opening of the duplex DNA during replication or transcription. See Helene and Toulme.

More commonly, inhibitory nucleic acids are designed to bind to mRNA or mRNA precursors. Inhibitory nucleic acids are used to prevent maturation of pre-mRNA. Inhibitory nucleic acids may be designed to interfere with RNA processing, splicing or translation.

The inhibitory nucleic acids can be targeted to mRNA. In this approach, the inhibitory nucleic acids are designed to designed to specifically block translation of the encoded protein. Using this approach, the inhibitory nucleic acid can be used to selectively suppress certain cellular functions by inhibition of translation of mRNA encoding critical proteins. For example, an inhibitory nucleic acid complementary to regions of c-myc mRNA inhibits c-myc protein expression in a human promyelocytic leukemia cell line, HL60, which overexpresses the c-myc proto-oncogene. See Wickstrom E. L., et al. [93] and Harel-Bellan, A., et al. [31A]. As described in Helene and Toulme, inhibitory nucleic acids targeting mRNA have been shown to work by several different mechanisms to inhibit translation of the encoded protein(s).

The inhibitory nucleic acids introduced into the cell can also encompass the "sense" strand of the gene or mRNA to trap or compete for the enzymes or binding proteins involved in mRNA translation. See Helene and Toulme.

Lastly, the inhibitory nucleic acids can be used to induce chemical inactivation or cleavage of the target genes or MRNA. Chemical inactivation can occur by the induction of crosslinks between the inhibitory nucleic acid and the target nucleic acid within the cell. Other chemical modifications of the target nucleic acids induced by appropriately derivatized inhibitory nucleic acids may also be used.

Cleavage, and therefore inactivation, of the target nucleic acids may be effected by attaching a substituent to the inhibitory nucleic acid which can be activated to induce cleavage reactions. The substituent can be one that affects either chemical, or enzymatic cleavage. Alternatively, cleavage can be induced by the use of ribozymes or catalytic RNA. In this approach, the inhibitory nucleic acids would comprise either naturally occurring RNA (ribozymes) or synthetic nucleic acids with catalytic activity.

The targeting of inhibitory nucleic acids to specific cells of the immune system by conjugation with targeting moieties binding receptors on the surface of these cells can be used for all of the above forms of inhibitory nucleic acid therapy. This invention encompasses all of the forms of inhibitory nucleic acid therapy as described above and as described in Helene and Toulme.

This invention relates to the targeting of inhibitory nucleic acids to sequences the human herpesvirus of the invention for use in treating KS. An example of an antiherpes virus inhibitory nucleic acid is ISIS 2922 (ISIS Pharmaceuticals) which has activity against CMV [see, *Biotechnology News* 14(14) p. 5].

A problem associated with inhibitory nucleic acid therapy is the effective delivery of the inhibitory nucleic acid to the target cell in vivo and the subsequent internalization of the inhibitory nucleic acid by that cell. This can be accomplished by linking the inhibitory nucleic acid to a targeting moiety to form a conjugate that binds to a specific receptor on the surface of the target infected cell, and which is internalized after binding.

iii) Administration

The subjects to be treated or whose tissue may be used herein may be a mammal, or more specifically a human, horse, pig, rabbit, dog, monkey, or rodent. In the preferred embodiment the subject is a human.

The compositions are administered in a manner compatible with the dosage formulation, and in a therapeutically effective amount. Precise amounts of active ingredient required to be administered depend on the judgment of the practitioner and are peculiar to each subject.

Suitable regimes for initial administration and booster shots are also variable, but are typified by an initial administration followed by repeated doses at one or more hour intervals by a subsequent injection or other administration.

As used herein administration means a method of administering to a subject. Such methods are well known to those skilled in the art and include, but are not limited to, administration topically, parenterally, orally, intravenously, intramuscularly, subcutaneously or by aerosol. Administration of the agent may be effected continuously or intermittently such that the therapeutic agent in the patient is effective to treat a subject with Kaposi's sarcoma or a subject infected with a DNA, virus associated with Kaposi's sarcoma.

The antiviral compositions for treating herpesvirus-induced KS are preferably administered to human patients via oral, intravenous or parenteral administrations and other systemic forms. Those of skill in the art will understand appropriate administration protocol for the individual compositions to be employed by the physician.

The pharmaceutical formulations or compositions of this invention may be in the dosage form of solid, semi-solid, or liquid such as, e.g., suspensions, aerosols or the like. Preferably the compositions are administered in unit dosage forms suitable for single administration of precise dosage amounts. The compositions may also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological saline, Ringer's solution, dextrose solution, and Hank's solution. In addition, the pharmaceutical composition or formulation may also include other carriers, adjuvants; or nontoxic, nontherapeutic, nonimmunogenic stabilizers and the like. Effective amounts of such diluent or carrier are those amounts which are effective to obtain a pharmaceutically acceptable formulation in terms of solubility of components, or biological activity, etc.

V. Immunological Approaches to Therapy

Having identified a primary causal agent of KS in humans as a novel human herpesvirus, there are immunosuppressive therapies that can modulate the immunologic dysfunction that arises from the presence of viral infected tissue. In particular, agents that block the immunological attack of the viral infected cells will ameliorate the symptoms of KS and/or reduce the disease progress. Such therapies include antibodies that specifically block the targeting of viral infected cells. Such agents include antibodies which bind to cytokines that upregulate the immune system to target viral infected cells.

The antibody may be administered to a patient either singly or in a cocktail containing two or more antibodies, other therapeutic agents, compositions, or the like, including, but not limited to, immuno-suppressive agents, potentiators and side-effect relieving agents. Of particular interest are immuno-suppressive agents useful in suppressing allergic reactions of a host. Immunosuppressive agents of interest include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Potentiators of interest include monensin, ammonium chloride and chloroquine. All of these agents are administered in generally accepted efficacious dose ranges such as those disclosed in the Physician Desk Reference, 41st Ed. (1987), Publisher Edward R. Barnhart, New Jersey.

Immune globulin from persons previously infected with human herpesviruses or related viruses can be obtained using standard techniques. Appropriate titers of antibodies are known for this therapy and are readily applied to the treatment of KS. Immune globulin can be administered via parenteral injection or by intrathecal shunt. In brief, immune globulin preparations may be obtained from individual donors who are screened for antibodies to the KS-associated human herpesvirus, and plasmas from high-titered donors are pooled. Alternatively, plasmas from donors are pooled and then tested for antibodies to the human herpesvirus of the invention; high-titered pools are then selected for use in KS patients.

Antibodies may be formulated into an injectable preparation. Parenteral formulations are known and are suitable for use in the invention, preferably for i.m. or i.v. administration. The formulations containing therapeutically effective amounts of antibodies or immunotoxins are either sterile liquid solutions, liquid suspensions or lyophilized versions and optionally contain stabilizers or excipients. Lyophilized compositions are reconstituted with suitable diluents, e.g., water for injection, saline, 0.3% glycine and the like, at a level of about from 0.01 mg/kg of host body weight to 10 mg/kg where appropriate. Typically, the pharmaceutical compositions containing the antibodies or immunotoxins will be administered in a therapeutically effective dose in a range of from about 0.01 mg/kg to about 5 mg/kg of the treated mammal. A preferred therapeutically effective dose of the pharmaceutical composition containing antibody or immunotoxin will be in a range of from about 0.01 mg/kg to about 0.5 mg/kg body weight of the treated mammal administered over several days to two weeks by daily intravenous infusion, each given over a one hour period, in a sequential patient dose-escalation regimen.

Antibody may be administered systemically by injection i.m., subcutaneously or intraperitoneally or directly into KS lesions. The dose will be dependent upon the properties of the antibody or immunotoxin employed, e.g., its activity and biological half-life, the concentration of antibody in the formulation, the site and rate of dosage, the clinical tolerance of the patient involved, the disease afflicting the patient and the like as is well within the skill of the physician.

The antibody of the present invention may be administered in solution. The pH of the solution should be in the range of pH 5 to 9.5, preferably pH 6.5 to 7.5. The antibody or derivatives thereof should be in a solution having a suitable pharmaceutically acceptable buffer such as phosphate, tris (hydroxymethyl) aminomethane-HCl or citrate and the like. Buffer concentrations should be in the range of 1 to 100 mM. The solution of antibody may also contain a salt, such as sodium chloride or potassium chloride in a concentration of 50 to 150 mM. An effective amount of a stabilizing agent such as an albumin, a globulin, a gelatin, a protamine or a salt of protamine may also be included and may be added to a solution containing antibody or immunotoxin or to the composition from which the solution is prepared.

Systemic administration of antibody is made daily, generally by intramuscular injection, although intravascular infusion is acceptable. Administration may also be intranasal or by other nonparenteral routes. Antibody or immunotoxin may also be administered via microspheres, liposomes or other microparticulate delivery systems placed in certain tissues including blood.

In therapeutic applications, the dosages of compounds used in accordance with the invention vary depending on the class of compound and the condition being treated. The age, weight, and clinical condition of the recipient patient; and the experience and judgment of the clinician or practitioner administering the therapy are among the factors affecting the selected dosage. For example, the dosage of an immunoglobulin can range from about 0.1 milligram per kilogram of body weight per day to about 10 mg/kg per day for polyclonal antibodies and about 5% to about 20% of that amount for monoclonal antibodies. In such a case, the immunoglobulin can be administered once daily as an intravenous infusion. Preferably, the dosage is repeated daily until either a therapeutic result is achieved or until side effects warrant discontinuation of therapy. Generally, the dose should be sufficient to treat or ameliorate symptoms or signs of KS without producing unacceptable toxicity to the patient.

An effective amount of the compound is that which provides either subjective relief of a symptom(s) or an objectively identifiable improvement as noted by the clinician or other qualified observer. The dosing range varies with the compound used, the route of administration and the potency of the particular compound.

VI. Vaccines and Prophylaxis for KS

This invention provides a method of vaccinating a subject against Kaposi's sarcoma, comprising administering to the subject an effective amount of the peptide or polypeptide encoded by the isolated DNA molecule, and a suitable acceptable carrier, thereby vaccinating the subject. In one embodiment naked DNA is administering to the subject in an effective amount to vaccinate a subject against Kaposi's sarcoma.

This invention provides a method of immunizing a subject against a disease caused by the DNA herpesvirus associated with Kaposi's sarcoma which comprises administering to the subject an effective immunizing dose of the isolated herpesvirus subunit vaccine.

A. Vaccines

The invention also provides substances suitable for use as vaccines for the prevention of KS and methods for administering them. The vaccines are directed against the human herpesvirus of the invention, and most preferably comprise antigen obtained from the KS-associated human herpesvirus.

Vaccines can be made recombinantly. Typically, a vaccine will include from about 1 to about 50 micrograms of antigen or antigenic protein or peptide. More preferably, the amount of protein is from about 15 to about 45 micrograms. Typically, the vaccine is formulated so that a dose includes about 0.5 milliliters. The vaccine may be administered by any route known in the art. Preferably, the route is parenteral. More preferably, it is subcutaneous or intramuscular.

There are a number of strategies for amplifying an antigen's effectiveness, particularly as related to the art of vaccines. For example, cyclization or circularization of a peptide can increase the peptide's antigenic and immunogenic potency. See U.S. Pat. No. 5,001,049 which is incorporated by reference herein. More conventionally, an antigen can be conjugated to a suitable carrier, usually a protein molecule. This procedure has several facets. It can allow multiple copies of an antigen, such as a peptide, to be conjugated to a single larger carrier molecule. Additionally, the carrier may possess properties which facilitate transport, binding, absorption or transfer of the antigen.

For parenteral administration, such as subcutaneous injection, examples of suitable carriers are the tetanus toxoid, the diphtheria toxoid, serum albumin and lamprey, or keyhole limpet, hemocyanin because they provide the resultant conjugate with minimum genetic restriction. Conjugates including these universal carriers can function as T cell clone activators in individuals having very different gene sets.

The conjugation between a peptide and a carrier can be accomplished using one of the methods known in the art.

Specifically, the conjugation can use bifunctional cross-linkers as binding agents as detailed, for example, by Means and Feeney, "A recent review of protein modification techniques," Bioconjugate Chem. 1:2–12 (1990).

Vaccines against a number of the Herpesviruses have been successfully developed. Vaccines against Varicella-Zoster Virus using a live attenuated Oka strain is effective in preventing herpes zoster in the elderly, and in preventing chickenpox in both immunocompromised and normal children (Hardy, I., et al. [30]; Hardy, I. et al. [31]; Levin, M. J. et al. [54]; Gershon, A. A. [26]. Vaccines against Herpes simplex Types 1 and 2 are also commercially available with some success in protection against primary disease, but have been less successful in preventing the establishment of latent infection in sensory ganglia (Roizman, B. [78]; Skinner, G. R. et al. [87]).

Vaccines against the human herpesvirus can be made by isolating extracellular viral particles from infected cell cultures, inactivating the virus with formaldehyde followed by ultracentrifugation to concentrate the viral particles and remove the formaldehyde, and immunizing individuals with 2 or 3 doses containing $1 \times 10^9$ virus particles (Skinner, G. R. et al. [86]). Alternatively, envelope glycoproteins can be expressed in E. coli or transfected into stable mammalian cell lines, the proteins can be purified and used for vaccination (Lasky, L. A. [53]). MHC-binding peptides from cells infected with the human herpesvirus can be identified for vaccine candidates per the methodology of [61], supra.

The antigen may be combined or mixed with various solutions and other compounds as is known in the art. For example, it may be administered in water, saline or buffered vehicles with or without various adjuvants or immunodiluting agents. Examples of such adjuvants or agents include aluminum hydroxide, aluminum phosphate, aluminum potassium sulfate (alum), beryllium sulfate, silica, kaolin, carbon, water-in-oil emulsions, oil-in-water emulsions, muramyl dipeptide, bacterial endotoxin, lipid X, Corynebacterium parvum (Propionibacterium acnes), Bordetella pertussis, polyribonucleotides, sodium alginate, lanolin, lysolecithin, vitamin A, saponin, liposomes, levamisole, DEAE-dextran, blocked copolymers or other synthetic adjuvants. Such adjuvants are available commercially from various sources, for example, Merck Adjuvant 65 (Merck and Company, Inc., Rahway, N.J.) or Freund's Incomplete Adjuvant and Complete Adjuvant (Difco Laboratories, Detroit, Michigan). Other suitable adjuvants are Amphigen (oil-in-water), Alhydrogel (aluminum hydroxide), or a mixture of Amphigen and Alhydrogel. Only aluminum is approved for human use.

The proportion of antigen and adjuvant can be varied over a broad range so long as both are present in effective amounts. For example, aluminum hydroxide can be present in an amount of about 0.5% of the vaccine mixture ($Al_2O_3$ basis). On a per-dose basis, the amount of the antigen can range from about 0.1 $\mu$g to about 100 $\mu$g protein per patient. A preferable range is from about 1 $\mu$g to about 50 $\mu$g per dose. A more preferred range is about 15 $\mu$g to about 45 $\mu$g. A suitable dose size is about 0.5 ml. Accordingly, a dose for intramuscular injection, for example, would comprise 0.5 ml containing 45 $\mu$g of antigen in admixture with 0.5% aluminum hydroxide. After formulation, the vaccine may be incorporated into a sterile container which is then sealed and stored at a low temperature, for example 4° C., or it may be freeze-dried. Lyophilization permits long-term storage in a stabilized form.

The vaccines may be administered by any conventional method for the administration of vaccines including oral and parenteral (e.g., subcutaneous or intramuscular) injection. Intramuscular administration is preferred. The treatment may consist of a single dose of vaccine or a plurality of doses over a period of time. It is preferred that the dose be given to a human patient within the first 8 months of life. The antigen of the invention can be combined with appropriate doses of compounds including influenza antigens, such as influenza type A antigens. Also, the antigen could be a component of a recombinant vaccine which could be adaptable for oral administration.

Vaccines of the invention may be combined with other vaccines for other diseases to produce multivalent vaccines. A pharmaceutically effective amount of the antigen can be employed with a pharmaceutically acceptable carrier such as a protein or diluent useful for the vaccination of mammals, particularly humans. Other vaccines may be prepared according to methods well-known to those skilled in the art.

Those of skill will readily recognize that it is only necessary to expose a mammal to appropriate epitopes in order to elicit effective immunoprotection. The epitopes are typically segments of amino acids which are a small portion of the whole protein. Using recombinant genetics, it is routine to alter a natural protein's primary structure to create derivatives embracing epitopes that are identical to or substantially the same as (immunologically equivalent to) the naturally occurring epitopes. Such derivatives may include peptide fragments, amino acid substitutions, amino acid deletions and amino acid additions of the amino acid sequence for the viral proteins from the human herpesvirus. For example, it is known in the protein art that certain amino acid residues can be substituted with amino acids of similar size and polarity without an undue effect upon the biological activity of the protein. The human herpesvirus proteins have significant tertiary structure and the epitopes are usually conformational. Thus, modifications should generally preserve conformation to produce a protective immune response.

B. Antibody Prophylaxis

Therapeutic, intravenous, polyclonal or monoclonal antibodies can been used as a mode of passive immunotherapy of herpesviral diseases including perinatal varicella and CMV. Immune globulin from persons previously infected with the human herpesvirus and bearing a suitably high titer of antibodies against the virus can be given in combination with antiviral agents (e.g. ganciclovir), or in combination with other modes of immunotherapy that are currently being evaluated for the treatment of KS, which are targeted to modulating the immune response (i.e. treatment with copolymer-l, antiidiotypic monoclonal antibodies, T cell "vaccination"). Antibodies to human herpesvirus can be administered to the patient as described herein. Antibodies specific for an epitope expressed on cells infected with the human herpesvirus are preferred and can be obtained as described above.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

C. Monitoring therapeutic efficacy

This invention provides a method for monitoring the therapeutic efficacy of treatment for Kaposi's sarcoma, which comprises determining in a first sample from a subject with Kaposi's sarcoma the presence of the isolated DNA molecule, administering to the subject a therapeutic amount of an agent such that the agent is contacted to the cell in a sample, determining after a suitable period of time the amount of the isolated DNA molecule in the second sample from the treated subject, and comparing the amount of isolated DNA molecule determined in the first sample with the amount determined in the second sample, a difference indicating the effectiveness of the agent, thereby monitoring the therapeutic efficacy of treatment for Kaposi's sarcoma. As defined herein "amount" is viral load or copy number. Methods of determining viral load or copy number are known to those skilled in the art.

VII. Screening Assays For Pharmaceutical Agents of Interest in Alleviating the Symptoms of KS Since an agent involved in the causation or progression of KS has been identified and described here, assays directed to identifying potential pharmaceutical agents that inhibit the biological activity of the agent are possible. KS drug screening assays which determine whether or not a drug has activity against the virus described herein are contemplated in this invention. Such assays comprise incubating a compound to be evaluated for use in KS treatment with cells which express the KS associated human herpesvirus proteins or peptides and determining therefrom the effect of the compound on the activity of such agent. In vitro assays in which the virus is maintained in suitable cell culture are preferred, though in vivo animal models would also be effective.

Compounds with activity against the agent of interest or peptides from such agent can be screened in in vitro as well as in vivo assay systems. In vitro assays include infecting peripheral blood leukocytes or susceptible T cell lines such as MT-4 with the agent of interest in the presence of varying concentrations of compounds targeted against viral replication, including nucleoside analogs, chain terminators, antisense oligonucleotides and random polypeptides (Asada, H. et al. [7]; Kikuta et al. [48] both incorporated by reference herein). Infected cultures and their supernatants can be assayed for the total amount of virus including the presence of the viral genome by quantitative PCR, by dot blot assays, or by using immunologic methods. For example, a culture of susceptible cells could be infected with the human herpesvirus in the presence of various concentrations of drug, fixed on slides after a period of days, and examined for viral antigen by indirect immunofluorescence with monoclonal antibodies to viral peptides ([48], supra. Alternatively, chemically adhered MT-4 cell monolayers can be used for an infectious agent assay using indirect immunofluorescent antibody staining to search for focus reduction (Higashi, K. et al. [36], incorporated by reference herein).

As an alternative to whole cell in vitro assays, purified enzymes isolated from the human herpesvirus can be used as targets for rational drug design to determine the effect of the potential drug on enzyme activity, such as thymidine phosphotransferase or DNA polymerase. The genes for these two enzymes are provided herein. A measure of enzyme activity indicates effect on the agent itself.

Drug screens using herpes viral products are known and have been previously described in EP 0514830 (herpes proteases) and WO 94/04920 ($U_L13$ gene product)

This invention provides an assay for screening anti-KS chemotherapeutics. Infected cells can be incubated in the presence of a chemical agent that is a potential chemotherapeutic against KS (e.g. acyclo-guanosine) The level of virus in the cells is then determined after several days by IFA for antigens or Southern blotting for viral genome or Northern blotting for MRNA and compared to control cells. This assay can quickly screen large numbers of chemical compounds that may be useful against KS.

Further, this invention provides an assay system that is employed to identify drugs or other molecules capable of binding to the DNA molecule or proteins, either in the cytoplasm or in the nucleus, thereby inhibiting or potentiating transcriptional activity. Such assay would be useful in the development of drugs that would be specific against particular cellular activity, or that would potentiate such activity, in time or in level of activity.

This invention is further illustrated in the Experimental Details section which follows. This section is set forth to aid in an understanding of the invention but is not intended to, and should not be construed to, limit in any way the invention as set forth in the claims which follow thereafter.

EXPERIMENTAL DETAILS SECTION I

Experiment 1

Representational difference analysis (RDA) to identify and characterize unique DNA sequences in KS tissue To search for foreign DNA sequences belonging to an infectious agent in AIDS-KS, representational difference analysis (RDA) was employed to identify and characterize unique DNA sequences in KS tissue that are either absent or present in low copy number in non-diseased tissue obtained from the same patient [58]. This method can detect adenovirus genome added in single copy to human DNA but has not been used to identify previously uncultured infectious agents. RDA is performed by making simplified "representations" of genomes from diseased and normal tissues from the same individual through PCR amplification of short restriction fragments. The DNA representation from the diseased tissue is then ligated to a priming sequence and hybridized to an excess of unligated, normal tissue DNA representation. Only unique sequences found in the diseased tissue have priming sequences on both DNA strands and are preferentially amplified during subsequent rounds of PCR amplification. This process can be repeated using different ligated priming sequences to enrich the sample for unique DNA sequences that are only found in the tissue of interest.

Figure 1:
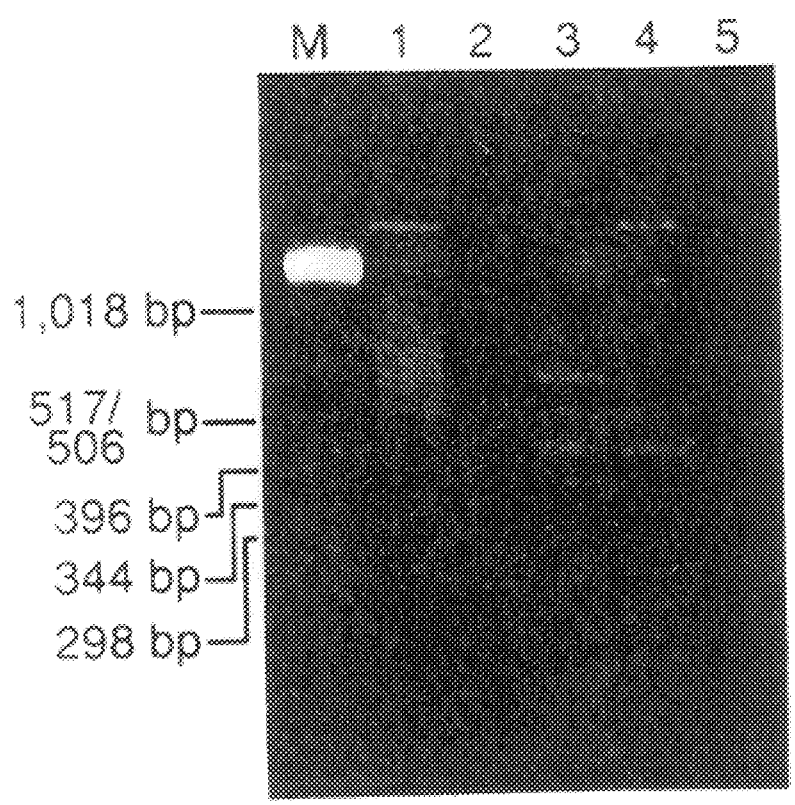
FIG. 1: Agarose gel electrophoresis of RDA products from AIDS-KS tissue and uninvolved tissue. RDA was performed on DNA extracted from KS skin tissue and uninvolved normal skin tissue obtained at autopsy from a homosexual man with AIDS-KS. Lane 1 shows the initial PCR amplified genomic representation of the AIDS-KS DNA after Bam HI digestion. Lanes 2–4 show that subsequent cycles of ligation, amplification, hybridization and digestion of the RDA products resulted in amplification of discrete bands at 380, 450, 540 and 680 bp. RDA of the extracted AIDS-KS DNA performed against itself resulted in a single band at 540 bp (lane 5). Bands at 380 bp and 680 bp correspond to KS330Bam and KS627Bam respectively after removal of 28 bp priming sequences. Bands at 450 and 540 bp hybridized nonspecifically to both KS and non-KS human DNA. Lane M is a molecular weight marker.

DNA (10 µg) extracted from both the KS lesion and unaffected tissue were separately digested to completion with Bam HI (20 units/µg) at 37° C. for 2 hours and 2 µg of digestion fragments were ligated to NBam12 and NBam24 priming sequences [primer sequences described in 58]. Thirty cycles of PCR amplification were performed to amplify "representations" of both genomes. After construction of the genomic representations, KS tester amplicons between 150 and 1500 bp were isolated from an agarose gel and NBam priming sequences were removed by digestion with Bam HI. To search for unique DNA sequences not found in non-KS driver DNA, a second set of priming sequences (JBam12 and JBam24) was ligated onto only the KS tester DNA amplicons (FIG. 1, lane 1). 0.2 µg of ligated KS lesion amplicons were hybridized to 20 µg of unligated, normal tissue representational amplicons. An aliquot of the hybridization product was then subjected to 10 cycles of PCR amplification using JBam24, followed by mung bean nuclease digestion. An aliquot of the mung bean-treated difference product was then subjected to 15 more cycles of PCR with the JBam24 primer (FIG. 1, lane 2). Amplification products were redigested with Bam HI and 200 ng of the digested product was ligated to RBam12 and RBam24 primer sets for a second round of hybridization and PCR amplification (FIG. 1, lane 3). This enrichment procedure was repeated a third time using the JBam primer set (FIG. 1, lane 4). Both the original driver and the tester DNA samples (Table 2, Patient A) were subsequently found to contain the AIDS-KS specific sequences KS330Bam and KS631Bam (previously identified as KS627Bam) indicating that RDA can be successfully employed when the target sequences are present in unequal copy number in both tissues.

The initial round of DNA amplification-hybridization from KS and normal tissue resulted in a diffuse banding pattern (FIG. 1, lane 2), but four bands at approximately 380, 450, 540 and 680 bp were identifiable after the second amplification-hybridization (FIG. 1, lane 3). These bands became discrete after a third round of amplification-hybridization (FIG. 1, lane 4). Control RDA, performed by hybridizing DNA extracted from AIDS-KS tissue against itself, produced a single band at approximately 540 bp (FIG. 1, lane 5). The four KS-associated bands (designated KS330Bam, KS390Bam, KS480Bam, KS627Bam after digestion of the two flanking 28 bp ligated priming sequences with Bam HI) were gel purified and cloned by insertion into the pCRII vector. PCR products were cloned in the pCRII vector using the TA cloning system (Invitrogen Corporation, San Diego, Calif.).

Experiment 2
Determination of the specificity of AIDS-KS unique sequences

To determine the specificity of these sequences for AIDS-KS, random-primed $^{32}$P-labeled inserts were hybridized to Southern blots of DNA extracted from cryopreserved tissues obtained from patients with and without AIDS. All AIDS-KS specimens were examined microscopically for morphologic confirmation of KS and immunohistochemically for Factor VIII, Ulex europaeus and CD34 antigen expression. One of the AIDS-KS specimens was apparently mislabeled since KS tissue was not detected on microscopic examination but was included in the KS specimen group for purposes of statistical analysis. Control tissues used for comparison to the KS lesions included 56 lymphomas from patients with and without AIDS, 19 hyperplastic lymph nodes from patients with and without AIDS, 5 vascular tumors from nonAIDS patients and 13 tissues infected with opportunistic infections that commonly occur in AIDS patients. Control DNA was also extracted from a consecutive series of 49 surgical biopsy specimens from patients without AIDS. Additional clinical and demographic information on the specimens was not collected to preserve patient confidentiality.

The tissues, listed in Table 1, were collected from diagnostic biopsies and autopsies between 1983 and 1993 and stored at −70° C. Each tissue sample was from a different patient, except as noted in Table 1. Most of the 27 KS specimens were from lymph nodes dissected under surgical conditions which diminishes possible contamination with normal skin flora. All specimens were digested with Bam HI prior to hybridization. KS390Bam and KS480Bam hybridized nonspecifically to both KS and non-KS tissues and were not further characterized. 20 of 27 (74%) AIDS-KS DNAs hybridized with variable intensity to both KS330Bam and KS627Bam, and one additional KS specimen hybridized only to KS627Bam by Southern blotting (FIG. 2 and Table 1). In contrast to AIDS-KS lesions, only 6 of 39 (15%) non-KS tissues from patients with AIDS hybridized to the KS330Bam and KS627Bam inserts (Table 1).

Specific hybridization did not occur with lymphoma or lymph node DNA from 36 persons without AIDS or with control DNA from 49 tissue biopsy specimens obtained from a consecutive series of patients. DNA extracted from several vascular tumors, including a hemangiopericytoma, two angiosarcomas and a lymphangioma, were also negative by Southern blot hybridization. DNA extracted from tissues with opportunistic infections common to AIDS patients, including 7 acid-fast bacillus (undetermined species), 1 cytomegalovirus, 1 cat-scratch bacillus, 2 cryptococcus and 1 toxoplasmosis infected tissues, were negative by Southern blot hybridization to KS330Bam and KS627Bam (Table 1).

TABLE 1

Southern blot hybridization for KS330Bam and KS627Bam and PCR amplification for KS330$_{234}$ in human tissues from individual patients.

| Tissue | n | KS330Bam Southern hybridization n (%) | KS627Bam Southern hybridization n (%) | KS330$_{234}$ PCR positive |
|---|---|---|---|---|
| AIDS-KS | 27* | 20 (74) | 21 (78) | 25 (93) |
| AIDS lymphomas | 27† | 3 (11) | 3 (11) | 3 (11) |
| AIDS lymph nodes | 12 | 3 (25) | 3 (25) | 3 (25) |
| Non-AIDS Lymphomas | 29 | 0 (0) | 0 (0) | 0 (0) |
| Non-AIDS lymph nodes | 7 | 0 (0) | 0 (0) | 0 (0) |
| Vascular tumors | 4§ | 0 (0) | 0 (0) | 0 (0) |
| Opportunistic infections | 13Π | 0 (0) | 0 (0) | 0 (0) |
| Consecutive surgical biopsies | 49¶** | 0 (0) | 0 (0) | 0 (0) |

Legend to Table 1:
*Includes one AIDS-KS specimen unamplifiable for p53 exon 6 and one tissue which on microscopic examination did not have any detectable KS tissue present. Both of these samples were negative by Southern blot hybridization to KS330Bam and KS627Bam and by PCR amplification for the K5330$_{234}$ amplicon.
†Includes 7 small non-cleaved cell lymphomas, 20 diffuse large cell and immunoblastic lymphomas. Three of the lymphomas with immunoblastic morphology were positive for KS330Bam and KS627Bam.
‡Includes 13 anaplastic large cell lymphomas, 4 diffuse large cell lymphomas, 4 small lymphocytic lymphomas/chronic lymphocytic leukemias, 3 hairy cell leukemias, 2 monocytoid B-cell lymphomas, 1 follicular small cleaved cell lymphoma, 1 Burkitt's lymphoma, 1 plasmacytoma.
§Includes 2 angiosarcomas, 1 hemangiopericytoma and 1 lymphangioma.
ΠIncludes 2 cryptococcus, 1 toxoplasmosis, 1 cat-scratch bacillus, 1 cytomegalovirus, 1 Epstein-Barr virus, and 7 acid-fast bacillus infected tissues. In addition, pure cultures of Mycobacterium avium-complex were negative by Southern hybridization and PCR, and pure cultures of Mycoplasma penetrans were negative by PCR.
¶Tissues included skin, appendix, kidney, prostate, hernia sac, lung, fibrous tissue, gallbladder, colon, foreskin, thyroid, small bowel, adenoid, vein, axillary tissue, lipoma, heart, mouth, hemorrhoid, pseudoaneurysm and fistula track. Tissues were collected from a consecutive series of biopsies on patients without AIDS but with unknown HIV serostatus.
**Apparent nonspecific hybridization at approximately 20 Kb occurred in 4 consecutive surgical biopsy DNA samples: one colon and one hernia sac DNA sample hybridized to KS330Bam alone, another hernia sac DNA sample hybridized to KS627Bam alone and one appendix DNA sample hybridized to both KS330Bam and KS627Bam. These samples did not hybridize in the 330–630 bp range expected for these sequences and were PCR negative for KS330$_{234}$.

In addition, DNA from Epstein-Barr virus-infected peripheral blood lymphocytes and pure cultures of Mycobacterium avium-complex were also negative by Southern hybridization. Overall, 20 of 27 (74%) AIDS-KS specimens hybridized to KS330Bam and 21 of 27 (78%) AIDS-KS specimens hybridized to KS627Bam, compared to only 6 of 142 (4%) non-KS human DNA control specimens ($\chi^2$=85.02, $p<10^{-7}$ and $\chi^2$=92.4, $p<10^{-7}$ respectively).

Figure 2A:
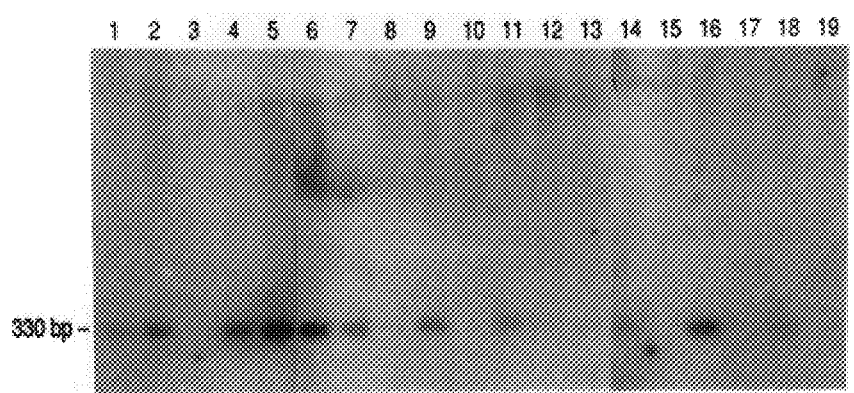
FIGS. 2A–2B: Hybridization of $^{32}$P-labelled KS330Bam (FIG. 2A) and KS627Bam (FIG. 2B) sequences to a representative panel of 19 DNA samples extracted from KS lesions and digested with Bam HI. KS330Bam hybridized to 11 of the 19 and KS627Bam hybridized to 12 of the 19 DNA samples from AIDS-KS lesions. Two additional cases (lanes 12 and 13) were shown to have faint bands with both KS330Bam and KS627Bam probes after longer exposure. One negative specimen (lane 3) did not have microscopically detectable KS in the tissue specimen. Seven of 8 additional KS DNA samples also hybridized to both sequences.
Figure 2B:
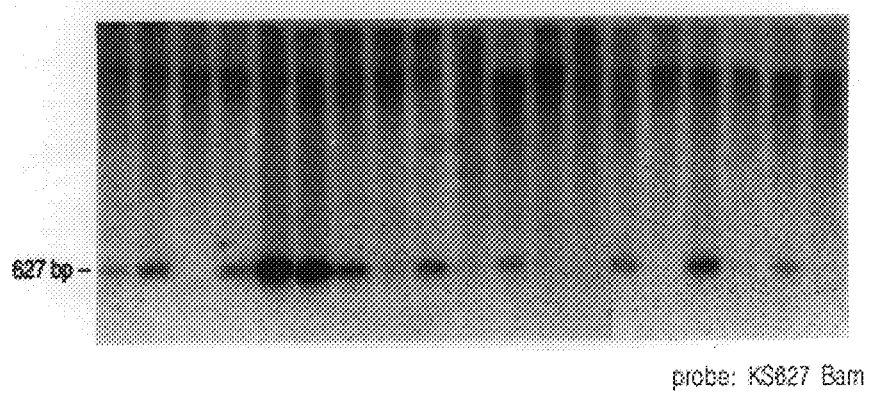

The sequence copy number in the AIDS-KS tissues was estimated by simultaneous hybridization with KS330Bam and a 440 bp probe for the constant region of the T cell receptor β gene [76]. Samples in lanes 5 and 6 of FIGS. 2A–2B showed similar intensities for the two probes indicating an average copy number of approximately two KS330Bam sequences per cell, while remaining tissues had weaker hybridization signals for the KS330Bam probe.

Experiment 3
Characterization of KS330Bam and KS627Bam

To further characterize KS330Bam and KS627Bam, six clones for each insert were sequenced. The Sequenase version 2.0 (United States Biochemical, Cleveland, Ohio) system was used and sequencing was performed according to manufacturer's instructions. Nucleotides sequences were confirmed with an Applied Biosystems 373A Sequencer in the DNA Sequencing Facilities at Columbia University.

KS330Bam is a 330 bp sequence with 51% G:C content (FIG. 3B) and KS627Bam is a 627 bp sequence with a 63% G:C content (FIG. 3C). KS330Bam has 54% nucleotide identity to the BDLF1 open reading frame (ORF) of Epstein-Barr virus (EBV). Further analysis revealed that both KS330Bam and KS627Bam code for amino acid sequences with homology to polypeptides of viral origin. SwissProt and PIR protein databases were searched for homologous ORF using BLASTX [3].

KS330Bam is 51% identical by amino acid homology to a portion of the ORF26 open reading frame encoding the capsid protein VP23 (NCBI g.i. 60348, bp 46024–46935) of herpesvirus saimiri [2], a gammaherpesvirus which causes fulminant lymphoma in New world monkeys. This fragment also has a 39% identical amino acid sequence to the theoretical protein encoded by the homologous open reading frame BDLF1 in EBV (NCBI g.i. 59140, bp 132403–133307) [9]. The amino acid sequence encoded by KS627Bam is homologous with weaker identity (31%) to the tegument protein, gp140 (ORF 29, NCBI g.i. 60396, bp 108782–112681) of herpesvirus saimiri.

Sequence data from KS330Bam was used to construct PCR primers to amplify a 234 bp fragment designated KS330$_{234}$ (FIG. 3B). The conditions for PCR analyses were as follows: 94° C. for 2 min (1 cycle); 94° C. for 1 min, 58° C. for 1 min, 72° C. for 1 min (35 cycles); 72° C. extension for 5 min (1 cycle). Each PCR reaction used 0.1 μg of genomic DNA, 50 pmoles of each primer, 1 unit of Taq polymerase, 100 μM of each deoxynucleotide triphosphate, 50 mM KCl, 10 mM Tris-HCl (pH 9.0), and 0.1% Triton-X-100 in a final volume of 25 μl. Amplifications were carried out in a Perkin-Elmer 480 Thermocycler with 1-s ramp times between steps.

Figures 4A, 4B:
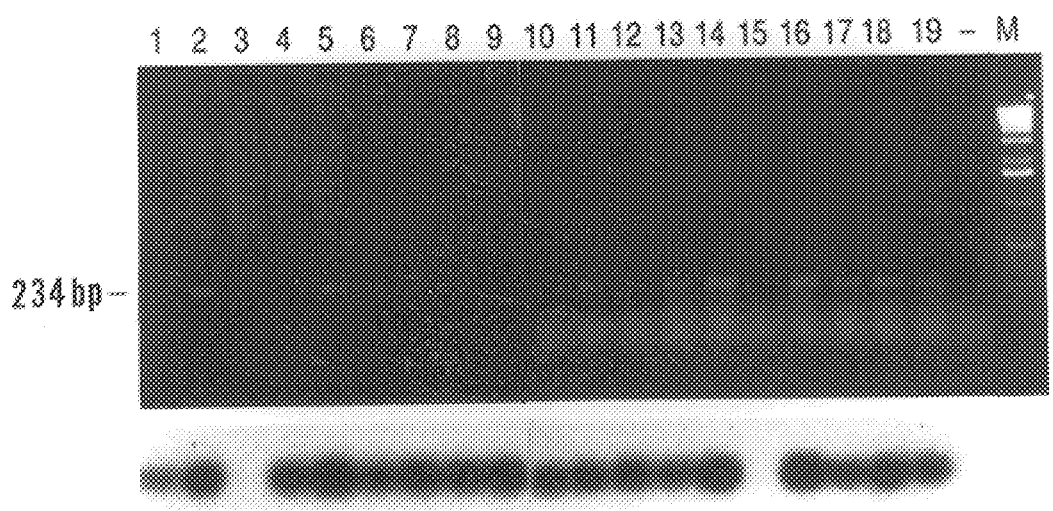
FIGS. 4A–4B: PCR amplification of a representative set of KS-derived DNA samples using KS330$_{234}$ primers.
Figure 7:
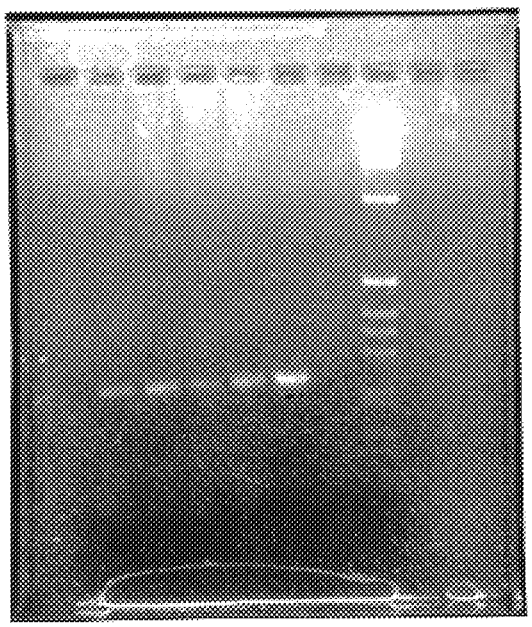
FIG. 7: Subculture of Raji cells co-cultivated with BCBL-1 cells treated with TPA for 2 days. PCR shows that Raji cells are positive for KSHV sequences and indicate that the agent is a transmissible virus.
Figure 8:
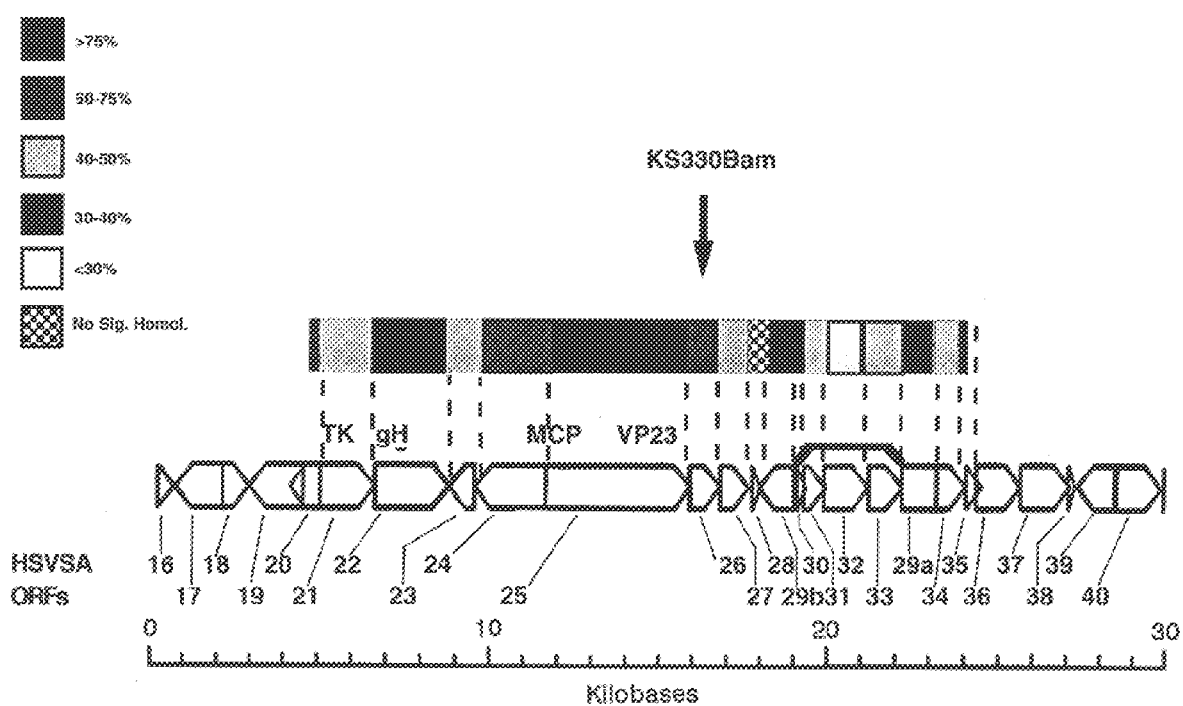
FIG. 8: A schematic diagram of the orientation of KSHV open reading frames identified on the KS5 20,710 bp DNA fragment. Homologs to each open reading frame from a corresponding region of the herpesvirus saimiri (HSVSA) genome are present in an identical orientation, except for the region corresponding to the ORF 28 of HSVSA (middle schematic section). The shading for each open reading frame corresponds to the approximate % amino acid identity for the KSHV ORF compared to this homolog in HSVSA. Noteworthy homologs that are present in this section of DNA include homologs to thymidine kinase (ORF21), gH glycoprotein (ORF22), major capsid protein (ORF25) and the VP23 protein (ORF26) which contains the original KS330Bam sequence derived by representational difference analysis.

Although Southern blot hybridization detected the KS330Bam sequence in only 20 of 27 KS tissues, 25 of the 27 tissues were positive by PCR amplification for KS330$_{234}$ (FIGS. 4A–4B) demonstrating that KS330Bam is present in some KS lesions at levels below the threshold for detection by Southern blot hybridization. All KS330$_{234}$ PCR products hybridized to a $^{32}$P end-labelled 25 bp internal oligomer, confirming the specificity of the PCR (FIG. 4B). Of the two AIDS-KS specimens negative for KS330$_{234}$, both specimens appeared to be negative for technical reasons: one had no microscopically detectable KS tissue in the frozen sample (FIGS. 4A–4B, lane 3), and the other (FIGS. 4A–4B, lane 15) was negative in the control PCR amplification for the p53 gene indicating either DNA degradation or the presence of PCR inhibitors in the sample. PCR amplification of the p53 tumor suppressor gene was used as a control for DNA quality. Sequences of p53 primers from P6-5, 5'-ACAGGGCTGGTTGCCCAGGGT-3' (SEQ ID No: 44); and P6-3. 5'-AGTTGCAAACCAGACCTCAG-3' (SEQ ID NO: 45) [25].

Except for the 6 control samples from AIDS patients that were also positive by Southern blot hybridization, none of the other 136 control specimens were positive by PCR for KS330$_{234}$. All of these specimens were amplifiable for the p53 gene, indicating that inadequate PCR amplification was not the reason for lack of detection of KS330$_{234}$ in the control tissues. Samples containing DNA from two candidate KS agents, EBV and Mycoplasma penetrans (ATCC Accession No. 55252), a pathogen commonly found in the genital tract of patients with AIDS-KS [59] were also negative for amplification of KS330$_{234}$. In addition, several KS specimens were tested using commercial PCR primers (Stratagene, La Jolla, Calif.) specific for mycoplasmata and primers specific for the EBNA-2, EBNA-3C and EBER regions of EBV and were negative [57].

Overall, DNA from 25 (93%) of 27 AIDS-KS tissues were positive by PCR compared with DNA from 6 (4%) of 142 control tissues, including 6 (15%) of 39 non-KS lymph nodes and lymphomas from AIDS patients ($\chi^2$=38.2, $p<10^{-6}$), 0 of 36 lymph nodes and lymphomas from nonAIDS patients ($\chi^2$=55.2, $p<10^{-7}$) and 0 of 49 consecutive biopsy specimens ($\chi^2$=67.7, $p<10^{-7}$). Thus, KS330$_{234}$ was found in all 25 amplifiable tissues with microscopically detectable AIDS-KS, but rarely occurred in non-KS tissues, including tissues from AIDS patients.

Of the six control tissues from AIDS patients that were positive by both PCR and Southern hybridization, two patients had KS elsewhere, two did not develop KS and complete clinical histories for the remaining two patients were unobtainable. Three of the six positive non-KS tissues were lymph nodes with follicular hyperplasia taken from patients with AIDS. Given the high prevalence of KS among patients with AIDS, it is possible that undetected microscopic foci of KS were present in these lymph nodes. The other three positive tissue specimens were B cell immunoblastic lymphomas from AIDS patients. It is possible that the putative KS agent is also a cofactor for a subset of AIDS-associated lymphomas [16, 17, 80].

To determine whether KS330Bam and KS627Bam are portions of a larger genome and to determine the proximity of the two sequences to each other, samples of KS DNA were digested with Pvu II restriction enzymes. Digested genomic DNA from three AIDS-KS samples were hybridized to KS330Bam and KS627Bam by Southern blotting (FIG. 5). These sequences hybridized to various sized fragments of the digested KS DNA indicating that both sequences are fragments of larger genomes. Differences in the KS330Bam hybridization pattern to Pvu II digests of the three AIDS-KS specimens indicate that polymorphisms may occur in the larger genome. Individual fragments from the digests failed to simultaneously hybridize with both KS330Bam and KS627Bam, demonstrating that these two Bam HI restriction fragments are not adjacent to one another.

If KS330Bam and KS627Bam are heritable polymorphic DNA markers for KS, these sequences should be uniformly detected at non-KS tissue sites in patients with AIDS-KS. Alternatively, if KS330Bam and KS627Bam are sequences specific for an exogenous infectious agent, it is likely that some tissues are uninfected and lack detectable KS330Bam and KS627Bam sequences. DNA extracted from multiple uninvolved tissues from three patients with AIDS-KS were hybridized to $^{32}$P-labelled KS330Bam and KS627Bam probes as well as analyzed by PCR using the KS330$_{234}$ primers (Table 2). While KS lesion DNA samples were positive for both bands, unaffected tissues were frequently negative for these sequences. KS lesions from patients A, B and C, and uninvolved skin and muscle from patient A were positive for KS330Bam and KS627Bam, but muscle and brain tissue from patient B and muscle, brain, colon, heart and hilar lymph node tissues from patient C were negative for these sequences. Uninvolved stomach lining adjacent to the KS lesion in patient C was positive by PCR, but negative by Southern blotting which suggests the presence of the sequences in this tissue at levels below the detection threshold for Southern blotting.

TABLE 2

Differential detection of KS330Bam, KS627Bam and KS330$_{234}$ sequences in KS-involved and non-involved tissues from three patients with AIDS-KS.

|  | KS330Bam | KS627Bam | KS330$_{234}$ |
|---|---|---|---|
| Patient A |  |  |  |
| KS, skin | + | + | + |
| nl skin | + | + | + |
| nl muscle | + | + | + |
| Patient B |  |  |  |
| KS, skin | + | + | + |
| nl muscle | − | − | − |
| nl brain | − | − | − |
| Patient C |  |  |  |
| KS, stomach | + | + | + |
| nl stomach adjacent to KS | − | − | + |
| nl muscle | − | − | − |
| nl brain | − | − | − |
| nl colon | − | − | − |
| nl heart | − | − | − |
| nl hilar lymph nodes | − | − | − |

Experiment 4
Subcloning and sequencing of KSHV

KS330Bam and KS627Bam are genomic fragments of a novel infectious agent associated with AIDS-KS. A genomic library from a KS lesion was made and a phage clone with a 20 kb insert containing the KS330Bam sequence was identified. The 20 kb clone digested with PvuII (which cuts in the middle of the KS330Bam sequence) produced 1.1 kb and 3 kb fragments that hybridized to KS330Bam. The 1.1 kb subcloned insert and ~900 bp from the 3 kb subcloned insert resulting in 9404 bp of contiguous sequence was entirely sequenced. This sequence contains partial and complete open reading frames homologous to regions in gamma herpesviruses.

The KS330Bam sequence is an internal portion of an 918 bp ORF with 55–56% nucleotide identity to the ORF26 and BDLF1 genes of HSVSA and EBV respectively. The EBV and HSVSA translated amino acid sequences for these ORFs demonstrate extensive homology with the amino acid sequence encoded by the KS-associated 918 bp ORF (FIG. 6). In HSVSA, the VP23 protein is a late structural protein involved in capsid construction. Reverse transcriptase (RT)-PCR of mRNA from a KS lesion is positive for transcribed KS330Bam mRNA and that indicates that this ORF is transcribed in KS lesions. Additional evidence for homology between the KS agent and herpesviruses comes from a comparison of the genomic organization of other potential ORFs on the 9404 bp sequence (FIG. 3A) The 5' terminus of the sequence is composed nucleotides having 66–67% nucleotide identity and 68–71% amino acid identity to corresponding regions of the major capsid protein (MCP) ORFs for both EBV and HSVSA. This putative MCP ORF of the KS agent lies immediately 5' to the BDLF1/ORF26 homolog which is a conserved orientation among herpesvirus subfamilies for these two genes. At the 3' end of this sequence, the reading frame has strong amino acid and nucleotide homology to HSVSA ORF 27. Thus, KS-associated DNA sequences at four loci in two separate regions with homologies to gamma herpesviral genomes have been identified.

Figure 9:
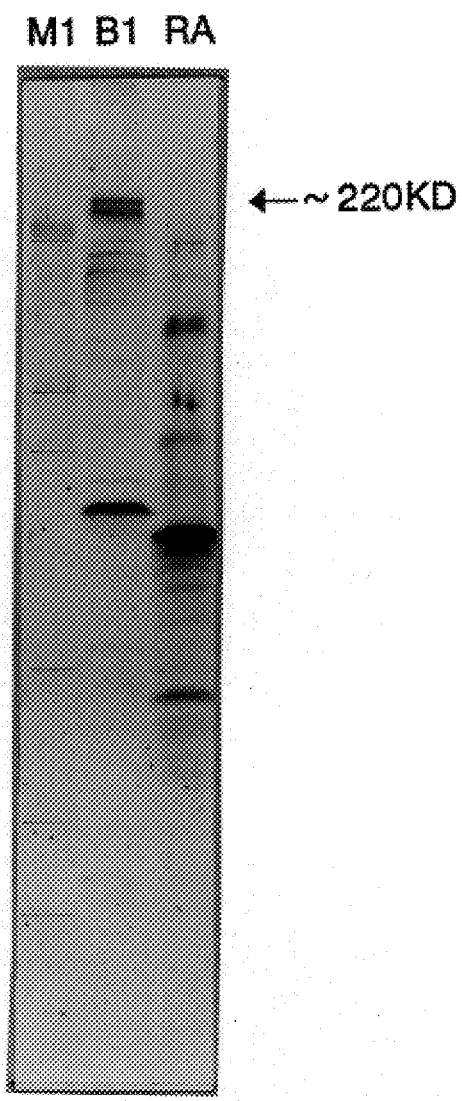
FIG. 9: The ~200 kD antigen band appearing on a Western blot of KS patient sera against BCBL1 lysate (B1) and Raji lysate (RA). M is molecular weight marker. The antigen is a doublet between ca. 210 kD and 240 kD.
Figure 10:
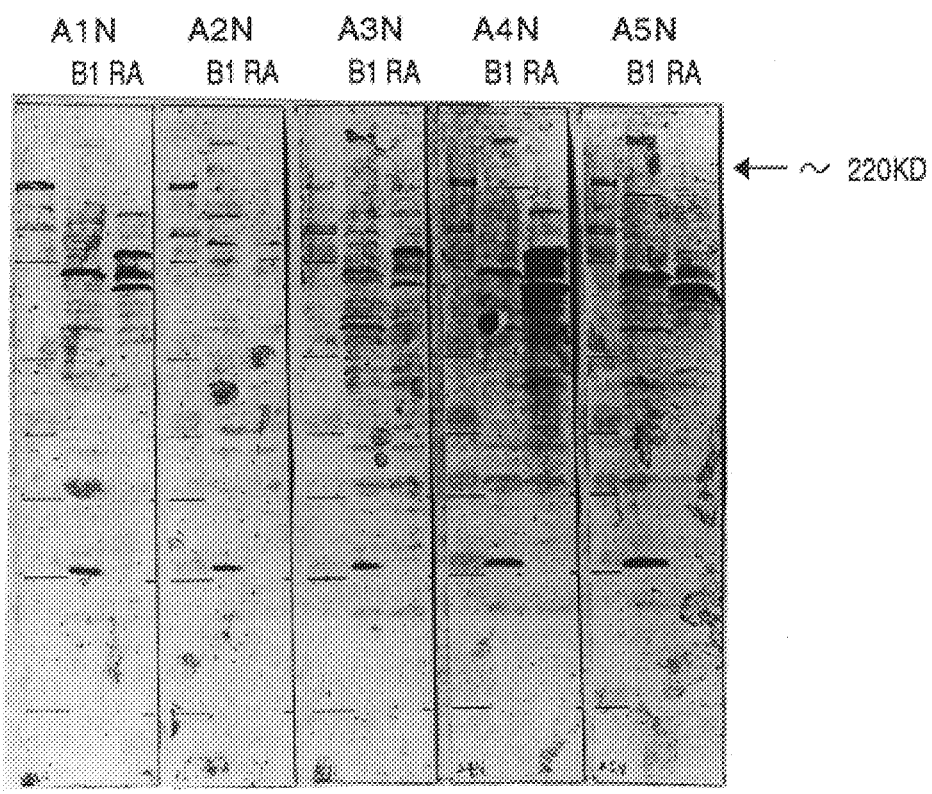
FIG. 10: 5 control patient sera without KS (A1N, A2N, A3N, A4N and A5N). B1=BCBL1 lysate, RA=Raji lysate.

In addition to fragments obtained from Pvu II digest of the 21 Kb phage insert described above, fragments obtained from a BamHI/NotI digest were also subcloned into pBluescript (Stratagene, La Jolla, Calif.). The termini of these subcloned fragments were sequenced and were also found to be homologous to nucleic acid sequence EBV and HSVSA genes. These homologs have been used to develop a preliminary map of subcloned fragments (FIG. 9). Thus, sequencing has revealed that the KS agent maintains co-linear homology to gamma herpesviruses over the length of the 21 Kb phage insert.

Experiment 5
Determination of the phylogeny of KSHV

Regions flanking KS330Bam were sequenced and characterized by directional walking. This was performed by the following strategy: 1) KS genomic libraries were made and screened using the KS330Bam fragment as a hybridization probe, 2) DNA inserts from phage clones positive for the KS330Bam probe were isolated and digested with suitable restriction enzyme(s), 3) the digested fragments were subcloned into pBluescript (Stratagene, La Jolla, Calif.), and 4) the subclones were sequenced. Using this strategy, the major capsid protein (MCP) ORF homolog was the first important gene locus identified. Using sequenced unique 3' and 5' end-fragments from positive phage clones as probes, and following the strategy above a KS genomic library are screened by standard methods for additional contiguous sequences.

For sequencing purposes, restriction fragments are subcloned into phagemid pBluescript KS+, pBluescript KS−, pBS+, or pBS− (Stratagene) or into plasmid pUC18 or pUC19. Recombinant DNA was purified through CsCl density gradients or by anion-exchange chromatography (Qiagen).

Nucleotide sequenced by standard screening methods of cloned fragments of KSHV were done by direct sequencing of double- stranded DNA using oligonucleotide primers synthesized commercially to "walk" along the fragments by the dideoxy-nucleotide chain termination method. Junctions between clones are confirmed by sequencing overlapping clones.

Targeted homologous genes in regions flanking KS330Bam include, but are not limited to: Il-10 homolog, thymidine kinase (TK), g85, g35, gH, capsid proteins and MCP. TK is an early protein of the herpesviruses functionally linked to DNA replication and a target enzyme for anti-herpesviral nucleosides. TK phosphorylates acyclic nucleosides such as acyclovir which in turn inhibit viral DNA polymerase chain extension. Determining the sequence of this gene will aid in the prediction of chemotherapeutic agents useful against KSHV. TK is encoded by the EBV BXLF1 ORF located ~9700 bp rightward of BDLF1 and by the HSVSA ORF 21 ~9200 bp rightward of the ORF 26. A subcloned fragment of KS5 was identified with strong homology to the EBV and HSVSA TK open reading frames.

g85 is a late glycoprotein involved in membrane fusion homologous to gH in HSV1. In EBV, this protein is encoded by BLXF2 ORF located ~7600 bp rightward of BDLF1, and in HSVSA it is encoded by ORF 22 located ~7100 bp rightward of ORF26.

g35 is a late EBV glycoprotein found in virion and plasma membrane. It is encoded by BDLF3 ORF which is 1300 bp leftward of BDLF1 in EBV. There is no BDLF3 homolog in HSVSA. A subcloned fragment has already been identified with strong homology to the EBV gp35 open reading frame.

Major capsid protein (MCP) is a conserved 150 KDa protein which is the major component of herpesvirus capsid. Antibodies are generated against the MCP during natural infection with most herpesviruses. The terminal 1026 bp of this major capsid gene homolog in KSHV have been sequenced.

Targeted homologous genes/loci in regions flanking KS627Bam include, but are not limited to: terminal reiterated repeats, LMPI, EBERs and Ori P. Terminal reiterated sequences are present in all herpesviruses. In EBV, tandomly reiterated 0.5 Kb long terminal repeats flank the ends of the linear genome and become joined in the circular form. The terminal repeat region is immediately adjacent to BNRF1 in EBV and ORF 75 in HSVSA. Since the number of terminal repeats varies between viral strains, identification of terminal repeat regions may allow typing and clonality studies of KSHV in KS legions. Sequencing through the terminal repeat region may determine whether this virus is integrated into human genome in KS.

LMPI is an latent protein important in the transforming effects of EBV in Burkitt's lymphoma. This gene is encoded by the EBV BNRF1 ORF located ~2000 bp rightward of tegument protein ORF BNRF1 in the circularized genome. There is no LMP1 homolog in HSVSA.

EBERs are the most abundant RNA in latently EBV infected cells and Ori-P is the origin of replication for latent EBV genome. This region is located between ~4000–9000 bp leftward of the BNRF1 ORF in EBV; there are no corresponding regions in HSVSA.

The data indicates that the KS agent is a new human herpesvirus related to gamma herpesviruses EBV and HSVSA. The results are not due to contamination or to incidental co-infection with a known herpesvirus since the sequences are distinct from all sequenced herpesviral genomes (including EBV, CMV, HHV6 and HSVSA) and are associated specifically with KS in three separate comparative studies. Furthermore, PCR testing of KS DNA with primers specific for EBV-1 and EBV-2 failed to demonstrate these viral genomes in these tissues. Although KSHV is homologous to EBV regions, the sequence does not match any other known sequence and thus provides evidence for a new viral genome, related to but distinct from known members of the herpesvirus family.

Experiment 6
Serological studies
Indirect immunofluorescence assay (IFA)

Virus-containing cells are coated to a microscope slide. The slides are treated with organic fixatives, dried and then incubated with patient sera. Antibodies in the sera bind to the cells, and then excess nonspecific antibodies are washed off. An antihuman immunoglobulin linked to a fluorochrome, such as fluorescein, is then incubated with the slides, and then excess fluorescent immunoglobulin is washed off. The slides are then examined under a microscope and if the cells fluoresce, then this indicates that the sera contains antibodies directed against the antigens present in the cells, such as the virus.

An indirect immunofluorescence assay (IFA) was performed on the Body Cavity-Based Lymphoma cell line (BCBL-1), which is a naturally transformed EBV infected (nonproducing) B cell line, using 4 KS patient sera and 4 control sera (from AIDS patients without KS). Initially, both sets of sera showed similar levels of antibody binding. To remove nonspecific antibodies directed against EBV and lymphocyte antigens, sera at 1:25 dilution were pre-adsorbed using $3 \times 10^6$ 1% paraformaldehyde-fixed Raji cells per ml of sera. BCBL1 cells were fixed with ethanol/acetone, incubated with dilutions of patient sera, washed and incubated with fluorescein-conjugated goat anti-human IgG. Indirect immunofluorescent staining was determined.

Table 3 shows that unabsorbed case and control sera have similar end-point dilution indirect immunofluorescence assay (IFA) titers against the BCBL1 cell line. After Raji adsorption, case sera have four-fold higher IFA titers against BCBL1 cells than control sera. Results indicated that pre-adsorption against paraformaldehyde-fixed Raji cells reduces fluorescent antibody binding in control sera but do not eliminate antibody binding to KS case sera. These results indicate that subjects with KS have specific antibodies directed against the KS agent that can be detected in serological assays such as IFA, Western blot and Enzyme immunoassays (Table 3).

TABLE 3

Indirect immunofluorescence end-point titers for KS case and non-KS control sera against the BCBL-1 cell line

| Sera No. | Status* | Pre-adsorption | Post-adsorption** |
|---|---|---|---|
| 1 | KS | ≧1:400 | ≧1:400 |
| 2 | KS | 1:100 | 1:100 |
| 3 | KS | 1:200 | 1:100 |
| 4 | KS | ≧1:400 | 1:200 |
| 5 | Control | ≧1:400 | 1:50 |
| 6 | Control | 1:50 | 1:50 |
| 7 | Control | 1:100 | 1:50 |
| 8 | Control | 1:200 | 1:50 |

Legend Table 3:
*KS = autopsy-confirmed male, AIDS patient
Control = autopsy-confirmed female, AIDS patient, no KS
**Adsorbed against RAJI cells treated with 1% paraformaldehyde Immunoblotting ("Western blot")

Virus-containing cells or purified virus (or a portion of the virus, such as a fusion protein) is electrophoresed on a polyacrylamide gel to separate the protein antigens by molecular weight. The proteins are blotted onto a nitrocellulose or nylon membrane, then the membrane is incubated in patient sera. Antibodies directed against specific antigens are developed by incubating with a anti-human immunoglobulin attached to a reporter enzyme, such as a peroxidase. After developing the membrane, each antigen reacting against antibodies in patient sera shows up as a band on the membrane at the corresponding molecular weight region.

Enzyme immunoassay ("EIA or ELISA")

Virus-containing cells or purified virus (or a portion of the virus, such as a fusion protein) is coated to the bottom of a 96-well plate by various means (generally incubating in alkaline carbonate buffer). The plates are washed, then the wells are incubated with patient sera. Antibodies in the sera directed against specific antigens stick on the plate. The wells are washed again to remove nonspecific antibody, then they are incubated with a antihuman immunoglobulin attached to a reporter enzyme, such as a peroxidase. The plate is washed again to remove nonspecific antibody and then developed. Wells containing antigen that is specifically recognized by antibodies in the patients sera change color and can be detected by an ELISA plate reader (a spectrophotomer).

All three of these methods can be made more specific by pre-incubating patient sera with uninfected cells to adsorb out cross-reacting antibodies against the cells or against other viruses that may be present in the cell line, such as EBV. Cross-reacting antibodies can potentially give a falsely positive test result (i.e. the patient is actually not infected with the virus but has a positive test result because of cross-reacting antibodies directed against cell antigens in the preparation). The importance of the infection experiments with Raji is that if Raji cells, or another well-defined cell line, can be infected, then the patient's sera can be pre-adsorbed against the uninfected parental cell line and then tested in one of the assays. The only antibodies left in the sera after pre-adsorption that bind to antigens in the preparation should be directed against the virus.

Experiment 7

BCBL 1, from lymphomatous tissues belonging to a rare infiltrating, anaplastic body cavity lymphoma occurring in AIDS patients has been placed in continuous cell culture and shown to be continuously infected with the KS agent. This cell line is also naturally infected with Epstein-Barr Virus (EBV). The BCBL cell line was used as an antigen substrate to detect specific KS antibodies in persons infected with the putative virus by Western-blotting. Three lymphoid B cell lines were used as controls. These included the EBV genome positive cell line P3H3, the EBV genome defective cell line Raji and the EBV genome negative cell line Bjab.

Cells from late-log phase culture were washed 3 time with PBS by centrifugation at 500 g for 10 min. and suspended in sample buffer containing 50 mM Tris-HCl pH 6.8, 2% SDS (w/v), 15% glycerol (v/v), 5% β-mercaptoethanol (v/v) and 0.001% bromophenol (w/v) with protease inhibitor, 100 $\mu$M phenylmethylsulfonyl fluoride (PMSF). The sample was boiled at 100° C. for 5 min and centrifuged at 14,000 g for 10 min. The proteins in the supernatant was then fractionated by sodium, dodecyl sulfate-polyacrylamide gel electrophoresis (SDS-PAGE) under reducing conditions with a separation gel of 15% and a stacking gel of 5% (3). Prestained protein standards were included: myosin, 200 kDa; β-galactosidase, 118 kDA; BSA, 78 kDa; ovalbumin, 47.1 kDa; carbonic anhydrase, 31.4 kDa; soybean trypsin inhibitor, 25.5 kDa, lysozyme, 18.8 kDa and aprotinin, 8.3 kDa (Bio-Rad). Immunoblotting experiments were performed according to the method of Towbin et al. (4). Briefly, the proteins were electrophorectically transferred to Hybon-C extra membranes (Pharmacia) at 24 V for 70 min. The membranes were then dried at 37° C. for 30 min, saturated with 5% skim milk in Tris-buffered saline, pH 7.4 (TES) containing 50 mM Tris-HCl and 200 mM NaCl, at room temperature for 1 h. The membranes were subsequently incubated with human sera at dilution 1:200 in 1% skim milk overnight at room temperature, washed 3 times with a solution containing TBS, 0.2% Triton X-100 and 0.05% skim milk and then 2 times with TBS. The membranes were then incubated for 2 h at room temperature with alkaline phosphatase conjugated goat anti-mouse IgG+IgM +IgA (Sigma) diluted at 1:5000 in 1% skim milk. After repeating the washing,the membranes were stained with nitroblue tetranolium chloride and 5-bromo-4-chloro-3-indolylphosphate p-toluidine salt (Gibco BRL).

Two bands of approximately 226 kDa and 234 kDa were identified to be specifically present on the Wester-blot of BCBL cell lysate in 5 sera from AIDS gay man patients infected with KS. These 2 bands were absent from the lysates of P3H3, Raji and Bjab cell lysates. 5 sera from AIDS gay man patients without KS and 2 sera from AIDS woman patients without KS as well as 1 sera from nasopharyncel carcinoma patient were not able to detect these 2 bands in BCBL 1, P3H3, Raji and Bjab cell lysates. In a blinded experiment, using the 226 kDa and 234 kDa markers, 15 out of 16 sera from KS patients were correctly identified. In total, the 226 kDa and 234 kDa markers were detected in 20 out of 21 sera from KS patients.

The antigen is enriched in the nuclei fraction of BCBL1. Enriched antigen with low background can be obtained by preparing nucleic from BCBC as the starting antigen preparation using standard, widely available protocols. For example, 500–750ml of BCBL at $5\times10^5$ cells/ml can be pelleted at low speed. The pellet is placed in 10 mM NaCl, 10 mM Tris pH 7.8, 1.5 mM $MgCl_2$ (equi volume) +1.0% NP-40 on ice for 20 min to lyse cells. The lysate is then spun at 1500 rpm for 10 min. to pellet nucleic. The pellet is used as the starting fraction for the antigen preparation for the Western blot. This will reduce cross- reactive cytoplasmic antigens.

Experiment 8
Transmission studies
Co-infection experiments

BCBL1 cells were co-cultivated with Raji cell lines separated by a 0.45$\mu$ tissue filter insert. Approximately, 1–2$\times10^6$ BCBL1 and 2$\times10^6$ Raji cells were co-cultivated for 2–20 days in supplemented RPMI alone, in 10 $\mu$g/ml 5'-bromodeoxyuridine (BUdR) and 0.6 $\mu$g/ml 5'-flourodeoxyuridine or 20 ng/ml 12-O-tetradecanoylphorbol-13-acetate (TPA). After 2,8,12 or 20 days co-cultivation, Raji cells were removed, washed and placed in supplemented RPMI 1640 media. A Raji culture co-cultivated with BCBL1 in 20 ng/ml TPA for 2 days survived and has been kept in continuous suspension culture for >10 weeks. This cell line, designated RCC1 (Raji Co-Culture, No. 1) remains PCR positive for the $KS330_{234}$ sequence after multiple passages. This cell line is identical to its parental Raji cell line by flow cytometry using EMA, B1, B4 and BerH2 lymphocyte-flow cytometry (approximately 2%). RCC1 periodically undergo rapid cytolysis suggestive of lytic reproduction of the agent. Thus, RCC1 is a Raji cell line newly infected with KSHV.

The results indicate the presence of a new human virus, specifically a herpesvirus in KS lesions. The high degree of association between this agent and AIDS-KS (>90w), and the low prevalence of the agent in non-KS tissues from immunocompromised AIDS patients, indicates that this agent has a causal role in AIDS-KS [47, 68].

Experiment 10
Isolation of KSHV

Crude virus preparations are made from either the supernatant or low speed pelleted cell fraction of BCBL1 cultures. Approximately 650 ml or more of log phase cells should be used (>5$\times10^6$ cells/ml).

For bonding whole virion from supernatant, the cell free supernatant is spun at 10,000 rpm in a GSA rotor for 10 min to remove debris. PEG-8000 is added to 7%, dissolved and placed on ice for >2.5 hours. The PEG-supernatant is then spun at 10,000$\times$g for 30 min. supernatant is poured off and the pellet is dried and scraped together from the centrifuge bottles. The pellet is then resuspended in a small volume (1–2 ml) of virus buffer (VB, 0.1M NaCl, 0.01M Tris, pH 7.5). This procedure will precipitate both naked genome and whole virion. The virion are then isolated by centrifugation at 25,000 rpm in a 10–50% sucrose gradient made with VB. One ml fractions of the gradient are then obtained by standard techniques (e.g. using a fractionator) and each fraction is then tested by dot blotting using specific hybridizing primer sequences to determine the gradient fraction containing the purified virus (preparation of the fraction maybe needed in order to detect the presence of the virus, such as standard DNA extraction).

To obtain the episomal DNA from the virus, the pellet of cells is washed and pelleted in PBS, then lysed using hypotonic shock and/or repeated cycles of freezing and thawing in a small volume (<3 ml). Nuclei and other cytoplasmic debris are removed by centrifugation at 10,000 g for 10 min, filtration through a 0.45m filter and then repeat centrifugation at 10,000 g for 10 min. This crude preparation contains viral genome and soluble cell components. The genome preparation can then be gently chloroformphenol extracted to remove associated proteins or can be placed in neutral DNA buffer (1M NaCl, 50 mM Tris, 10 mM EDTA, pH 7.2–7.6) with 2% sodium dodecylsulfate (SDS) and 1% sarcosyl. The genome is then banded by centrifugation through 10–30% sucrose gradient in neutral DNA buffer containing 0.15% sarcosyl at 20,000 rpm in a SW 27.1 rotor for 12 hours (for 40,000 rpm for 2–3 hours in an SW41 rotor). The band is detected as described above.

An example of the method for isolating KSHV genome from KSHV infected cell cultures (97 and 98). Approximately 800 ml of BCBL1 cells are pelleted, washed with saline, and pelleted by low speed centrifugation. The cell pellet is lysed with an equal volume of RSB (10 mM NaCl, 10 mM Tris-HCl, 1.5 mM MgCl2, pH 7.8) with 1% NP-40 on ice for 10 minutes. The lysate is centrifuged at 900×g for 10 minutes to pellet nuclei. This step is repeated. To the supernatant is added 0.4% sodium dodecylsulfate and EDTA to a final concentration of 10 mM. The supernatant is loaded on a 10–30% sucrose gradient in 1.0M NaCl, 1mM EDTA, 50 mM Tris-HCl, pH 7.5. The gradients are centrifuged at 20,000 rpm on a SW 27.1 rotor for 12 hours. In FIG. 11, 0.5 ml aliquots of the gradient have been fractionated (fractions 1–62) with the 30% gradient fraction being at fraction No. 1 and the 10% gradient fraction being at fraction No. 62. Each fraction has been dot hybridized to a nitrocellulose membrane and then a $^{32}$P-labeled KSHV DNA fragment, KS631Bam has been hybridized to the membrane using standard techniques. FIG. 11 shows that the major solubilized fraction of the KSHV genome bands (i.e. is isolated) in fractions 42 through 48 of the gradient with a high concentration of the genome being present in fraction 44. A second band of solubilized KSHV DNA occurs in fractions 26 through 32.

Experiment 11
Purification of KSHV

DNA is extracted using standard techniques from the RCC-1 or RCC-1$_{2F5}$ cell line [27, 49, 66]. The DNA is tested for the presence of the KSHV by Southern blotting and PCR using the specific probes as described hereinafter. Fresh lymphoma tissue containing viable infected cells is simultaneously filtered to form a single cell suspension by standard techniques [49, 66]. The cells are separated by standard Ficoll-Plaque centrifugation and lymphocyte layer is removed. The lymphocytes are then placed at >1×10$^6$ cells/ml into standard lymphocyte tissue culture medium, such as RMP 1640 supplemented with 10% fetal calf serum. Immortalized lymphocytes containing the KSHV virus are indefinitely grown in the culture media while nonimmortolized cells die during course of prolonged cultivation.

Further, the virus may be propagated in a new cell line by removing media supernatant containing the virus from a continuously infected cell line at a concentration of >1×10$^6$ cells/ml. The media is centrifuged at 2000×g for 10 minutes and filtered through a 0.45$\mu$ filter to remove cells. The media is applied in a 1:1 volume with cells growing at >1×10$^6$ cells/ml for 48 hours. The cells are washed and pelleted and placed in fresh culture medium, and tested after 14 days of growth.

The herpesvirus may be isolated from the cell DNA in the following manner. An infected cell line, which can be lysed using standard methods such as hyposmotic shocking and Dounce homogenization, is first pelleted at 2000×g for 10 minutes, the supernatant is removed and centrifuged again at 10,000×g for 15 minutes to remove nuclei and organelles. The supernatant is filtered through a 0.45$\mu$ filter and centrifuged again at 100,000×g for 1 hour to pellet the virus. The virus can then be washed and centrifuged again at 100,000×g for 1 hour.

REFERENCES

1. Ablashi, D. V., et al. *Virology* 184:545–552.
2. Albrecht, J. C., et al. (1992) *J. Virol.* 66:5047.
3. Altshul, S. F., et al. (1990) *J. Molec. Biol.* 215:403.
4. *Analytical Biochemistry* (1984) 238:267–284.
5. Andrei, et al. (1992) *Eur. J. Clin. Microbiol. Infect. Dis.* 11(2):143–51.
6. Archibald, C. P., et al. (1992) *Epidemiol.* 3:203.
7. Asada, H., et al (1989) *J. Clin. Microbiol.* 27(10) :2204.
8. Ausubel, F., et al. (1987) *Current Protocols in Molecular Biolocy*, New York.
9. Baer, R. J., et al. (1984) *Nature* 310:207.
10. Bagasra, et al. (1992) *J. New England Journal of Medicine* 326(21):1385–1391.
11. Balzarini, et al. (1990) *Mol. Pharm.* 37,402–7.
12. *Basic and Clinical Immunology 7th Edition* D. Stites and A. Terr ed.
13. Beral, V., et al. (1990) *Lancet* 335:123.
14. Beral, V., et al. (1991) *Brit. Med. J.* 302:624.
15. Beral, V., et al. (1992) *Lancet* 339:632.
16. Bendsbe, N., et al. (1990) *Eur. J. Cancer* 26:699.
17. Biggar, R. J., et al. (1994) *Am. J. Epidemiol.* 139:362.
18. Bovenzi, P., et al. (1993) *Lancet* 341:1288.
19. Beaucage and Carruthers (1981) *Tetrahedron Lett.* 22:1859–1862.
20. Braitman, et al. (1991) *Antimicrob. Agents and Chemotherapy* 35(7):1464–8.
21. Burns and Sanford, (1990) *J. Infect. Dis.* 162(3):634–7.
22. De Clercq, (1993) *Antimicrobial Chemotherapy* 32, Suppl. A, 121–132.
23. Drew, W. L., et al. (1982) *Lancet* ii:125.
24. Falk, et al. (1991) *Nature* 351:290.
25. Gaidano, G., et al. (1991) *Proc. Natl. Acad. Sci. USA* 88:5413.
26. Gershon, A. A., (1992) *J. Inf. Des.* 166(Suppl) :563.
27. Glick, J. L., (1980) *Fundamentals of Human Lymphoid Culture*, Marcel Dokker, New York.
28. Gorbach, S. L., et al. (1992) *Infectious Disease* Ch.35:289, W. B. Saunders, Philadelphia, Pa.
29. Greenspan, et al. (1990) *J. Acquir. Immune Defic. Syndr.* 3 (6):571.
30. Hardy, I., et al. (1990) *Inf. Dis. Clin. N. Amer.* 4(1):159.
31. Hardy, I., et al. (1991) *New Enql. J. Med.* 325 (22):1545.
31A. Harel-Bellan, A., et al. (1988) *Exp. Med.* 168:2309–2318

32. Harlow and Lane, (1988) *Antibodies, A Laboratory Manual*, Cold Spring Harbor Publication, New York.
33. Haverkos, H. W., et al. (1985) *Sexually Transm. Dis.* 12:203.
34. Helene, C. and Toulme, J. (1990) *Biochim. Biophys. Acta.* 1049:99–125.
35. Heniford, et al. (1993) *Nucleic Acids Research* 21(14):3159–3166.
36. Higashi, K., et al. (1989) *J. Clin. Micro.* 27(10) :2204.
37. Holmberg, S. D., et al. (1990) *Cancer Detection and Prevention* 14:331.
38. Holliday, J., and Williams, M. V., (1992) *Antimicrob. Agents Chemother.* 36(9):1935.
39. Hoogenboom, H. R., et al. (1991) *Nuc. Acids Res.* 19:4133.
40. Hunt, et al. (1991) *Eur. J. Immunol.* 21:2963–2970.
41. *Hybridization of Nucleic Acids Immobilized on Solid Supports Meinkoth*, J. and Wahl, G.
42. *Hybridization with Nucleic Acid Probes* pp. 495–524, (1993) Elsevier, Amsterdam.
43. Ickes, et al. (1994) *Antiviral Research* 23, Seventh International Conf. on Antiviral Research, Abstract No. 122, Supp. 1.
44. Jahan, N., et al. (1989) *AIDS Research and Human Retroviruses* 5:225.
45. Jardetzkey, et al. (1991) *Nature* 353:326.
46. Johnston, G. S., et al. (1990) *Cancer Detection and Prevention* 14:337.
47. Jung, J. U., et al. (1991) *Proc. Natl. Acad. Sci. USA* 88:7051.
48. Kikuta, et al. (1989) *Lancet Oct.* 7:861.
49. Knowles, D. M., et al. (1989) *Blood* 73:792–798.
50. Kohler and Milstein, (1976) *Eur. J. Immunol.* 6:511–519.
51. Kucera, et al. (1993) *AIDS Res. Human Retroviruses* 9:307–314.
52. *Laboratory Techniques in Biochemistry and Molecular Biology* (1978) North Holland Publishing Company, New York.
53. Lasky, L. A., (1990) *J. Med. Virol.* 31(1):59.
54. Levin, M. J., et al. (1992) *J. Inf. Dis.* 166(2):253.
55. Lifson, A. R., et al. (1990) *Am. J. Epidemiol.* 131:221.
56. Lin, et al. (1991) *Antimicrob Agents Chemother* 35(11):2440–3.
57. Lin, J. C., et al. (1993) *Blood* 81:3372.
58. Lisitsyn, N., et al. (1993) *Science* 259:946.
59. Lo, S -C., et al. (1992) *Internat. J. Systematic Bacteriol.* 42:357.
60. Marks, J. D., et al. (1991) *J. Mol Biol.* 222:581–597.
61. Marloes, et al. (1991) *Eur. J. Immunol.* 21:2963–2970.
62. Matteucci, et al. (1981) *Am. Chem. Soc.* 103:3185.
63. Maxam, A. M. and Gilbert, W. *Methods in Enzymology* (1980) Grossman, L. and Moldave, D., eds., Academic Press, New York, 65:499–560.
64. McCafferty, J., et al. (1990) *Nature* 348:552.
65. Means and Feeney, (1990) *Bioconjugate Chem.* A recent reveiw of protein modification techniques, 1:2–12.
66. Metcalf, D. (1984) *Clonal Culture of Hematopoeitic Cells:Techniques and Applications*, Elvier, New York.
67. *Methods in Enzymology* Vol. 152, (1987) Berger, S. and Kimmel, A. ed., Academic Press, New York
68. Miller, G., *Virology* (1990) B. N. Fields, D.M. Knipe eds., Raven Press, New York, 2:1921.
69. Needham-VanDevanter, D.R., et al., (1984) *Nucelic Acids Res.* 12:6159–6168.
70. Needleman and Wunsch, (1970) *J. Mol. Biol.* 48:443.
71. Neuvo, et al. (1993) *American Journal of Surgical Pathology* 17(7), 683–690.
72. *Nucleic Acid Hybridization: A Practical Approach* (1985) Ed. Hames, B. D. and Higgins, S. J., IRL Press.
73. Oren and Soble, (1991) *Clinical Infectious Diseases* 14:741–6.
74. *PCR Protocols: A Guide to Methods and Applications*, (1990) Innis, M., Gelfand D., Sninsky, J. and White, T., eds., Academic Press, San Diego.
75. Pearson and Lipman, (1988) *Proc. Natl. Acad. Sci. (USA)* 85:2444.
75A. Pearson, J. D., and Regnier, F. E., (1983) *J. Chrom.* 255:137–14976.
76. Pellici, P. G., et al. (1985) *J. ExP. Med.* 162:1015.
77. Peterman, T. A., et al. (1991) *Cancer Surveys Imperial Cancer Research Fund, London,* 10:23–37.
78. Roizman, B. (1991) *Rev. Inf. Disease* 13 Suppl. 11:S892.
79. Rötzschke and Falk, (1991) *Immunol. Today* 12:447.
80. Safai, B., et al. (1980) *Cancer* 45:1472.
81. Sambrook, et al. (1989) *Molecular Cloning: A Laboratory Manual* (2nd ed.), Cold Spring Harbor Laboratory, Vols. 1–3.
82. Saunders, et al. (1990) *J. Acquir. Immune Defic. Syndr.* 3 (6):571.
83. Schecter, M. T., et al. (1991) *Am. J. Epidemiol.* 134:485.
84. Scopes, R., (1982) *Protein Purification:* Principles and PracticeSpringer-Verlag, New York.
85. Siddiqui, A., et al. (1983) *Proc. Natl. Acad. Sci. USA* 80:4861.
86. Skinner, G. R., et al. (1991) *Comp. Immuno. Microbiol. Inf. Dis.* 14(2):13.
87. Skinner, G. R., et al. (1992) *Med. Microbiol. Immunol.* 180(6):305. Smith and Waterman (1981) *Adv. Appl. Math.* 2:482.
88. Snoeck, et al. (1992) *Eur. J. Clin. Micro. Infect. Dis.* 11(12):1144–55.
89. Stals, et al. (1993) *Antimicrobial Agents Chemother.* 37(2):218–23.
90. van den Berg, F. et al. (1989) *J. Clin. Pathol.* 42:128.
91. Vogel, J., et al. (1988) *Nature* 335:606.
92. Wang, R. H. -Y., et al. (1993) *Clin. Infect. Dis.* 17:724.
93. Wickstrom, E. L., et al. (1988) *PNAS (USA)* 85:1028–1032.
94. Winkelmann, et al. (1988) *Drug Res.* 38, 1545–48.
95. Winkler, et al. (1990) *Antiviral Research* 14:61–74.
96. Yamandaka, et al. (1991) *Mol. Pharmacol.* 40(3):446.
97. Pellicer, A. et al. (1978) *Cell* 14:133–141.
98. Gibson, W. and Roizmann B. (1972) *J. Virol.* 10:1044–52.

EXPERIMENTAL DETAILS SECTION II

Sequencing Studies: A lambda phage (KS5) from a KS lesion genomic library identified by positive hybridization with KS330Bam was digested with BamHI and Not I (Boehringer-Mannheim, Indianapolis IN); five fragments were gel isolated and subcloned into Bluescript II KS (Stratagene, La Jolla Calif.). The entire sequence was determined by bidirectional sequencing at a seven fold average redundancy by primer walking and nested deletions.

DNA sequence data were compiled and aligned using ALIGN (IBI-Kodak, Rochester N.Y.) and analyzed using the Wisconsin Sequence Analysis Package Version 8-UNIX (Genetics Computer Group, Madison Wis.) and the GRAIL Sequence Analysis, Gene Assembly and Sequence Comparison System v. 1.2 (Informatics Group, Oak Ridge Tenn.). Protein site motifs were identified using Motif (Genetics Computer Group, Madison Wis.).

Sources of Herpesvirus Gene Sequence Comparisons: Complete genomic sequences of three gammaherpesviruses were available: Epstein-Barr virus (EBV), a herpesvirus of humans [4]; herpesvirus saimiri (HVS), a herpesvirus of the New World monkey Saimiri sciureus [1]; and equine herpesvirus 2 (EHV2 [49]). Additional thymidine kinase gene sequences were obtained for alcelaphine herpesvirus 1 (AHV1 [22]) and bovine herpesvirus 4 (BHV4 [31]). Sequences for the major capsid protein genes of human herpesvirus 6B and human herpesvirus 7 (HHV7) were from Mukai et al. [34]. The sources of all other sequences used are listed previously in McGeoch and Cook [31] and McGeoch et al. [32].

Phylogenetic Inference: Predicted amino acid sequences used for tree construction were based on previous experience with herpesviral phylogenetic analyses [31]. Alignments of homologous sets of amino acid sequences were made with the AMPS [5] and Pileup [16] programs. Regions of alignments that showed extreme divergence with marked length heterogeneity, typically terminal sections, were excised. Generally, positions in alignments that contained inserted gaps in one or more sequences were removed before use for tree construction. Phylogenetic inference programs were from the Phylip set, version 3.5 c [14] and from the GCG set [16]. Trees were built with the maximum parsimony (MP), neighbor joining (NJ) methods. For the NJ method, which utilizes estimates of pairwise distances between sequences, distances were estimated as mean numbers of substitution events per site with Protdist using the PAM 250 substitution probability matrix of Schwartz & Dayhoff [46]. Bootstrap analysis [15] was carried out for MP and NJ trees, with 100 sub-replicates of each alignment, and consensus trees obtained with the program Consense. In addition the program Protml was used to infer trees by the maximum likelihood (ML) method. Protml was obtained form J. Adachi, Department of Statistical Science, The Graduate University for Advanced Study, Tokyo 106, Japan. Because of computational constraints, Protml was used only with the 4-species CS1 alignment.

Clamped Homogeneous Electric Field (CHEF) Gel Electrophoresis: Agarose plugs were prepared by resuspending BCBL-1 cells in 1 LMP agarose (Biorad, Hercules Calif.) and 0.9% NaCl at 42° C. to a final concentration of $2.5 \times 10^7$ cells/ml. Solidified agarose plugs were transferred into lysis buffer (0.5M EDTA pH 8.0, 1% sarcosyl, proteinase K at 1 mg/ml final concentration) and incubated for 24 hours. Approximately $10^7$ BCBL-1 cells were loaded in each lane. Gels were run at a gradient of 6.0 V/cm with a run time of 28 h 28 min. on a CHEF Mapper XA pulsed field gel electrophoresis apparatus (Biorad, Hercules Calif.), Southern blotted and hybridized to KS627Bam, KS330Bam and an EBV terminal repeat sequence [40].

TPA Induction of Genome Replication: Late log phase BCBL-1 cells ($5 \times 10^5$ cells per ml) were incubated with varying amounts of 12-O-tetradecanoylphorbol-13-acetate (TPA, Sigma Chemical Co., St. Louis Mo.) for 48 h, cells were then harvested and washed with phosphate-buffered saline (PBS) and DNA was isolated by chloroform-phenol extraction. DNA concentrations were determined by UV absorbance; 5 $\mu$g of whole cell DNA was quantitatively dot blot hybridized in triplicate (Manifold I, Schleicher and Schuell, Keene NH). KS631Bam, EBV terminal repeat and beta-actin sequences were random-primer labeled with $^{32}$P [13]. Specific hybridization was quantitated on a Molecular Dynamics PhosphorImager 425E.

Cell Cultures and Transmission Studies: Cells were maintained at $5 \times 10^5$ cells per ml in RPMI 1640 with 20% fetal calf serum (FCS, Gibco-BRL, Gaithersburg Md.) and periodically examined for continued KSHV infection by PCR and dot hybridization. The T cell line Molt-3 (a gift from Dr. Jodi Black, Centers for Disease Control and Prevention), Raji cells (American Type Culture Collection, Rockville Md.) and RCC-1 cells were cultured in RPMI 1640 with 10% FCS. Owl monkey kidney cells (American Type Culture Collection, Rockville Md.) were cultured in MEM with 10% FCS and 1% nonessential amino acids (Gibco-BRL, Gaithersburg Md.).

To produce the RCC-1 cell line, $2 \times 10^6$ Raji cells were cultivated with $1.4 \times 10^6$ BCBL-1 cells in the presence of 20 ng/ml TPA for 2 days in chambers separated by Falcon 0.45 $\mu$g filter tissue culture inserts to prevent contamination of Raji with BCBL-1. Demonstration that RCC-1 was not contaminated with BCBL-1 was obtained by PCR typing of HLA-DR alleles [27] (Raji and RCC-1: DR$\beta$1*0310, DR$\beta$3*02; BCBL-1: DR$\beta$04,*07, Dr$\beta$4*01) and confirmed by flow cytometry to determine the presence (Raji, RCC1) or absence (BCBL-1) of EMA membrane antigen. Clonal sublines of RCC-1 were obtained by dilution in 96 well plates to 0.1 cells/well in RPMI 1640, 20% FCS and 30% T-STIM culture supplement (Collaborative Biomedical Products, Bedford Mass.). Subcultures were examined to ensure that each was derived from a single cluster of growing cells.

In situ hybridization was performed with a previously described 25 bp oligomer located in ORF26 which was 5' labeled with fluorescein (Operon, Alameda Calif.) and hybridized to cytospin preparations of BCBL-1, RCC-1 and Raji cells using the methods of Lungu et al. [29]. Slides were both directly visualized by UV microscopy and by incubating slides with anti-fluorescein-alkaline phosphatase (AP)-conjugated antibody (Boehringer-Mannheim, Indianapolis Ind.), allowing immunohistochemical detection of bound probe. Positive control hybridization was performed using a 26 bp TET-labeled EBV DNA polymerase gene oligomer (Applied Biosystems, Alameda Calif.) which was visualized by UV microscopy only and negative control hybridization was performed using a 25 bp 5' fluorescein-labeled HSV1 $\alpha$47 gene oligomer (Operon, Alameda Calif.) which was visualized in a similar manner as the KSHV ORF26 probe. All nuclei of BCBL-1, RCC-1 and Raji appropriately stained with the EBV hybridization probe whereas no specific staining of the cells occurred after hybridization with the HSV1 probe.

The remaining suspension cell lines used in transmission experiments were pelleted, and resuspended in 5 ml of 0.22 or 0.45$\mu$ filtered BCBL-1 tissue culture supernatant for 16 h. BCBL-1 supernatants were either from unstimulated cultures or from cultures stimulated with 20 ng/ml TPA. No difference in transmission to recipient cell lines was noted using various filtration or stimulation conditions. Fetal cord blood lymphocytes (FCBL) were obtained from heparinized fresh post-partum umbilical cord blood after separation on Ficoll-Paque (Pharmacia LKB, Uppsala Sweden) gradients and cultured in RPMI 1640 with 10% fetal calf serum. Adherent recipient cells were washed with sterile Hank's Buffered Salt Solution (HBSS, Gibco-BRL, Gaithersburg Md.) and overlaid with 5 ml of BCBL-l media supernatant. After incubation with BCBL-1 media supernatant, cells were washed three times with sterile HBSS, and- suspended in fresh media. Cells were subsequently rewashed three times every other day for six days and grown for at least two weeks prior to DNA extraction and testing. PCR to detect KSHV infection was performed using nested and unnested primers from ORF 26 and ORF 25 as previously described [10, 35].

Indirect Immunofluorescence Assay: AIDS-KS sera were obtained from ongoing cohort studies (provided by Drs.

Scott Holmberg, Thomas Spira and Harold Jaffe, Centers for Disease Control, and Prevention, and Isaac Weisfuse, New York City Department of Health). Sera from AIDS-KS patients were drawn between 1 and 31 months after initial KS diagnosis, sera from intravenous drug user and homosexual/bisexual controls were drawn after non-KS AIDS diagnosis, and sera from HIV-infected hemophiliac controls were drawn at various times after HIV infection. Immunofluorescence assays were performed using an equal volume mixture of goat anti-human IgG-FITC conjugate (Molecular Probes, Eugene OR) and goat anti-human IgM-FITC conjugate (Sigma Chemical Co., St. Louis Mo.) diluted 1:100 and serial dilutions of patient sera. End-point titers were read blindly and specific immunoglobulin binding was assessed by the presence or absence of a specular fluorescence pattern in the nuclei of the plated cells. To adsorb cross-reacting antibodies, 20 μl serum diluted 1:10 in phosphate-buffer saline (PBS), pH 7.4, were adsorbed with $1-3\times10^7$ paraformaldehyde-fixed P3H3 cells for 4–10 h at 25° C. and removed by low speed centrifugation. P3H3 were induced prior to fixation with 20 ng/ml TPA for 48 h, fixed with 1% paraformaldehyde in PBS for 2 h at 4° C., and washed three times in PBS prior to adsorption.

RESULTS

Sequence Analysis of a 20.7 kb KSHV DNA Sequence: To demonstrate that KS330Bam and KS631Bam are genomic fragments from a new and previously uncharacterized herpesvirus, a lambda phage clone (KS5) derived from an AIDS-KS genomic DNA library was identified by hybridization to the KS330Bam sequence. The KS5 insert was subcloned after NotI/BamHI digestion into five subfragments and both strands of each fragment were sequenced by primer walking or nested deletion with a 7-fold average redundancy. The KS5 sequence is 20,705 bp in length and has a G+C content of 54.0%. The observed/expected CpG dinucleotide ratio is 0.92 indicating no overall CpG suppression in this region. Open reading frame (ORF) analysis identified 15 complete ORFs with coding regions ranging from 231 bp to 4128 bp in length, and two incomplete ORFs at the termini of the KS5 clone which were 135 and 552 bp in length (FIG. 12). The coding probability of each ORF was analyzed using GRAIL 2 and CodonPreference which identified 17 regions having excellent to good protein coding probabilities. Each region is within an ORF encoding a homolog to a known herpesvirus gene with the exception of one ORF located at the genome position corresponding to ORF28 in herpesvirus saimiri (HVS). Codon preference values for all of the ORFs were higher across predicted ORFs than in non-coding regions when using a codon table composed of KS5 homologs to the conserved herpesvirus major capsid (MCP), glycoprotein H (gH), thymidine kinase (TK), and the putative DNA packaging protein (ORF29a/ORF29b) genes.

The translated sequence of each ORF was used to search GenBank/EMBL databases with BLASTX and FastA algorithms [2, 38]. All of the putative KS5 ORFs, except one, have sequence and collinear positional homology to ORFs from gamma-2 herpesviruses, especially HVS and equine herpesvirus 2 (EHV2). Because of the high degree of collinearity and amino acid sequence similarity between KSHV and HVS, KSHV ORFs have been named according to their HVS positional homologs (i.e. KSHV ORF25 is named after HVS ORF 25).

The KS5 sequence spans a region which includes three of the seven conserved herpesvirus gene blocks (FIG. 14) [10]. ORFs present in these blocks include genes which encode herpesvirus virion structural proteins and enzymes involved in DNA metabolism and replication. Amino acid identities between KS5 ORFs and HVS ORFs range from 30% to 60%, with the conserved MCP ORF25 and ORF29b genes having the highest percentage amino acid identity to homologs in other gammaherpesviruses. KSHV ORF28, which has no detectable sequence homology to HVS or EBV genes, has positional homology to HVS ORF28 and EBV BDLF3. ORF28 lies at the junction of two gene blocks (FIG. 14); these junctions tend to exhibit greater sequence divergence than intrablock regions among herpesviral genomes [17]. Two ORFs were identified with sequence homology to the putative spliced protein packaging genes of HVS (ORF29a/ORF29b) and herpes simplex virus type 1 (UL15). The KS330Bam sequence is located within KSHV ORF26, whose HSV-1 counterpart, VP23, is a minor virion structural component.

For every KSHV homolog, the HVS amino acid similarity spans the entire gene product, with the exception of ORF21, the TK gene. The KSHV TK homolog contains a proline-rich domain at its amino terminus (nt 20343–19636; aa 1-236) that is not conserved in other herpesvirus TK sequences, while the carboxyl terminus (nt 19637–18601; aa 237–565) is highly similar to the corresponding regions of HVS, EHV2, and bovine herpesvirus 4 (BHV4) TK. A purine binding motif with a glycine-rich region found in herpesviral TK genes, as well as other TK genes, is present in the KSHV TK homolog (GVMGVGKS; aa 260–267).

The KS5 translated amino acid sequences were searched against the PROSITE Dictionary of Protein Sites and Patterns (Dr. Amos Bairoch, University of Geneva, Switzerland) using the computer program Motifs. Four sequence motif matches were identified among KSHV hypothetical protein sequences. These matches included: (i) a cytochrome c family heme-binding motif in ORF33 (CVHCHG; aa 209–214) and ORF34 (CLLCHI; aa 257–261), (ii) an immunoglobulin and major histocompatibility complex protein signature in ORF25 (FICQAKH; aa 1024–1030), (iii) a mitochondrial energy transfer protein motif in ORF26 (PDDITRMRV; aa 260–268), and (iv) the purine nucleotide binding site identified in ORF21. The purine binding motif is the only motif with obvious functional significance. A cytosine-specific methylase motif present in HVS ORF27 is not present in KSHV ORF27. This motif may play a role in the methylation of episomal DNA in cells persistently infected with HVS [1].

Phylogenetic Analysis of KSHV: Amino acid sequences translated from the KS5 sequence were aligned with corresponding sequences from other herpesviruses. On the basis of the level of conserved aligned residues and the low incidence of introduced gaps, the amino acid alignments for ORFs 21, 22, 23, 24, 25, 26, 29a, 29b, 31 and 34 were suitable for phylogenetic analyses.

To demonstrate the phylogenetic relationship of KSHV to other herpesviruses, a single-gene comparison was made for ORF25 (MCP) homologs from KS5 and twelve members of Herpesviridae (FIGS. 15A–15B). The thirteen available MCP amino acid sequences are large (1376 a.a. residues for the KSHV homolog) and alignment required only a low level of gapping; however, the overall similarity between viruses is relatively low [33]. The MCP set gave stable trees with high bootstrap scores and assigned the KSHV homolog to the gamma-2 sublineage (genus Rhadinovirus), containing HVS, EHV2 and BVH4 [20, 33, 43]. KSHV was most closely associated with HVS. Similar results were obtained for single-gene alignments of TK and UL15/ORF29 sets but with lower bootstrap scores so that among gamma-2 herpesvirus members branching orders for EHV2, HVS and KSHV were not resolved.

To determine the relative divergence between KSHV and other gammaherpesviruses, alignments for the nine genes listed above were concatenated to produce a combined gammaherpesvirus gene set (CSi) containing EBV, EHV2, HVS and KSHV amino acid sequences. The total length of CS1 was 4247 residues after removal of positions containing gaps introduced by the alignment process in one or more of the sequences. The CS1 alignment was analyzed by the ML method, giving the tree shown in FIG. 15B and by the MP and NJ methods used with the aligned herpesvirus MCP sequences. All three methods identified KSHV and HVS as sister groups, confirming that KSHV belongs in the gamma-2 sublineage with HVS as its closest known relative. It was previously estimated that divergence of the HVS and EHV2 lineages may have been contemporary with divergence of the primate and ungulate host lineages [33]. The results for the CS1 set suggest that HVS and KSHV represent a lineage of primate herpesviruses and, based on the distance between KSHV and HVS relative to the position of EHV2, divergence between HVS and KSHV lines is ancient.

Genomic Studies of KSHV:

CHEF electrophoresis performed on BCBL-1 cells embedded in agarose plugs demonstrated the presence of a nonintegrated KSHV genome as well as a high molecular weight species (FIGS. 16A–16B). KS631Bam (FIG. 16A) and KS330Bam specifically hybridized to a single CHEF gel band comigrating with 270 kilobase (kb) linear DNA standards. The majority of hybridizing DNA was present in a diffuse band at the well origin; a low intensity high molecular weight (HMW) band was also present immediately below the origin (FIG. 16A. arrow). The same filter was stripped and probed with an EBV terminal repeat sequence [40] yielding a 150–160 kb band (FIG. 16B) corresponding to linear EBV DNA [24]. The HMW EBV band may correspond to either circular or concatemeric EBV DNA [24].

The phorbol ester TPA induces replication-competent EBV to enter a lytic replication cycle [49]. To determine if TPA induces replication of KSHV and EBV in BCBL-l cells, these cells were incubated with varying concentrations of TPA for 48 h (FIG. 17). Maximum stimulation of EBV occurred at 20 ng/ml TPA which resulted in an eight-fold increase in hybridizing EBV genome. Only a 1.3–1.4 fold increase in KSHV genome abundance occurred after 20–80 ng/ml TPA incubation for 48 h.

Transmission Studies

Prior to determining that the agent was likely to be a member of Herpesviridae by sequence analysis, BCBL-1 cells were cultured with Raji cells, a-nonlytic EBV transformed B cell line, in chambers separated by a $0.45\mu$ tissue culture filter. Recipient Raji cells generally demonstrated rapid cytolysis suggesting transmission of a cytotoxic component from the BCBL-1 cell line. One Raji line cultured in 10 ng/ml TPA for 2 days, underwent an initial period of cytolysis before recovery and resumption of logarithmic growth. This cell line (RCC-1) is a monoculture derived from Raji uncontaminated by BCBL-1 as determined by PCR amplification of HLA-DR sequences.

RCC-1 has remained positive for the $KS330_{233}$ PCR product for >6 months in continuous culture (approximately 70 passages), but KSHV was not detectable by dot or Southern hybridization at any time. In situ hybridization, however, with a 25 bp KSHV ORF26-derived oligomer was used to demonstrate persistent localization of KSHV DNA to RCC-1 nuclei. As indicated in FIGS. 18A–18C, nuclei of BCBL-1 and RCC-1 (from passage ~65) cells had detectable hybridization with the ORF26 oligomer, whereas no specific hybridization occurred with parental Raji cells (FIG. 18B). KSHV sequences were detectable in 65% of BCBL-1 and 2.6% of RCC-1 cells under these conditions. In addition, forty-five monoclonal cultures were subcultured by serial dilution from RCC-1 at passage 50, of which eight (18%) clones were PCR positive by $KS330_{233}$. While PCR detection using unnested $KS330_{233}$ primer pairs was lost by passage 15 in each of the clonal cultures, persistent KSHV genome was detected in 5 clones using two more sensitive nonoverlapping nested PCR primer sets [33] suggesting that KSHV genome is lost over time in RCC-1 and its clones.

Low but persistent levels of $KS330_{233}$ PCR positivity were found for one of four Raji, one of four Bjab, two of three Molt-3, one of one owl monkey kidney cell lines and three of eight human fetal cord blood lymphocyte (FCBL) cultures after inoculation with $0.2–0.45\mu$ filtered BCBL-1 supernatants. Among the PCR positive cultures, PCR detectable genome was lost after 2–6 weeks and multiple washings. Five FCBL cultures developed cell clusters characteristic of EBV immortalized lymphocytes and were positive for EBV by PCR using EBER primers [23]; three of these cultures were also initially $KS330_{233}$ positive. None of the recipient cell lines had detectable KSHV genome by dot blot hybridization.

Serologic Studies:

Indirect immunofluorescence antibody assays (IFA) were used to assess the presence of specific antibodies against the KSHV- and EBV-infected cell line BHL-6 in the sera from AIDS-KS patients and control patients with HIV infection or AIDS. BHL-6 was substituted for BCBL-1 for reasons of convenience; preliminary studies showed no significant differences in IFA results between BHL-6 and BCBL-1. BHL-6 have diffuse immunofluorescent cell staining with most KS patient and control unabsorbed sera suggesting nonspecific antibody binding (FIGS. 19A–19D). After adsorption with paraformaldehyde-fixed, TPA-induced P3H3 (an EBV producer subline of P3J-HR1, a gift of Dr. George Miller) to remove cross-reacting antibodies against EBV and lymphocyte antigens, patient sera generally showed specular nuclear staining at high titers while this staining pattern was absent from control patient sera (FIGS. 19B and 19D). Staining was localized primarily to the nucleus but weak cytoplasmic staining was also present at low sera dilutions.

With unadsorbed sera, the initial endpoint geometric mean titers (GMT) against BHL-6 cell antigens for the sera from AIDS-KS patients (GMT=1:1153, range: 1:150 to 1:12,150) were higher than for sera from control, non-KS patients (GMT=1:342; range 1:50 to 1:12,150; p=0.04) (FIG. 13). While AIDS-KS patients and HIV-infected gay/bisexual and intravenous drug user control patients had similar endpoint titers to BHL-6 antigens (GMT=1:1265 and GMT=1:1578, respectively), hemophilic AIDS patient titers were lower (GMT=1:104). Both case and control patient groups had elevated IFA titers against the EBV infected cell line P3H3.

The difference in endpoint GMT between case and control titers against BHL-6 antigens increased after adsorption with P3H3. After adsorption, case GMT declined to 1:780 and control GMT declined to 1:81 (p=0.00009). Similar results were obtained by using BCBL-1 instead of BHL-6 cells, by pre-adsorbing with EBV-infected nonproducer Raji cells instead of P3H3 and by using sera from a homosexual male KS patient without HIV infection, in complete remission for KS for 9 months (BHL-6 titer 1:450, P3H3 titer 1:150). Paired sera taken 8–14 months prior to KS onset and after KS onset were available for three KS patients: KS patients 8 and 13 had eight-fold rises and patient 8 had a three-fold fall in P3H3-adsorbed BCBL-1 titers from pre-onset sera to post-KS sera.

DISCUSSION

These studies demonstrate that specific DNA sequences found in KS lesions by representational difference analysis belong to a newly identified human herpesvirus. The current studies define this agent as a human gamma-2 herpesvirus that can be continuously cultured in naturally-transformed, EBV-coinfected lymphocytes from AIDS-related body-cavity based lymphomas.

Sequence analysis of the K5 lambda phage insert provides clear evidence that the KS330Bam sequence is part of a larger herpesvirus genome. KS5 has a 54.0% G+C content which is considerably higher than the corresponding HVS region (34.3% G+C). While there is no CpG dinucleotide suppression in the KS5 sequence, the corresponding HVS region has a 0.33 expected:observed CpG dinucleotide ratio [1]. The CpG dinucleotide frequency in herpesviruses varies from global CpG suppression among gammaherpesviruses to local CpG suppression in the betaherpesviruses, which may result from deamination of 5'-methylcytosine residues at CpG sites resulting in TpG substitutions [21]. CpG suppression among herpesviruses [21, 30, 44] has been hypothesized to reflect co-replication of latent genome in actively dividing host cells, but it is unknown whether or not KSHV is primarily maintained by a lytic replication cycle in vivo.

The 20,705 bp KS5 fragment has 17 protein-coding regions, 15 of which are complete ORFs with appropriately located TATA and polyadenylation signals, and two incomplete ORFs located at the phage insert termini. Sixteen of these ORFs correspond by sequence and collinear positional homology to 15 previously identified herpesviral genes including the highly conserved spliced gene. The conserved positional and sequence homology for KSHV genes in this region are consistent with the possibility that the biological behavior of the virus is similar to that of other gammaherpesviruses. For example, identification of a thymidine kinase-like gene on KS5 implies that the agent is potentially susceptible to TK-activated DNA polymerase inhibitors and like other herpesviruses possesses viral genes involved in nucleotide metabolism and DNA replication [41]. The presence of major capsid protein and glycoprotein H gene homologs suggest that replication competent virus would produce a capsid structure similar to other herpesviruses.

Phylogenetic analyses of molecular sequences show that KSHV belongs to the gamma-2 sublineage of the Gammaherpesvirinae subfamily, and is thus the first human gamma-2 herpesvirus identified. Its closest known relative based on available sequence comparisons is HVS, a squirrel monkey gamma-2 herpesvirus that causes fulminant polyclonal T cell lymphoproliferative disorders in some New World monkey species. Data for the gamma-2 sublineage are sparse: only three viruses (KSHV, HVS and EHV2) can at present be placed on the phylogenetic tree with precision (the sublineage also contains murine herpesvirus 68 and BHV4 [33]). Given the limitation in resolution imposed by this thin background, KSHV and HVS appear to represent a lineage of primate gamma-2 viruses. Previously, McGeoch et al. [33] proposed that lines of gamma-2 herpesviruses may have originated by cospeciation with the ancestors of their host species. Extrapolation of this view to KSHV and HVS suggests that these viruses diverged at an ancient time, possibly contemporaneously with the divergence of the old World and New World primate host lineages. Gammaherpesviruses are distinguished as a subfamily by their lymphotrophism [41] and this grouping is supported by phylogenetic analysis based on sequence data [33]. The biologic behavior of KSHV is consistent with its phylogenetic designation in that KSHV can be found in in vitro lymphocyte cultures and in in vivo samples of lymphocytes [3].

This band appears to be a linear form of the genome because other "high molecular weight" bands are present for both EBV and KSHV in BCBL-1 which may represent circular forms of their genomes. The linear form of the EBV genome, associated with replicating and packaged DNA [41] migrates substantially faster than the closed circular form associated with latent viral replication [24]. While the 270 kb band appears to be a linear form, it is also consistent with a replicating dimer plasmid since the genome size of HVS is approximately 135 kb. The true size of the genome may only be resolved by ongoing mapping and sequencing studies.

Replication deficient EBV mutants are common among EBV strains passaged through prolonged tissue culture [23]. The EBV strain infecting Raji, for example, is an BALF-2 deficient mutant [19]; virus replication is not inducibile with TPA and its genome is maintained only as a latent circular form [23, 33] The EBV strain coinfecting BCBL-1 does not appear to be replication deficient because TPA induces eight-fold increases in DNA content and has an apparent linear form on CHEF electrophoresis. KSHV replication, however, is only marginally induced by comparable TPA treatment indicating either insensitivity to TPA induction or that the genome has undergone loss of genetic elements required for TPA induction. Additional experiments, however, indicate that KSHV DNA can be pelleted by high speed centrifugation of filtered organelle-free, DNase I-protected BCBL-1 cell extracts, which is consistent with KSHV encapsidation.

Transmission of KSHV DNA from BCBL-1 to a variety of recipient cell lines is possible and KSHV DNA can be maintained at low levels in recipient cells for up to 70 passages. However, detection of virus genome in recipient cell lines by PCR may be due to physical association of KSHV DNA fragments rather than true infection. This appears to be unlikely given evidence for specific nuclear localization of the ORF26 sequence in RCC-1. If transmission of infectious virus from BCBL-1 occurs, it is apparent that the viral genome declines in abundance with subsequent passages of recipient cells. This is consistent with studies of spindle cell lines derived from KS lesions. Spindle cell cultures generally have PCR detectable KSHV genome when first explanted, but rapidly lose viral genome after initial passages and established spindle cell cultures generally do not have detectable KSHV sequences [3].

Infections with the human herpesviruses are generally ubiquitous in that nearly all humans are infected by early adulthood with six of the seven previously identified human herpesviruses [42]. Universal infection with EBV, for example, is the primary reason for the difficulty in clearly establishing a causal role for this virus in EBV-associated human tumors. The serologic studies identified nuclear antigen in BCBL-1 and BHL-6 which is recognized by sera from AIDS-KS patients but generally not by sera from control AIDS patients without KS after removal of EBV-reactive antibodies. These data are consistent with PCR studies of KS and control patient lymphocytes suggesting that KSHV is not ubiquitous among adult humans, but is specifically associated with persons who develop Kaposi's sarcoma. In this respect, it appears to be epidemiologically similar to HSV2 rather than the other known human herpesviruses. An alternative possibility is that elevated IFA titers against BCBL-1 reflect disease status rather than infection with the virus.

REFERENCES

1. Albrecht, J.-C., J. Nicholas, D. Biller, K. R. Cameron, B. Biesinger, C. Newamn, S. Wittmann, M. A. Craxton, H. Coleman, B. Fleckenstein, and R. W. Honess. 1992. Primary structure of the Herpesvirus saimiri genome. J Virol. 66:5047–5058.
2. Altschul, S. F., W. Gish, W. Miller, E. W. Myers, and D. J. Lipman. 1990. Basic local alignment search tool. J Mol Biol. 215:403–410.
3. Ambroziak, J. A., D. J. Blackbourn, B. G. Herndier, R. G. Glogau, J. H. Gullett, A. R. McDonald, E. T. Lennette, and J. A. Levy. 1995. Herpes-like sequences in HIV-infected and uninfected Kaposi's sarcoma patients. Science. 268:582–583.
4. Baer, R., A. T. Bankier, P. L. Biggin, P. L. Deininger, P. J. Farrell, T. J. Gibson, G. Hatfull, G. S. Hudson, S. C. Satchwell, C. Seguin, P. S. Tuffnell, and B. G. Barrell. 1984. DNA sequence and expression of the B95-8 Epstein-Barr virus genome. Nature. 310:207–211.
5. Barton, G. J., and M. J. E. Sternberg. 1987. A strategy for the rapid multiple alignment of protein sequences. Confidence levels from tertiary structure comparisons. J Mol Biol. 198:327–37.
6. Beral, V., T. A. Peterman, R. L. Berkelman, and H. W. Jaffe. 1990. Kaposi's sarcoma among persons with AIDS: a sexually transmitted infection? Lancet. 335:123–128.
7. Boshoff, C., D. Whitby, T. Hatziionnou, C. Fisher, J. van der Walt, A. Hatzakis, R. Weiss, and T. Schulz. 1995. Kaposi's sarcoma-associated herpesvirus in HIV-negative Kaposi's sarcoma. Lancet. 345:1043–44.
8. Cesarman, E., Y. Chang, P. S. Moore, J. W. Said, and D. M. Knowles. 1995. Kaposi's sarcoma-associated herpesvirus-like DNA sequences are present in AIDS-related body cavity based lymphomas. New England J Med. 332:1186–1191.
9. Chang, Y., E. Cesarman, M. S. Pessin, F. Lee, J. Culpepper, D. M. Knowles, and P. S. Moore. 1994. Identification of herpesvirus-like DNA sequences in AIDS-associated Kaposi's sarcoma. Science. 265:1865–69.
10. Chee, M. S., S. B. Bankier, C. M. Bohni, R. C. Brown, T. Horsnell, C. A. Hutchison, T. Kouzarides, J. A. Martignetti, E. Preddie, S. C. Satchwell, P. Tomlinson, K. M. Weston, and B. G. Barrell. 1990. Analysis of the protein coding content of the sequence of cytomegalovirus strain AD169. Curr Top Microbiol Immunol. 154:125–69.
11. Collandre, H., S. Ferris, 0. Grau, L. Montagnier, and A. Blanchard. 1995. Kaposi's sarcoma and new herpesvirus. Lancet. 345:1043.
12. Dupin, N., M. Grandadam, V. Calvez, I. Gorin, J. T. Aubin, S. Harvard, F. Lamy, M. Leibowitch, J. M. Huraux, J. P. Escande, and H. Agut. 1995. Herpesvirus-like DNA in patients with Mediterranean Kaposi's sarcoma. Lancet. 345:761–2.
13. Feinberg, A. P., and B. Vogelstein. 1983. A technique for radiolabeling DNA restriction endonuclease fragments to high specific activity. Anal Biochem. 132:6.
14. Felsenstein, J. 1989. PHYLIP-phylogeny inference package (ver 3.2). Cladistics. 5:164–6.
15. Felsenstein, J. 1988. Phylogenies from molecular sequences: inferences and reliability. Annual Rev Microbiol. 22:521–65.
16. Genetics Computer Group. 1994. Program manual for the GCG package, version 8, Madison, Wis.
17. Gompels, U. A., J. Nicholas, G. Lawrence, M. Jones, B. J. Thomson, M. E. D. Martin, S. Efstathiou, M. Craxton, and H. A. Macaulay. 1995. The DNA sequence of human herpesvirus-6: Structure, coding content and genome evolution. Virology. 209:29–51.
18. Hatfull, G., A. T. Bankier, B. G. Barrell, and P. J. Farrell. 1988. Sequence analysis of Raji Epstein-Barr virus DNA. Virol. 164:334–40.
19. Holmberg, S. D. 1990. Possible cofactors for the development of AIDS-related neoplasms. Cancer Detection and Prevention. 14:331–336.
20. Honess, R. W. 1984. Herpes simplex and 'the herpes complex': diverse observations and a unifying hypothesis. J Gen Virol. 65:2077–2107.
21. Honess, R. W., U. A. Gompels, B. G. Barrell, M. Craxton, K. R. Cameron, R. Staden, Y.-N. Chang, and G. S. Hayward. 1989. Deviations from expected frequencies of CpG dinucleotides indiagnostic of NAs may be diagnostic of differences in the states of their latent genomes. J Gen Virol. 70:837–55.
22. Hsu, D., L. M. Shih, and Y. C. Zee. 1990. Nucleotide sequence of a 3.5 nucleotide fragment of malignant catarrhal fever virus strain WC11. Arch Virol. 113:53–60.
23. Kieff, E., and D. Liebowitz. 1990. Epstein-Barr virus and its replication, p. 1889–1920. In B. N. Fields and D. M. Knipe (ed.), Virology, vol. 2. Raven Press, New York.
24. Kolman, J. L., C. J. Kolman, and G. Miller. 1992. Marked variation in the size of genomic plasmids among members of the family of related Epstein-Barr viruses. Proc Natl Acad Sci, USA. 89:7772–7776.
25. Lebbé, C., P. de Cremoux, M. Rybojad, C. Costa da Cunha, P. Morel, and F. Calvo. 1995. Kaposi's sarcoma and new herpesvirus. Lancet. 345:1180.
26. Lin, J. C., S. C. Lin, B. K. De, W. P. Chan, and B. L. Evatt. 1993. Precision of genotyping of Epstein-Barr virus by polymerase chain reaction using three gene loci (EBNA-2, EBNA-3C and EBER): predominance of type A virus associated with Hodgkin's disease. Blood. 81:3372–81.
27. Liu, Z., S. Yu-Kai, Y.-P. Xi, P. Harris, and N. Suciu-Foca. 1992. T cell recognition of self-human histocompatibility leukocyte antigens (HLA)-DR peptides in the context of syngeneic HLA-DR molecules. J Exp Med. 175:1663–8.
28. Lomonte, P., M. Bublot, P—P. Pastoret, and E. Thiry. 1992. Location and characterization of the bovine herpesvirus type 4 thymidine kinase gene; comparison with thymidine kinase of other herpesviruses. Arch. Virol. 127:327–337.
29. Martin, M. E. D., J. Nicholas, B. J. Thomson, C. Newman, and R. W. Honess. 1991. Identification of a transactivating function mapping to the putative immediate-early locus of human herpesvirus 6. J Virol. 65:5381–5390.
30. McGeoch, D. J., and S. Cook. 1994. Molecular phylogeny of the Alphaherpesvirinae subfamily and a proposed evolutionary timescale. J Mol Biol. 238:9–22.
31. McGeoch, D. J., S. Cook, A. Dolan, F. E. Jamieson, and E. A. R. Telford. 1995. Molecular phylogeny and evolutionary timescale for the family of mammalian herpesviruses. J Molec Biol. 247:443–58.
32. Miller, G. 1990. Epstein-Barr virus: Biology, pathogenesis and medical aspects, p. 1921–1957. In B. N. Fields and D. M. Knipe (ed.), Virology, 2nd ed, vol. 2. Raven Press, New York.
33. Moore, P. S., and Y. Chang. 1995. Detection of herpesvirus-like DNA sequences in Kaposi's sarcoma lesions from persons with and without HIV infection. New England J Med. 332:1181–1185.
34. Mukai, T., Y. Isegawa, and K. Yamanishi. 1995. Identification of the major capsid protein gene of human herpesvirus 7. Virus Res. 37:55–62.
35. Oettle, A. G. 1962. Geographic and racial differences in the frequency of Kaposi's sarcoma as evidence of environmental or genetic causes, vol. 18. Symposium on Kaposi's sarcoma: Unio Internationalis Contra Cancrum, Karger, Basel. 36. Pearson, W. R., and D. J. Lipman. 1988. Improved tools for biological sequence analysis. Proc Natl Acad Sci, USA. 85:2444–8.
37. Peterman, T. A., H. W. Jaffe, A. E. Friedman-Kien, and R. A. Weiss. 1991. The aetiology of Kaposi's sarcoma, p. 23–37, Cancer, HIV, and AIDS, vol. 10. Imperial Cancer Research Fund. London.
38. Raab-Traub, N., and K. Flynn. 1986. The structure of the termini of the Epstein-Barr virus as a marker of clonal cellular proliferation. Cell. 47:883–889.
39. Roizman, B. 1993. The family Herpesviridae, p. 1–9. In B. Roizman and R. J. Whitley and C. Lopez (ed.), The Human Herpeviruses. Raven Press, Ltd., New York.
40. Roizman, B. 1995. New viral footprints in Kaposi's sarcoma. N Engl J Med. 332:1227–1228.
41. Roizman, B., R. C. Desrosiers, B. Fleckenstein, C. Lopez, A. C. Minson, and M. J. Studdert. 1992. The family Herpesviridae: an update. Arch Virol. 123:425–449.
42. Sandford, G. R., K. Ho, and W. H. Burns. 1993. Characterization of the major locus of immediate-early genes of rat cytomegalovirus. J Virol. 67:4093–4103.
43. Schalling, M., M. Ekman, E. E. Kaaya, A. Linde, and P. Bieberfeld. 1995. A role for a new herpesvirus (KSHV) in different forms of Kaposi's sarcoma. Nature Med. 1:707–8.
44. Schwartz, R. M., and M. 0. Dayhoff. 1978. Matrices for detecting distant relationships, p. 353–8. In M. 0. Dayhoff (ed.), Atlas of protein sequence and structure, vol. 5, supple 3. National Biomedical Research Foundation, Washington.
45. Su, I.-J., Y.-S. Hsu, Y.-C. Chang, and I.-W. Wang. 1995. Herpesvirus-like DNA sequence in Kaposi's sarcoma from AIDS and non-AIDS patients in Taiwan. Lancet. 345:722–23.
46. Telford, E. A. R., M. S. Watson, H. C. Aird, J. Perry, and A. J. Davison. 1995. The DNA sequence of equine herpesvirus 2. J Molec Biol. 249:520–8.
47. zur Hausen, H., F. J. O'Neill, and U. K. Freese. 1978. Persisting oncogenic herpesvirus induced by the tumor promoter TPA. Nature. 272:373–375.

EXPERIMENTAL DETAILS SECTION III

KS Patient Enrollment: Cases and controls were selected from ongoing cohort studies based on the availability of clinical information and appropriate PBMC samples. 21 homosexual or bisexual men with AIDS who developed KS during their participation in prospective cohort studies were identified [14–16]. Fourteen of these patients had paired PBMC samples collected after KS diagnosis (median +4 months) and at least four months prior to KS diagnosis (median -13 months), while the remaining 7 had paired PBMC taken at the study visit immediately prior to KS diagnosis (median -3 months) and at entry into their cohort study (median -51 months prior to KS diagnosis).

Hemophilic and Homosexual/Bisexual Male AIDS Patient Control Enrollment: Two control groups of AIDS patients were examined: 23 homosexual/bisexual men with AIDS followed until death who did not develop KS ("high risk" control group) from the Multicenter AIDS Cohort Study [16]), and 19 hemophilic men ("low risk" control group) enrolled from joint projects of the National Hemophilia Foundation and the Centers for Disease Control and Prevention. Of the 16 hemophilic controls with available follow-up information, none are known to have developed KS and <2% of hemophilic AIDS patients historically develop KS [2]. For homosexual/bisexual AIDS control patients who did not develop KS, paired PBMC specimens were available at entry into their cohort study (median -35 months prior to AIDS onset) and at the study visit immediately prior to nonKS AIDS diagnosis (median BHL-6 months prior to AIDS onset).

DNA Extraction and Analyses: DNA from $10^6$–$10^7$ PBMC in each specimen was extracted and quantitated by spectrophotometry. Samples were prepared in physically isolated laboratories from the laboratory where polymerase chain reaction (PCR) analyses were performed. All samples were tested for amplifiability using primers specific for either the HLA-DQ locus (GH26/GH27) or b-globin [18]. PCR detection of KSHV DNA was performed as previously described [7] with the following nested primer sets: No. 1 outer 5'-AGCACTCGCAGGGCAGTACG-3', 5'-GACTCTTCGCTGATGAACTGG-3'; No. 1 inner 5'-TCCGTGTTGTCTACGTCCAG-3', 5'-AGCCGAAAGGATTCCACCAT-3'; No. 2 outer 5'-AGGCAACGTCAGATGTGAC-3', 5'-GAAATTACCCACGAGATCGC-3'; No. 2 inner 5'-CATGGGAGTACATTGTCAGGACCTC-3', 5'-GGAATTATCTCGCAGGTTGCC-3'; No. 3 outer 5'-GGCGACATTCATCAACCTCAGGG-3', 5'-ATATCATCCTGTGCGTTCACGAC-3'; No. 3 inner 5'-CATGGGAGTACATTGTCAGGACCTC-3', 5'-GGAATTATCTCGCAGGTTGCC-3'. The outer primer set was amplified for 35 cycles at 94° C. for 30 seconds, 60° C. for 1 minute and 72° C. for 1 minute with a 5 minute final extension cycle at 72° C. One to three ml of the PCR product was added to the inner PCR reaction mixture and amplified for 25 additional cycles with a 5 minute final extension cycle. Primary determination of sample positivity was made with primer set No. 1 and confirmed with either primer sets 2 or 3 which amplify nonoverlapping regions of the KSHV hypothetical major capsid gene. Sampling two portions of the KSHV genome decreased the likelihood of intraexperimental PCR contamination. These nested primer sets are 2–3 logs more sensitive for detecting KSHV sequences than the previously published $KS330_{233}$ primers [6] and are estimated to be able to detect <10 copies of KSHV genome under optimal conditions. Sample preparations were prealiquoted and amplified with alternating negative control samples without DNA to monitor and control possible contamination. All samples were tested in a blinded fashion and a determination of the positivity/negativity made before code breaking. Significance testing was performed with Mantel-Haenszel chi-squared estimates and exact confidence intervals using Epi-Info ver. 6 (USD Inc., Stone Mt. Ga.).

RESULTS

KSHV Positivity of Case and Control PBMC Samples:
Paired PBMC samples were available from each KS patient and homosexual/bisexual control patient; a single sample was available from each hemophilic control patient.
To determine the KSHV positivity rate for each group of AIDS patients, a single specimen from each participant taken closest to KS or other AIDS-defining illness ("second sample") was analyzed. Overall, 12 of 21 (57%) of PBMC specimens from KS patients taken from 6 months prior to KS diagnosis to 20 months after KS diagnosis were KSHV positive. There was no apparent difference in positivity rate between immediate pre-diagnosis and post-diagnosis visit specimens (4 of 7 (57%) vs. 8 of 14 (57%) respectively).

The number of KSHV positive control PBMC specimens from both homosexual/bisexual (second visit) and hemophilic patient controls was significantly lower. Only 2 of 19 (11%) hemophilic PBMC samples were positive (odds ratio 11.3, 95% confidence interval 1.8 to 118) and only 2 of 23 (9%) PBMC samples from homosexual/bisexual men who did not develop KS were positive (odds ratio 14.0, 95% confidence interval 2.3 to 144). If all KS patient PBMC samples taken immediately prior to or after diagnosis were truly infected, the PCR assay was at least 57% sensitive in detecting KSHV infection among PBMC samples. No significant differences in CD4+ counts were found for KS patients and homosexual/bisexual patients without KS at the second sample evaluation (Kruskall-Wallis p=0.15) (FIG. 21). CD4+ counts from the single sample from hemophilic AIDS patients were higher than CD4+ counts from KS patients (Kruskall-Wallis p=0.004), although both groups showed evidence of HIV-related immunosuppression.

Longitudinal Studies:

Paired specimens were available from all 21 KS patients and 23 homosexual/bisexual male AIDS control patients who did not develop KS. For the KS group, initial PBMC samples were taken four to 87 months (median 13 months) prior to the onset of KS. Initial PBMC samples from the control group were drawn 13 to 106 months (median 55 months) prior to onset of first nonKS AIDS-defining illness (1987 CDC surveillance definition). 11 of 21 (52%) of KS patients had detectable KSHV DNA in PBMC samples taken prior to KS onset compared to 2 of 19 (11%, p=0.005) hemophilic control samples, and 1 (4%, p=0.0004) and 2 (9%, p=0.002) of 23 homosexual/bisexual control samples taken at the first and second visits respectively (FIGS. 20A–20B). The figure shows that 7 of the paired KS patient samples were positive at both visits, 5 KS patients and 2 control patients converted from negative to positive and two KS patients and one control patient reverted from positive to negative between visits. The remaining 7 KS patients and 20 control patients were negative at both visits.

For the 5 KS patients that converted from an initial negative PBMC result to a positive result at or near to KS diagnosis, the median length of time between the first sample and the KS diagnosis was 19 months. Three of the 6 KS patients that were negative at both visits had their last PBMC sample drawn 2–3 months prior to onset of illness. It is unknown whether these patients became infected between their last study visit and the KS diagnosis date.

DISCUSSION

Ambroziak and coworkers have found evidence that KSHV preferentially infects CD19+B cells by PBMC subset examination of three patients [19]. Other gammaherpesviruses, such as Epstein-Barr virus (EBV) and herpesvirus saimiri are also lymphotrophic herpesviruses and can cause lymphoproliferative disorders in primates [11, 20].

It is possible that KSHV, like most human herpesviruses, is a ubiquitous infection of adults [21]. EBV, for example, is detectable by PCR in CD19+B lymphocytes from virtually all seropositive persons [22] and approximately 98% MACS study participants had EBV VCA antibodies at entry into the cohort study [23]. The findings, however, are most consistent with control patients having lower KSHV infection rates than cases and that KSHV is specifically associated with the subsequent development of KS. While it is possible that control patients are infected but have an undetectably low KSHV viral PBMC load, the inability to find evidence of infection in control patients under a variety of PCR conditions suggests that the majority of control patients are not infected. Nonetheless, approximately 10% of these patients were KSHV infected and did not develop KS. It is unknown whether or not this is similar to the KSHV infection rate for the general human population.

This study demonstrates that KSHV infection is both strongly associated with KS and precedes onset of disease in the majority of patients. 57% of KS patients had detectable KSHV infection at their second follow-up visit (52% prior to the onset of KS] compared to only 9% of homosexual/bisexual (p=0.002) and 11 of hemophilic control patients (p=0.005). Despite similar CD4+ levels between homosexual/bisexual KS cases and controls, KSHV DNA positivity rates were significantly higher for cases at both the first (p=0.005) and second sample visits indicating that immunosuppression alone was not responsible for these elevated detection rates. It is also unlikely that KSHV simply colonizes existing KS lesions in AIDS patients since neither patient group had KS at the time the initial sample was obtained. Five KS patients and two homosexual/bisexual control patients converted from a negative to a positive, possibly due to new infection acquired during the study period.

The findings are in contrast to PCR detection of KSHV DNA in all 10 PBMC samples from KS patients by Ambroziak et al. [19]. It is possible that the assay was not sensitive enough to detect virus in all samples since it was required that each positive sample to be repeatedly positive by two independent primers in blinded PCR assays. This appears unlikely, however, given the sensitivity of the PCR nested primer sets. The 7 KS patients who were persistently negative on both paired samples may represent an aviremic or low viral load subpopulation of KS patients. The PCR conditions test a DNA amount equivalent to approximately $2 \times 10^3$ lymphocytes; an average viral load less than 1 copy per $2 \times 10^3$ cells may be negative in the assay. Two KS patients and a homosexual/bisexual control patient initially positive for KSHV PCR amplification reverted to negative in samples drawn after diagnosis. These results probably reflect inability to detect KSHV DNA in peripheral blood rather than true loss of infection although more detailed studies of the natural history of infection are needed.

The study was designed to answer the fundamental question of whether or not infection with KSHV precedes development of the KS phenotype. The findings indicate that there is a strong antecedent association between KSHV infection and KS. This temporal relationship is an absolute requirement for establishing that KSHV is central to the causal pathway for developing KS. This study contributes additional evidence for a possible causal role for this virus in the development of KS.

REFERENCES

1. Katz M H, Hessol N A, Buchbinder S P, Hirozawa A, O'Malley P, Holmberg S D. Temporal trends of opportunistic infections and malignancies in homosexual men with AIDS. J Infect Dis. 1994;170:198–202.
2. Beral V, Peterman T A, Berkelman R L, Jaffe H W. Kaposi's sarcoma among persons with AIDS: a sexually transmitted infection? Lancet. 1990;335:123–128.

3. Archibald C P, Schechter M T, Le TN, Craib K J P, Montaner J S G, O'Shaughnessy M V. Evidence for a sexually transmitted cofactor for AIDS-related Kaposi's sarcoma in a cohort of homosexual men. Epidemiol. 1992;3:203–209.
4. Beral V, Bull D, Jaffe H, Evans B, Gill N, Tillett H et al. Is risk of Kaposi's sarcoma in AIDS patients in Britain increased if sexual partners came from United States or Africa? BMJ. 1991;302:624–5.
5. Beral V. Epidemiology of Kaposi's sarcoma.
   Cancer, HIV and AIDS. London: Imperial Cancer Research Fund; 1991:5–22.
6. Chang Y, Cesarman E, Pessin M S, Lee F, Culpepper J, Knowles D M, et al. Identification of herpesvirus-like DNA sequences in AIDS-associated Kaposi's sarcoma. Science. 1994;265:1865–69.
7. Moore P S, Chang Y. Detection of herpesvirus-like DNA sequences in Kaposi's sarcoma lesions from persons with and without HIV infection. New England J Med. 1995;332:1181–1185.
8. Boshoff C, Whitby D, Hatziionnou T, Fisher C, van der Walt J, Hatzakis A et al. Kaposi's sarcoma-associated herpesvirus in HIV-negative Kaposi's sarcoma. Lancet. 1995;345:1043–44.
9. Su I-J, Hsu Y-S, Chang Y-C, Wang I-W.
   Herpesvirus-like DNA sequence in Kaposi's sarcoma from AIDS and non-AIDS patients in Taiwan.
   Lancet. 1995;345:722–23.
10. Dupin N, Grandadam M, Calvez V, Gorin I, Aubin J T, Harvard S, et al. Herpesvirus-like DNA in patients with Mediterranean Kaposi's sarcoma. Lancet. 1995;345:761–2.
11. Miller G. Oncogenicity of Epstein-Barr virus. J Infect Dis. 1974;130:187–205.
12. Hill A B. Environment and disease: association or causation? Proc Roy Soc Med. 1965;58:295–300.
13. Susser M. Judgment and causal inference: criteria in epidemiologic studies. Am J Epid. 1977;105:1–15.
14. Fishbein D B, Kaplan J E, Spira T J, Miller B, Schonberger L B, Pinsky P F, et al. Unexplained lymphadenopathy in homosexual men: a longitudinal study. JAMA. 1985;254:930–5.
15. Holmberg S D. Possible cofactors for the development of AIDS-related neoplasms. Cancer Detection and Prevention. 1990;14:331–336.
16. Kaslow R A, Ostrow D G, Detels R, Phair J P, Polk B F, Rinaldo C R. The Multicenter AIDS Cohort Study: rationale, organization and selected characteristics of the participants. Am J Epidemiol. 1987;126:310–318.
17. Wolinsky S, Rinaldo C, Kwok S, Sinsky J, Gupta P, Imagawa D, et al. Human immunodeficiency virus type 1 (HIV-1) infection a median of 18 months before a diagnostic Western blot. Ann Internal Med. 1989;111:961.
18. Bauer H M, Ting Y, Greer C E, Chambers J C, Tashiro C J, Chimera J, et al. Genital papillomavirus infection in female university students as determined by a PCR-based method. JAMA. 1991;265:2809–10.
19. Ambroziak J A, Blackbourn D J, Herndier B G, Glogau R G, Gullett J H, McDonald A R, et al. Herpes-like sequences in HIV-infected and uninfected Kaposi's sarcoma patients. Science. 1995;268:582–583.
20. Roizman B. The family Herpesviridae. In: Roizman B, Whitley R J, Lopez C, eds. The Human Herpeviruses. New York: Raven Press, Ltd.; 1993:1–9.
21. Roizman B. New viral footprints in Kaposi's sarcoma. N Engl J Med. 1995;332:1227–1228.
22. Miyashita E M, Yang B, Lam K M C, Crawford D H, Thorley-Lawson D A. A novel form of Epstein-Barr virus latency in normal B cells in vivo. Cell. 1995;80:593–601.
23. Rinaldo C R, Kingsley L A, Lyter D W, Rabin B S, Atchison R W, Bodner A J, et al. Association of HTLV-III with Epstein-Barr virus infection and abnormalities of T lymphocytes in homosexual men. J Infect Dis. 1986;154:556–61.

EXPERIMENTAL DETAILS SECTION IV

To determine if the KHV-KS virus is also present in both endemic and HIV-associated KS lesions from African patients, formalin-fixed, paraffin-embedded tissues from both HIV seropositive and HIV seropositive Ugandan KS patients were compared to cancer tissues from patients without KS in a blinded case-control study.

Patient Enrollment: Archival KS biopsy specimens were selected from approximately equal numbers of HIV-associated and endemic HIV-negative KS patients enrolled in an ongoing case-control study of cancer and HIV infection at Makerere University, Kampala Uganda. Control tissues were consecutive archival biopsies from patients with various malignancies enrolled in the same study, chosen without prior knowledge of HIV serostatus. All patients were tested for HIV antibody (measured by Cambridge Bioscience Recombigen Elisa assay).

Tissue preparation: Each sample examined was from an individual patient. Approximately ten tissue sections were cut (10 micron) from each paraffin block using a cleaned knife blade for each specimen. Tissue sections were deparaffinized by extracting the sections twice with 1 ml xylene for 15 min. followed by two extractions with 100% ethanol for 15 min. The remaining pellet was then resuspended and incubated overnight at 500 C in 0.5 ml of lysis buffer (25 mM KCl, 10 mM Tris-HCl, pH 8.3, 1.4 mM MgCl2, 0.01% gelatin, 1 mg/ml proteinase K). DNA was extracted with phenol/chloroform, ethanol precipitated and resuspended in 10 mM Tris-HCl, 0.1 mM EDTA, pH 8.3.

PCR Amplification: 0.2–0.4 ug of DNA was used in PCR reactions with $KS330_{233}$ primers as previously described [7]. The samples which were negative were retested by nested PCR amplification, which is approximately $10^2$–$10^3$ fold more sensitive in detecting $KS330_{233}$ sequence than the previously published $KS330_{233}$ primer set [7]. These samples were tested twice and samples showing discordant results were retested a third time. 51 of 74 samples initially examined were available for independent extraction and testing at Chester Beatty Laboratories, London using identical nested PCR primers and conditions to ensure fidelity of the PCR results. Results from eight samples were discordant between laboratories and were removed from the analysis as uninterpretable (four positive samples from each laboratory). Statistical comparisons were made using EPI-INFO ver. 5 (USD, Stone Mt. Ga., USA) with exact confidence intervals.

RESULTS

Of 66 tissues examined, 24 were from AIDS-KS cases, 20 were from endemic HIV seronegative KS cases, and 22 were from cancer control patients without KS. Seven of the cancer control patients were HIV seropositive and 15 were HIV seronegative (FIG. 22). Tumors examined in the control group included carcinomas of the breast, ovaries, rectum, stomach, and colon, fibrosarcoma, lymphocytic lymphomas, Hodgkin's lymphomas, choriocarcinoma and anaplastic carcinoma of unknown primary site. The median age of AIDS-KS patients was 29 years (range 3–50) compared to 36 years (range 3–79) for endemic KS patients and 38 years (range 21–73) for cancer controls.

Among KS lesions, 39 of 44 (89%) were positive for $KS330_{233}$ PCR product, including KS tissues from 22 of 24 (92%) HIV seropositive and 17 of 20 (85%) HIV seronegative patients. In comparison, 3 of 22 (14%) nonKS cancer control tissues were positive, including 1 of 7 (14%) HIV seropositive and 2 of 15 (13%) HIV seronegative control patients (FIG. 19). These control patients included a 73 year old HIV seronegative male and a 29 year old HIV seronegative female with breast carcinomas, and a 36 year old HIV seropositive female with ovarian carcinoma. The odds ratios for detecting the sequences in tissues from HIV seropositive and HIV seronegative cases and controls was 66 (95% confidence interval (95% C.I.) 3.8–3161) and 36.8 (95% C.I. 4.3–428) respectively. The overall weighted Mantel-Haenzel odds ratio stratified by HIV serostatus was 49.2 (95% C.I. 9.1-335). KS tissues from four HIV seropositive children (ages 3, 5, 6, and 7 years) and four HIV seronegative children (ages 3, 4, 4, and 12 years) were all positive for $KS330_{233}$.

All discordant results (i.e. KSHV negative KS or KSHV positive nonKS cancers) were reviewed microscopically. All $KS330_{233}$ PCR negative KS samples were confirmed to be KS. Likewise, all $KS330_{233}$ PCR positive nonKS cancers were found not to have occult KS histopathologically.

DISCUSSION

These results indicate that KSHV DNA sequences are found not only in AIDS-KS [5], classical KS [6] and transplant KS [7] but also in African KS from both HIV seropositive and seronegative patients. Despite differences in clinical and epidemiological features, KSHV DNA sequences are present in all major clinical subtypes of KS from widely dispersed geographic settings.

This study was performed on banked, formalin-fixed tissues which prevented the use of specific detection assays such as Southern hybridization. DNA extracted after such treatment is often fragmented which reduces the detection sensitivity of PCR and may account for the 5 PCR negative KS samples found in the study. The results, however, are unlikely to be due to PCR contamination or nonspecific amplification. Specimens were tested blindly and a subset of samples were independently extracted and tested at a physically separate laboratory. Specimen blinding is essential to ensure the integrity of results based solely on PCR analyses. A subset of amplicons was sequenced and found to be more than 98% identical to the published $KS330_{233}$ sequence confirming their specific nature and, because of minor sequence variation, making the possibility of contamination unlikely.

In contrast to previous studies in North American and European populations, it was found 3 of 22 control tissues to have evidence of KSHV infection. Since these cancers represent a variety of tissue types, it is unlikely that KSHV has an etiologic role in these tumors. One possible explanation for the findings is that these results reflect the rate of KSHV infection in the nonKS population in Uganda. Four independent controlled studies from North America [5 and 9] Europe [7] and Asia [8] have failed to detect evidence of KSHV infection in over 200 cancer control tissues, with the exception of an unusual AIDS-associated, body-cavity-based lymphoma [9]. Taken together, these studies indicate that DNA-based detection of KSHV infection is rare in most nonKS cancer tissues from developed countries. KSHV infection has been reported in post-transplant skin tumors, although well-controlled studies are needed to confirm that these findings are not due to PCR contamination [10]. Since the rate of HIV-negative KS is much more frequent in Uganda than the United States, detection of KSHV in control tissues from cancer patients in the study may reflect a relatively high prevalence infection in the general Ugandan population.

While KS is extremely rare among children in developed countries [2], the rate of KS in Ugandan children has risen dramatically over the past 3 decades: age-standardized rates (per 100,000) for boys age 0–14 years were 0.25 in 1964–68 and 10.1 in 1992–93. Detection of KSHV genome in KS lesions from prepubertal children suggests that the virus has a nonsexual mode of transmission among Ugandan children. That five of these children were 5 years old or less raises the possibility that the agent can be transmitted perinatally. Whether or not immune tolerance due to perinatal transmission accounts for the more fulminant form of KS occurring in African children remains to be investigated.

REFERENCES

1. Oettle A. G. Geographic and racial differences in the frequency of Kaposi's sarcoma as evidence of environmental or genetic causes. Acta Un Int Cancer 1962;18:330–363.

2. Beral V. Epidemiology of Kaposi's sarcoma. In: Cancer, HIV and AIDS. London: Imperial Cancer Research Fund, 1991: 5–22.

3. Wabinga H. R., Parkin D. M., Wabwire-Mangen F., Mugerwa J. Cancer in Kampala, Uganda, in 1989–91: changes in incidence in the era of AIDS. Int J Cancer 1993;54:26–36.

4. Kestens L. et al. Endemic Kaposi's sarcoma is not associated with immunodeficiency. Int. J. Cancer 1985;36:49–54.

5. Chang Y. et al. Identification of herpesvirus-like DNA sequences in AIDS-associated Kaposi's sarcoma. Science 1994; 266:1865–9.

6. Moore P. S. and Chang Y. Detection of herpesvirus-like DNA sequences in Kaposi's sarcoma lesions from persons with and without HIV infection. New England J Med 1995; 332:1181–85.

7. Boshoff C. et al. Kaposi's sarcoma-associated herpesvirus in HIV negative Kaposi's sarcoma (letter). Lancet 1995; 345:1043–44.

8. Su, I.-J., Hsu, Y.-S., Chang, Y.-C., Wang, I.-W. Herpevirus-like DNA sequence in Kaposi's sarcoma from AIDS and non-AIDS patients in Taiwan. Lancet 1995;345: 722–3.

9. Cesarman E., Chang Y., Moore P. S., Said J. W., Knowles D. M. Kaposi's sarcoma-associated herpesvirus-like DNA sequences are present in AIDS-related body cavity based lymphomas. New England J Med 1995; 332:1186–1191.

10. Rady P. L., et al. Herpesvirus-like DNA sequences in nonKaposi's sarcoma skin lesions of transplant patients. Lancet 1995;345:1339–40.

What is claimed is:

1. An isolated nucleic acid encoding Kaposi's sarcoma-associated herpesvirus interleukin 6 having the amino acid sequence as set forth in SEQ ID NO:1.

2. The isolated nucleic acid of claim 1, wherein the isolated nucleic acid is cDNA.

3. The isolated nucleic acid of claim 1, wherein the isolated nucleic acid is genomic DNA.

4. The isolated nucleic acid of claim 1, wherein the isolated nucleic acid is RNA.

5. The isolated nucleic acid of claim 1 which is labelled with a detectable marker.

6. The isolated nucleic acid of claim 5, wherein the marker is a radioactive label, or a colorimetric, a luminescent, or a fluorescent marker.

7. A replicable vector comprising the isolated nucleic acid of claim 1.

8. A plasmid, cosmid, λ phage or YAC comprising the isolated nucleic acid of claim 1.

9. A host cell containing the vector of claim 7.

10. The cell of claim 9 which is a eukaryotic cell.

11. The cell of claim 9 which is a bacterial cell.

12. A nucleic acid of at least 14 nucleotides which specifically hybridizes with the isolated nucleic acid of claim 1.

13. An antisense molecule which specifically hybridizes to the isolated nucleic acid of claim 1.

* * * * *